US012622805B2

(12) United States Patent
Ow et al.

(10) Patent No.: US 12,622,805 B2
(45) Date of Patent: May 12, 2026

(54) DEVICES AND METHODS FOR TREATING OBSTRUCTIVE BREATHING DISORDERS

(71) Applicants: Randall Ow, Loomis, CA (US); Clarence Emmons, Grants Pass, OR (US)

(72) Inventors: Randall Ow, Loomis, CA (US); Clarence Emmons, Grants Pass, OR (US)

( * ) Notice: Subject to any disclaimer, the term of this patent is extended or adjusted under 35 U.S.C. 154(b) by 225 days.

(21) Appl. No.: 18/460,049

(22) Filed: Sep. 1, 2023

(65) Prior Publication Data

US 2023/0404795 A1 Dec. 21, 2023

Related U.S. Application Data

(63) Continuation-in-part of application No. 17/191,019, filed on Mar. 3, 2021, now Pat. No. 11,806,272, and
(Continued)

(51) Int. Cl.
*A61F 5/56* (2006.01)
*A61B 17/30* (2006.01)

(52) U.S. Cl.
CPC ........ *A61F 5/566* (2013.01); *A61B 2017/306* (2013.01)

(58) Field of Classification Search
CPC .. A61F 5/00; A61F 5/3756; A61F 5/56; A61F 5/566; A61F 2/00; A61F 2/02;
(Continued)

(56) References Cited

U.S. PATENT DOCUMENTS

| | | | |
|---|---|---|---|
| 6,408,851 | B1 | 6/2002 | Karell |
| 6,679,257 | B1 | 1/2004 | Robertson et al. |

(Continued)

FOREIGN PATENT DOCUMENTS

| | | |
|---|---|---|
| EP | 2617460 A2 | 7/2013 |
| FR | 2942954 A1 | 9/2010 |

(Continued)

OTHER PUBLICATIONS

Airlift®, Adjustable Hyoid Suspension Procedure Guide, Siesta Medical, Inc., 2020. (2 pages).
(Continued)

*Primary Examiner* — Alireza Nia
*Assistant Examiner* — Gina Mccarthy
(74) *Attorney, Agent, or Firm* — Aurora Consulting LLC; Ashley Sloat; Tiffany Miller

(57) ABSTRACT

Described herein are devices and methods of treating obstructive breathing disorders in a patient. A method may include: attaching an anchor to a dorsal region of a tongue body; applying an external force to the tongue body; and adjusting a magnitude of the external force. In some embodiments, the magnitude of the external force is adjustable across multiple levels based on one or more of: patient comfort, desired therapeutic effect, or patient wake or sleep state. In some embodiments, at least a portion of the external force is directed along an anterior direction. In some embodiments, the external force causes at least one of the following actions: anterior displacement of a portion of the posterior tongue during sleep or reducing posterior displacement of a portion of the tongue during sleep.

20 Claims, 44 Drawing Sheets

Related U.S. Application Data a continuation-in-part of application No. PCT/US2022/018650, filed on Mar. 3, 2022.

(60) Provisional application No. 62/984,792, filed on Mar. 4, 2020, provisional application No. 63/241,982, filed on Sep. 8, 2021.

(58) Field of Classification Search
CPC .............. A61M 16/0495; A61M 16/20; A61M 2205/07; A61M 2205/071; A61M 2205/073; A61B 17/00; A61B 17/04; A61B 17/24; A61B 17/68; A61B 17/84; A61B 13/00; Y10S 602/902
See application file for complete search history.

(56) References Cited

U.S. PATENT DOCUMENTS

| | | | |
|---|---|---|---|
| 6,997,186 | B2 | 2/2006 | Robertson et al. |
| 7,073,506 | B2 | 7/2006 | Robertson et al. |
| 7,703,460 | B2 | 4/2010 | Conrad et al. |
| 7,845,357 | B2 | 12/2010 | Buscemi et al. |
| 8,371,307 | B2 | 2/2013 | Hirotsuka et al. |
| 8,556,797 | B2 | 10/2013 | Weadock et al. |
| 9,421,073 | B2 | 8/2016 | Makower et al. |
| 10,195,010 | B2 | 2/2019 | Sanders |
| 10,736,771 | B2 | 8/2020 | Sanders et al. |
| 2002/0056462 | A1 | 5/2002 | Conrad et al. |
| 2005/0004417 | A1 | 1/2005 | Nelson et al. |
| 2007/0163603 | A1 | 7/2007 | Sikora |
| 2008/0053461 | A1 | 3/2008 | Hirotsuka et al. |
| 2008/0066765 | A1 | 3/2008 | Paraschac et al. |
| 2008/0208265 | A1 | 8/2008 | Frazier et al. |
| 2011/0100377 | A1 | 5/2011 | Weadock et al. |
| 2012/0022389 | A1 | 1/2012 | Sanders |
| 2013/0085546 | A1* | 4/2013 | Bolea ................... A61N 1/3601 607/42 |
| 2013/0180528 | A1 | 7/2013 | Zhou et al. |
| 2016/0022470 | A1* | 1/2016 | Gillis ........................ A61F 5/56 128/848 |
| 2017/0020506 | A1 | 1/2017 | Feezor et al. |
| 2018/0168850 | A1* | 6/2018 | Thompson .............. A61F 5/566 |
| 2019/0175169 | A1 | 6/2019 | Burg et al. |
| 2020/0069320 | A1 | 3/2020 | Sanders et al. |
| 2020/0305859 | A1 | 10/2020 | Hendricks et al. |

FOREIGN PATENT DOCUMENTS

| | | | | |
|---|---|---|---|---|
| WO | 2010051195 | A1 | 5/2010 | |
| WO | 2011068952 | A1 | 6/2011 | |
| WO | 2013182893 | A2 | 12/2013 | |
| WO | WO-2017135907 | A1 * | 8/2017 | ............. A61F 5/566 |
| WO | 2018200063 | A1 | 11/2018 | |
| WO | 2020142519 | A1 | 7/2020 | |

OTHER PUBLICATIONS

Airlift®, Hyoid Suspension, Siesta Medical, Inc., 2020. (2 pages).

Bradford, Alina, The Tongue: Facts, Function & Diseases, Oct. 15, 2015 [retrieved on Jul. 18, 2023]. Retrieved from the internet, <URL: https://www.livescience.com/52362-tongue.html (Year: 2015) (11 pages).

D Mcgeorge, The "Niplette": an instrument for the non-surgical correction of inverted nipples, British Journal of Plastic Surgery, 47, 1994, p. 46-49. (4 pages).

E. Gillis et al., article entitled "A novel implantable device for a minimally invasive surgical treatment of obstructive sleep apnea: design and preclinical safety assessment," Nature and Science of Sleep, Jul. 20, 2016, 2016:8, p. 249-258, Dovepress. (10 pages).

Filifan, Reham et al., Double lingual frenulum: a case report, Jul. 26, 2020, Journal of Medical Case Reports, 14, Article No. 116, [ online], [retrieved on Mar. 1, 2023]. Retrieved from the Internet <URL: https://jmedicalcasereports.biomedcentral.com/articles/ 10.1186/ s13256-020-02440-7#:-:text=Walkero/o (Year: 2020).

International Preliminary Report on Patentability re PCT/US2022/ 018650 issued Aug. 29, 2023 (6 pages).

International Search Report dated Jun. 29, 2022 re PCT/US22/ 18650 (4 pages).

L Mu et al., article entitled "Human Tongue Neuroanatomy: Nerve Supply and Motor Endplates," Clin Anat., Oct. 2010, 23(7), p. 777-791. (27 pages).

L Mu et al., article entitled "Sensory Innervation of the Human Soft Palate," The Anatomical Record, 2018, 301: p. 1861-1870, Wiley Periodicals, Inc. (10 pages).

LinguaFlex Tongue Retractor (LTR) for the Treatment of OSA and Snoring in Adults, Linguaflex, Inc., ClinicalTrials.gov Identifier: NCT04129229, Oct. 16, 2019. (6 pages).

Sleep Lab, 2023, [online], [retrieved Mar. 1, 2023}. Retrieved from the Internet <URL: https://www.madison-health.com/sleeplab.php (Year: 2023).

V. Pavelec et al., article entitled "A novel implantable device for the treatment of obstructive sleep apnea: clinical safety and feasibility," Nature and Science of Sleep, May 4, 2016, 2016:8, p. 137-144, Dovepress. (8 pages).

Watson, Stephanie, What Causes Swollen Taste Buds, Mar. 7, 2019 [online], [retrieved on Feb. 28, 2023]. Retrieved from the Internet <URL: https://www.healthline.com/health/swollen-taste-buds (Year: 2019).

Written Opinion dated Jun. 29, 2022 re PCT/US22/18650 (5 pages).

Y Muranishi et al., article entitled "A novel suction-based lung-stabilizing device for video-assisted thoracoscopic surgical procedures," Journal of Thoracic Disease, 2018; 10(2), p. 1081-1083. (3 pages).

Airlift®, Dise, Hypopharyngeal Collapse & the Airlift Airway Effect, Siesta Medical, Inc. 2020, (2 pages).

AIRvance® Bone Screw System, Tongue and Hyoid Suspension, Medtronic, 2014. (48 pages).

AIRvanceTM System for Obstructive Sleep Apnea from Medtronic, Medtronic, Oct. 13, 2020. (4 pages).

AveoTSD® Anti-Snoring Device, accessed Nov. 24, 2020. (1 page).

EncoreTM Suspension System, Hyoid & Tongue Suspension, Siesta Medical, Inc., 2016 (1 page).

* cited by examiner

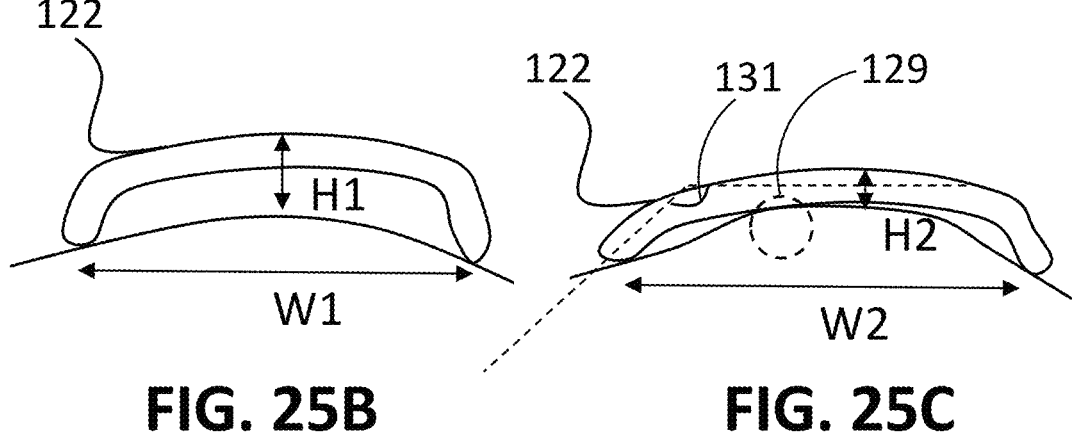
FIG. 25B          FIG. 25C

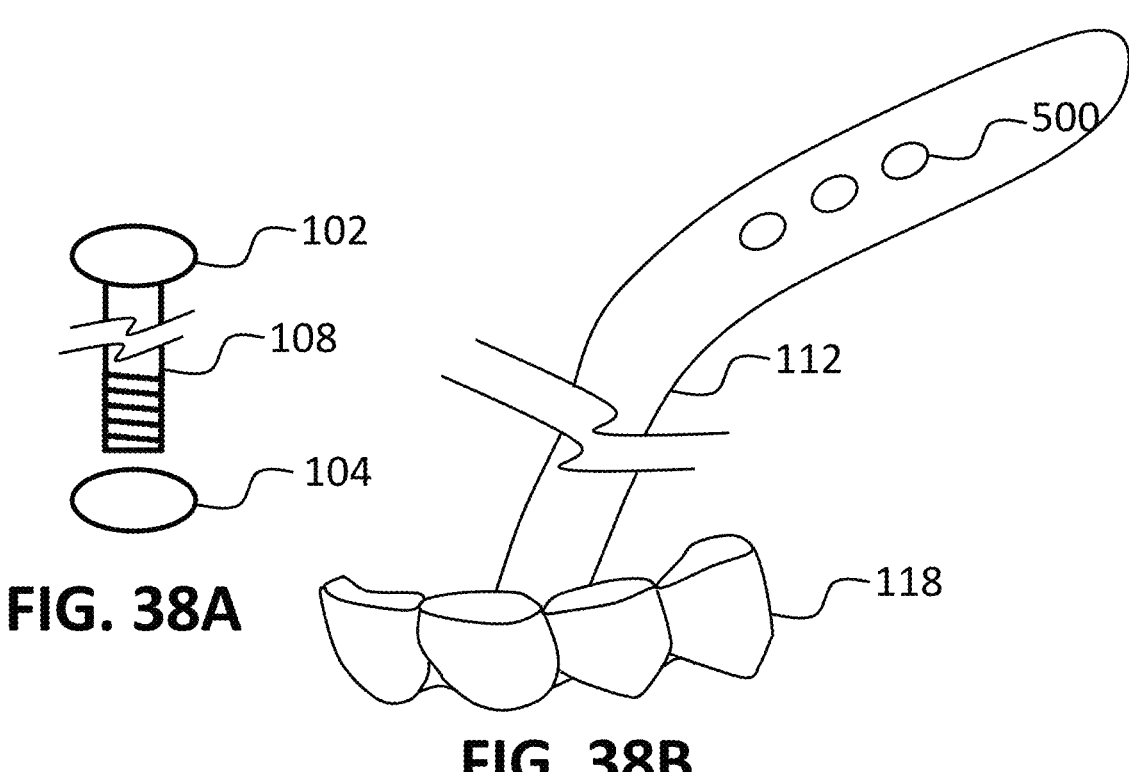
FIG. 38A
FIG. 38B
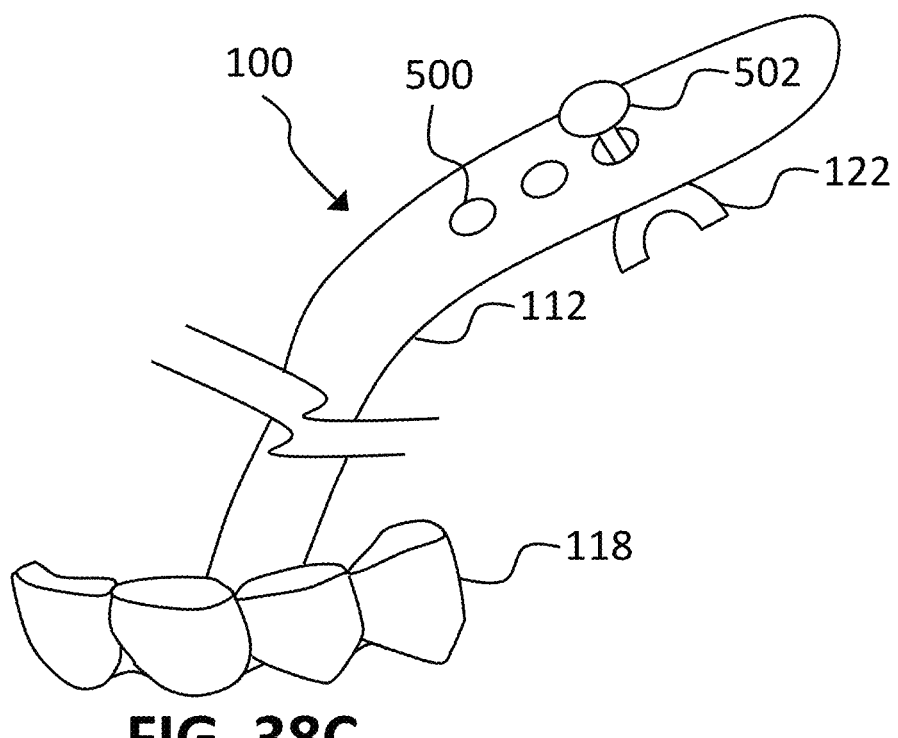
FIG. 38C

P2

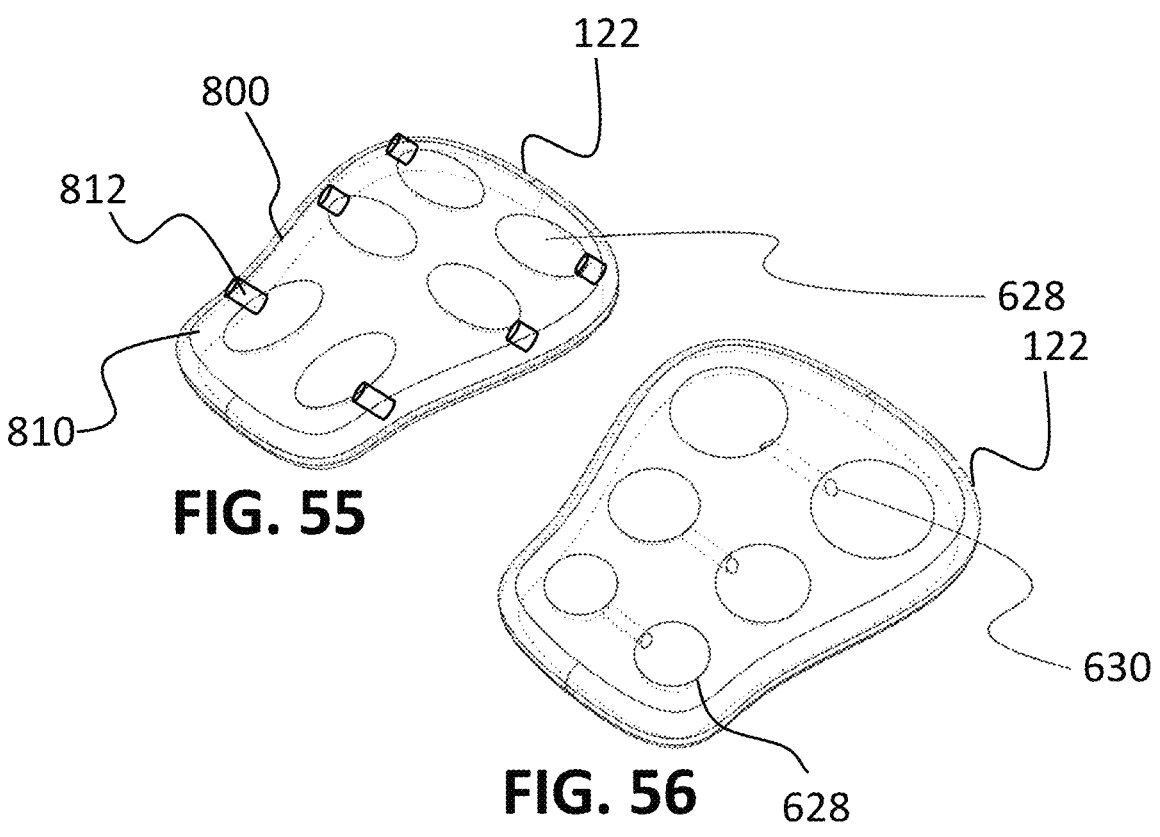
FIG. 55
FIG. 56
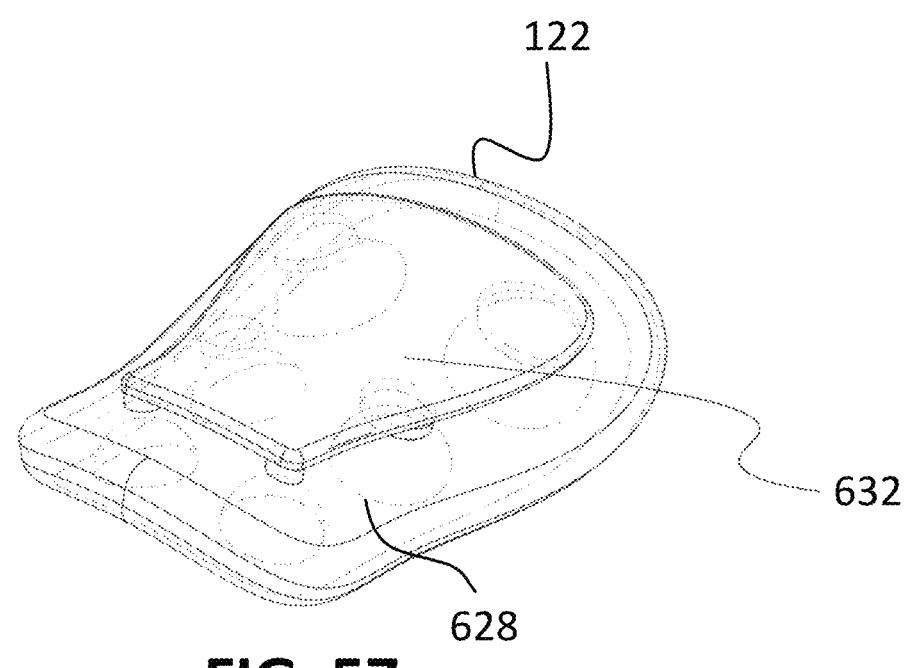
FIG. 57

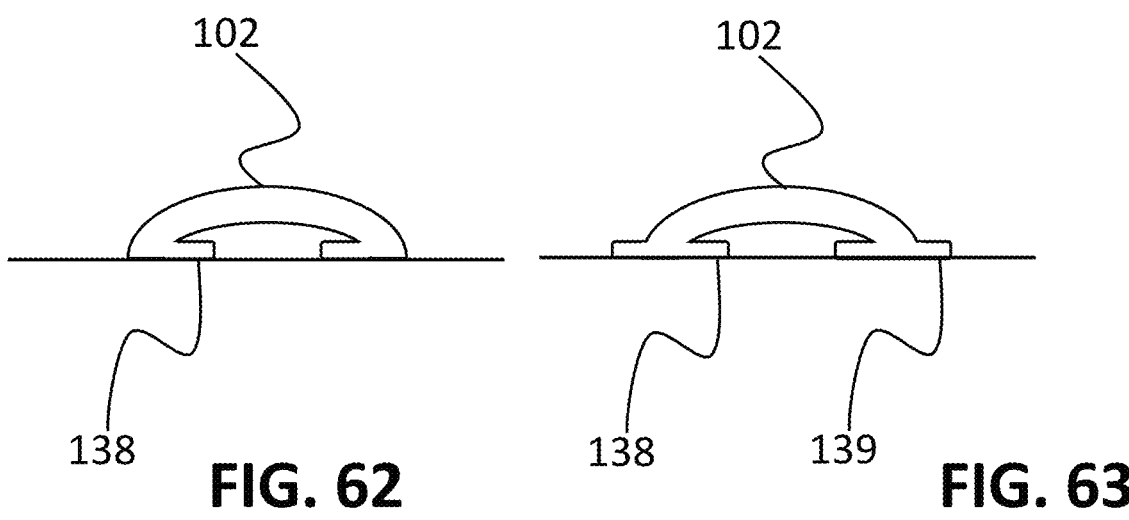
FIG. 62     FIG. 63
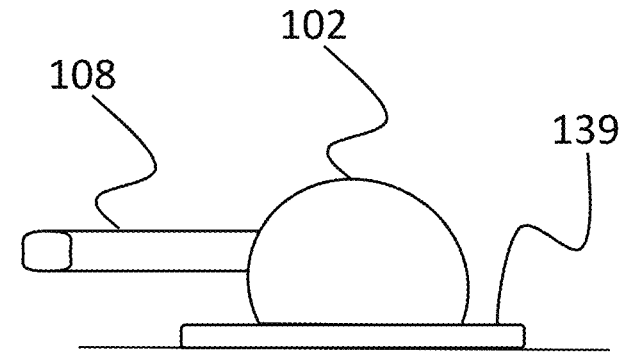
FIG. 64A
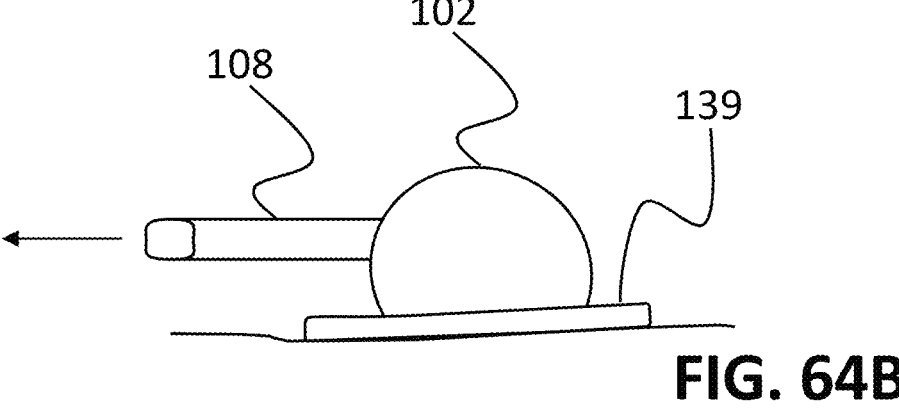
FIG. 64B

DEVICES AND METHODS FOR TREATING OBSTRUCTIVE BREATHING DISORDERS

CROSS-REFERENCE TO RELATED APPLICATIONS

This application is a continuation-in-part of International Patent Application Ser. No. PCT/US2022018650, filed Mar. 3, 2022; and U.S. Nonprovisional patent application Ser. No. 17/191,019, filed Mar. 3, 2021, the contents of each of which are incorporated by reference in their entireties.

U.S. Nonprovisional patent application Ser. No. 17/191,019 claims the priority benefit of U.S. Provisional Patent Application Ser. No. 62/984,792, filed Mar. 4, 2020, which is herein incorporated by reference in its entirety.

International Patent Application Ser. No. PCT/US2022018650, filed Mar. 3, 2022, also claims the priority benefit of U.S. Provisional Patent Application Ser. No. 63/241,982, filed Sep. 8, 2021, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of otolaryngology, and more specifically to the field of obstructive breathing disorders. Described herein are devices and methods for treating obstructive breathing disorders.

BACKGROUND

Sleep apnea is a common disorder affecting more than 15 million adults in the U.S. Patients with sleep apnea experience stopped or shallow breathing when they sleep. The most common type of sleep apnea is obstructive sleep apnea (OSA). The airway of patients with OSA collapses—during sleep. These patients often snore loudly. Since the patient's sleep is interrupted throughout the night, they are often drowsy during daytime. Further, patients with sleep apnea often experience severe fatigue and are very motivated for a solution to their condition. Further, many OSA sufferers have other medical problems such as hypertension, cardiac disease, type 2 diabetes, stroke, and depression because of their OSA. The prevalence of OSA is expected to continue to rise because of the rising obesity rates in the United States.

Treatments include lifestyle changes such as weight loss and avoiding alcohol before sleeping, mouthpieces, breathing devices, and continuous positive airway pressure (CPAP). Patients who do not tolerate or are not helped by these methods may be offered surgery on the nose and/or throat. A major limitation of surgery is the inability to directly address the collapsing tongue base. The tongue base is suspected to be the primary site of obstruction, but surgery on the tongue base is limited due to the serious complications that can occur with invasive procedures on the tongue base itself. Complications include tongue paralysis, permanent swallowing changes, loss of taste and life-threatening bleeding and swelling. Less dangerous surgeries include palatoplasty, hyoid suspension, genioglossal advancement and hypoglossal nerve implantation. But these surgeries are invasive, expensive, and cause a substantial and permanent change to the anatomy. Further, the effect of these surgeries cannot be adjusted after the actual procedure.

Accordingly, there is a large unmet need for a treatment for sleep apnea, especially OSA, that is minimally invasive, easy to perform and does not cause significant alteration of the patient's anatomy, such that it can be easily reversed or adjusted if needed.

SUMMARY

One aspect of the present disclosure is directed to a device for treating obstructive breathing disorders in a patient. In some embodiments, the device includes: a suction well having a body having: a tissue contacting region on a first side of the body and adapted for attachment to a region of a tongue, such that at least a portion of the tissue contacting region distorts, on application of a vacuum, to conform to the region of the tongue, a non-tissue contacting region on a second side of the body opposite the first side, a perimeter at an interface between the first side and the second side, and a flap extending at least partially about the perimeter of the body.

In any of the preceding embodiments, the flap performs a function selected from the group consisting of: resisting rotation, resisting sliding over a tissue surface, and increasing a vacuum on application of a force to the suction well.

Another aspect of the present disclosure is directed to a device for treating obstructive breathing disorders in a patient. In some embodiments, the device includes a suction anchor comprising a body having: a tissue contacting region on a first side of the body and adapted for attachment to a region of a tongue, the tissue contacting region comprising at least one suction well, and a non-tissue contacting region on a second side of the body opposite the first side, a second anchor for attachment to a region of a head of a user; and a connector for connecting the suction anchor to the second anchor, such that a length of the connector between the suction anchor and the second anchor is adjustable.

In any of the preceding embodiments, at least a portion of the tissue contacting region distorts, on application of a vacuum, to conform to the region of the tongue.

In any of the preceding embodiments, the connector does not exert a displacement force on the tongue when the user is in an awake state.

In any of the preceding embodiments, the connector exerts a force on the tongue when the user is in a sleep state to reduce posterior displacement of a portion of the tongue.

In any of the preceding embodiments, the suction anchor in a resting state is configured to deform, upon application of a vacuum, to a deformed state such that a height of the suction anchor in the deformed state decreases by about 0.5× to about 2× when compared to a height of the suction anchor in the resting state.

In any of the preceding embodiments, the suction anchor in a resting state is configured to deform, upon application of a vacuum, to a deformed state such that a width of the suction anchor in the deformed state increases by about 0.5× to about 2× when compared to a width of the suction anchor in the resting state.

In any of the preceding embodiments, the tissue contacting region has a Shore A hardness of less than about 20 or a Shore 00 hardness of less than about 70.

In any of the preceding embodiments, the suction well comprises a fluid permeable material.

In any of the preceding embodiments, the suction well comprises a plurality of suction wells distributed on the first side of the suction anchor. In any of the preceding embodiments, at least two suction wells of the plurality of suction wells are independently pressurizable. In any of the preceding embodiments, at least two of the suction wells are located on separate suction anchors.

In any of the preceding embodiments, the device further includes a second connector configured to connect the suction anchor to the second anchor or a third anchor, wherein the connector is configured to deliver a vacuum to a subset of the plurality of suction wells and the second connector is configured to deliver the vacuum to a second subset of the plurality of suction wells.

In any of the preceding embodiments, at least one suction well of the subset of the plurality of suction wells is also in the second subset of the plurality of suction wells.

In any of the preceding embodiments, the device further includes a second connector, configured to connect the suction anchor to the second anchor or a third anchor, wherein both the connector and the second connector are configured to deliver a vacuum to the plurality of suction wells.

In any of the preceding embodiments, the device further includes a fluid connection between adjacent suction wells.

In any of the preceding embodiments, the body defines a suction lumen that is configured to connect to each of the plurality of suction wells via a fluid connection such that there is fluid communication between the suction lumen and each of the plurality of suction wells.

In any of the preceding embodiments, the device further includes a valve that is configured to retain vacuum in the suction anchor after a vacuum source is removed.

In any of the preceding embodiments, a length of the connector is adjustable.

In any of the preceding embodiments, the device further includes a means for connecting to a vacuum source in fluid communication with a lumen defined by the connector and a cavity defined by the body of the suction anchor, wherein the vacuum source is configured to create a vacuum in the suction anchor via the connector.

In any of the preceding embodiments, a means comprises any of the connectors described elsewhere herein.

In any of the preceding embodiments, the device further includes means for connecting to a vacuum source in fluid communication with a cavity defined by the body of the suction anchor, wherein the vacuum source is configured to create a vacuum in the suction anchor via the connector.

In any of the preceding embodiments, the vacuum source comprises one of: a syringe, a balloon structure, a bulb, a pump, and elements comprising a displaceable portion that generates a vacuum.

In any of the preceding embodiments, the device further includes a pivot joint between the suction anchor and the connector.

In any of the preceding embodiments, the region of the head comprises one or more teeth, such that the second anchor is adapted for attachment to the one or more teeth.

In any of the preceding embodiments, the device further includes a vacuum source that generates sufficient vacuum to displace a region of the tongue into the suction anchor, wherein the volume of the region of the tongue is less than about 0.5 cc (cm^3).

In any of the preceding embodiments, the displacement of the region of the tongue does not significantly displace other regions of the tongue.

In any of the preceding embodiments, the device further includes a plurality of suction anchors, such that a first suction anchor is in fluid communication with the connector and a second suction anchor is in fluid communication with a second connector.

In any of the preceding embodiments, the device further includes a mechanism configured to resist dislodgement of the suction anchor. In any of the preceding embodiments, the mechanism is selected from the group consisting of: a band, a flap, and a pivot joint.

In any of the preceding embodiments, the flap contacts the surface of the tongue and performs a function selected from the group consisting of: resist rotation, resist sliding over a tissue surface, and increase a vacuum on application of a force to the suction anchor.

In any of the preceding embodiments, the flap is located on one or more of: within a cavity of the suction anchor, at least partially around a perimeter of the suction anchor, or on an external region of the suction anchor.

In any of the preceding embodiments, the flap is flexible such that an orientation or an angle of the flap relative to the rest of the suction anchor changes as a force is applied to the suction anchor.

In any of the preceding embodiments, the band contacts the surface of the tongue and performs a function selected from the group consisting of: increase the force with which an anchor presses onto the tongue, improves contact of an anchor with the tongue, prevents an anchor from sliding relative to the tongue surface, prevents the loss of a vacuum, increases patient comfort when a patient uses the device, stabilizes the orientation of an anchor relative to the tongue, and prevents aspiration or choking from one or more device components.

In any of the preceding embodiments, the band is sized to at least partially circumscribe a region of the tongue anterior to the circumvallate papillae.

In any of the preceding embodiments, a length of the band is adjustable.

In any of the preceding embodiments, the device further includes a secondary connector to prevent decoupling of the suction anchor if the connector fails.

Another aspect of the present disclosure is directed to a device for treating obstructive breathing disorders in a patient. In some embodiments, the device includes: a suction anchor comprising a body having: a tissue contacting region on a first side of the body and adapted for attachment to a dorsal region of a tongue, the tissue contacting region comprising at least two suction wells, and a non-tissue contacting region on a second side of the body opposite the first side; a second anchor for attachment to a region of a head of a user; a first connector for connecting a first suction well of the at least two suction wells to the second anchor; and a second connector for connecting a second suction well of the at least two suction wells to the second anchor or a third anchor.

In any of the preceding embodiments, at least a portion of the tissue contacting region distorts, on application of a vacuum, to conform to the dorsal region of the tongue.

In any of the preceding embodiments, a length of each of the first connector and the second connector is adjustable.

In any of the preceding embodiments, the body of the suction anchor further comprises a flap disposed at least partially around a perimeter of the body.

In any of the preceding embodiments, the device further includes a vacuum source in fluid communication with the at least two suction wells via the first and second connectors.

Another aspect of the present disclosure is directed to a device for treating obstructive breathing disorders in a patient. In some embodiments, the device includes: a suction anchor comprising a body having: a tissue contacting region on a first side of the body and adapted for attachment to a dorsal region of a tongue, the tissue contacting region comprising a plurality of suction wells, and a non-tissue contacting region on a second side of the body opposite the first side; a second anchor for attachment to a region of a head of a user; a first connector for connecting a first subset of the plurality of suction wells to the second anchor; and a second connector for connecting a second subset of the plurality of suction wells to the second anchor or a third anchor.

In any of the preceding embodiments, at least a portion of the tissue contacting region distorts, on application of a vacuum, to conform to the dorsal region of the tongue.

In any of the preceding embodiments, the body of the suction anchor further comprises a flap disposed at least partially around a perimeter of the body.

Another aspect of the present disclosure is directed to a device for treating obstructive breathing disorders in a patient. In some embodiments, the device includes: a suction anchor comprising a body having: a tissue contacting region on a first side of the body and adapted for attachment to a dorsal region of a tongue, the tissue contacting region comprising at least two suction wells, and a non-tissue contacting region on a second side of the body opposite the first side; a second anchor for attachment to a region of a head of a user; a first connector for connecting the at least two suction wells to the second anchor; and a second connector for connecting the at least two suction wells to the second anchor or a third anchor.

In any of the preceding embodiments, at least a portion of the tissue contacting region distorts, on application of a vacuum, to conform to the dorsal region of the tongue;

Another aspect of the present disclosure is directed to a method of treating obstructive breathing disorders in a patient. In some embodiments, the method may include attaching an anchor to a dorsal region of a tongue body; applying an external force to the tongue body through the anchor; and adjusting a magnitude of the external force. In some embodiments, the magnitude of the external force is adjustable across multiple levels based on one or more of: patient comfort, desired therapeutic effect, or patient wake or sleep state. In some embodiments, at least a portion of the external force is directed along an anterior direction. In some embodiments, the external force causes at least one of the following actions: anterior displacement of a portion of the posterior tongue during sleep or reducing posterior displacement of a portion of the tongue during sleep.

In some embodiments, attaching includes positioning the anchor in an anterior two thirds portion of the tongue body. In some embodiments, attaching includes positioning the anchor anterior to a circumvallate papillae of the tongue body. In some embodiments, attaching includes positioning the anchor about 1 cm to about 3 cm posterior to a tip of the tongue body.

In some embodiments, attaching includes applying a suction force to couple the anchor to the dorsal region of the tongue body.

In some embodiments, attaching includes inserting an anchor through a portion of the dorsal region of the tongue body.

In some embodiments, the forces are about 0.01 N to about 5 N.

In some embodiments, the method further includes reducing a force on the tongue body to zero force when the patient is at least partially upright or awake.

In some embodiments, applying the external force occurs when the patient is lying down or asleep.

In some embodiments, the method further includes simulating a sleep state and attaching a temporary anchor to the dorsal region of the tongue body before attaching the anchor to the dorsal region of the tongue body.

In some embodiments, the method further includes generating a positive airway pressure to further create an anterior displacement force on one or more of: a tongue region or a soft palate region.

Another aspect of the present disclosure is directed to a method of treating obstructive breathing disorders in a patient. In some embodiments, the method includes providing a device comprising a suction anchor reversibly attached to a dorsal region of a tongue body; attaching a suction anchor of the device to the dorsal region of the tongue body; applying an external force to the tongue body; and adjusting a magnitude of the external force.

In some embodiments, the device further includes: a vacuum generating element defining a chamber fluidly connected to a lumen defined by an elongate member in fluid communication with the suction anchor; a valve having an open state and a closed state, such that, in the open state, at least a partial vacuum force is applied to the suction anchor; and an external anchor configured to couple the device to a body portion of the patient. Although, as one of skill in the art will appreciate, any of the devices described herein may be used with this method.

In some embodiments, the magnitude of the external force is adjustable across multiple levels based on one or more of: patient comfort, desired therapeutic effect, or patient wake or sleep state.

In some embodiments, at least a portion of the external force is directed along the anterior direction.

In some embodiments, the external force causes at least one of the following actions: anterior displacement of a portion of the posterior tongue during sleep or reducing posterior displacement of a portion of the tongue during sleep.

In some embodiments, the vacuum generating element includes a syringe.

In some embodiments, the elongate member includes a flexible strap that defines one or more apertures that are configured to be coupled to the suction anchor.

In some embodiments, the device further includes a secondary connector to prevent decoupling of the suction anchor from the device when the elongate member fails.

In some embodiments, the method further includes identifying one or more anatomical regions responsible for obstructing an upper airway of the patient.

In some embodiments, the method further includes adjusting the anchor based on said identifying.

Another aspect of the present disclosure is directed to a method of treating obstructive breathing disorders in a patient. In some embodiments, the method includes attaching an anchor to a dorsal region of a tongue body; applying an external force to the tongue body through the anchor; and adjusting a magnitude of the external force.

In some embodiments, the magnitude includes a first magnitude when the patient is at least partially upright, a second magnitude when the patient is lying down, and one or more intermediate magnitudes, between the first and second magnitudes, based on one or more of: patient comfort, desired therapeutic effect, or patient wake or sleep state.

In some embodiments, at least a portion of the external force is directed along an anterior direction.

In some embodiments, the external force causes at least one of the following actions: anterior displacement of a portion of the posterior tongue during sleep or reducing posterior displacement of a portion of the tongue during sleep.

In some embodiments, the method further includes tapering the second magnitude of the external force over time to wean the patient from the treatment.

In some embodiments, the first magnitude of the external force is substantially zero.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIG. 25B shows a first configuration of an embodiment of a suction anchor.

FIG. 25C shows a second configuration of the embodiment of FIG. 25B.

FIG. 38A shows one embodiment of an anchor of a multi-level adjustable device.

FIG. 38B shows one embodiment of a multi-level adjustable device using a tongue anchor.

FIG. 38C shows another embodiment of a multi-level adjustable device using a surface anchor.

FIGS. 43-46A show various steps of a method of applying a displacement force to a tongue using a surface anchor-based device.

FIG. 55 shows another embodiment of a suction-based device comprising multiple suction wells.

FIG. 56 shows another embodiment of a suction-based device comprising multiple suction wells.

FIG. 57 shows an embodiment of a suction anchor with a palate actuated suction mechanism.

FIG. 62 shows an embodiment of a suction anchor comprising one or more internal flaps that contact the surface of the tongue and are configured to resist dislodgement of the suction anchor.

FIG. 63 shows an embodiment of a suction anchor comprising one or more external flaps that contact the surface of the tongue and are configured to resist dislodgement of the suction anchor.

FIGS. 64A and 64B show one mechanism of action of an embodiment of a suction anchor comprising one or more external flaps.

Figure 1:
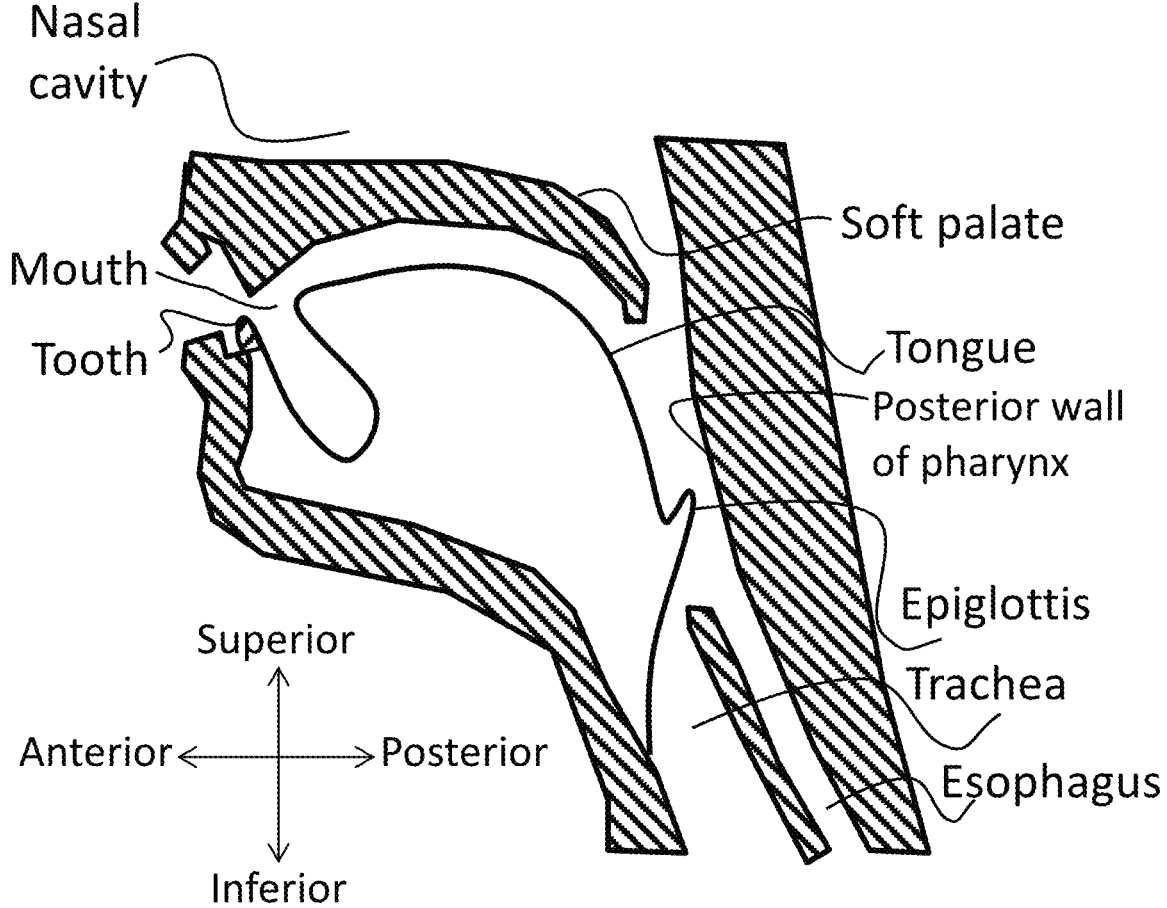
FIG. 1 shows a section through a human head showing the general anatomy and the convention used to indicate direction, as used herein.
Figure 2:
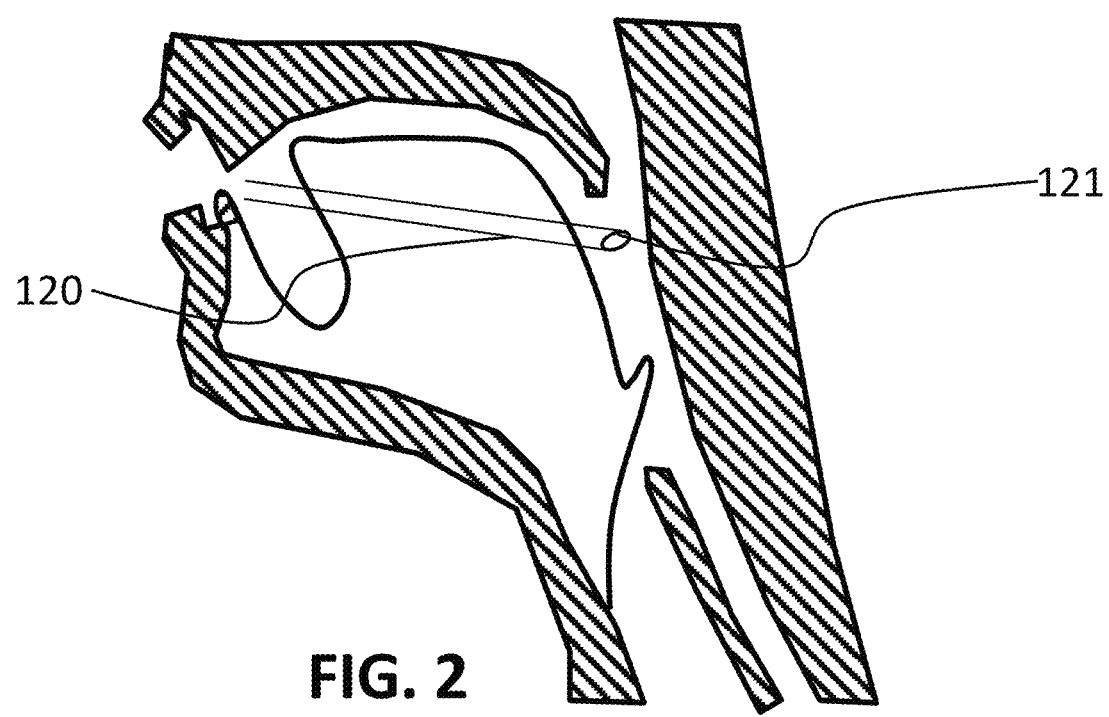
FIG. 2 shows one embodiment of a method of passing a penetrating element through a tongue.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

In general, the devices shown and described herein may be configured to retract or displace a tissue. For example, the devices and methods shown and described herein may be used to displace a tongue, retract an organ or displace it from a surgical field, maintain a bodily structure in an open or closed position, etc. Such displacement or retraction may be temporary or permanent. The volume of tissue that is displaced may be about 0.2 cc to about 1 cc; about 0.1 cc to about 1 cc; about 0.1 cc to about 0.5 cc, or substantially 0.5 cc, where cc is cm^3.

Any of the suction anchors or suction wells described elsewhere herein may comprise a body having a first tissue contacting side and a second non-tissue contacting side. A body of a suction anchor may comprise one or more or a plurality of suction wells disposed on the first side of the body. The body may define a cavity therein that is in fluid communication with a vacuum source and/or a lumen defined by a connector that is configured to connect the vacuum source to the body.

Further, in general, as described herein, an anchor, for example a tissue anchor, may anchor to the tissue via one or more tissue penetrating elements. Additionally, or alternatively, a tissue anchor may pass through the tissue in a first collapsed configuration and may expand to a second expanded configuration during deployment, such that the second expanded configuration is sized and shaped such that it is retained on a surface of the tissue. Additionally, or alternatively, a tissue anchor may be secured to an elongate member after the elongate member is passed through the tissue, such that the anchor is snapped, screwed, threaded, etc. onto the elongate member or the elongate member is passed through and retained (permanently, adjustably, or removably), at least partially, by the tissue anchor. Additionally, or alternatively, a tissue anchor may be retained via suction, magnetic, or electromechanical means, as described elsewhere herein.

In general, any of the devices described herein may be adjusted across multiple levels. For example, force exerted on the tongue by the device may be adjusted to different levels to achieve different degrees of effect or displacement. In one embodiment, a first magnitude of force is applied when the patient is at least partially upright, and a second magnitude of force is applied when the patient is lying down. In some embodiments, one or more intermediate magnitudes of force are applied to one or more device components, between the first and second magnitudes, based on one or more of: patient comfort, desired therapeutic effect, or patient wake or sleep state.

In general, any of the suction anchors or suction wells describe elsewhere herein is configured to evacuate about 0.25 mL to about 10 mL, about 0.25 mL to about 1 mL; about 1 mL to about 5 mL, etc. of air upon attachment to the tongue surface.

The present invention discloses methods and devices that are attached to regions of a patient's tongue. Interventions on certain areas of the tongue such as the tongue base have a high risk of causing heavy bleeding and also tongue swelling which may block the airway. This is especially a concern in certain patients with obstructive sleep apnea that have airways that can be blocked even with minor swelling of the tongue base. Further, the posterior regions of the tongue are sensitive and interventions there can trigger a strong gag reflex. Device embodiments, comprising small separable parts, that are placed in the mouth carry a risk of the small parts separating in the mouth and creating a choking hazard. The various embodiments described herein address these safety concerns. Several method and device embodiments describe minimally invasive or non-invasive interventions in tongue regions away from the tongue base. Further, the tongue remodels in response to long-term tongue implants. Such remodeling may reduce the long-term efficacy of implant-based procedures. The various embodiments described herein address these efficacy concerns.

In this specification, forces and alignments are often described in terms of directions. The convention used is shown in FIG. 1. FIG. 1 shows a section through a human head showing the general anatomy and the convention used to indicate direction, as used herein. Anterior direction is used to describe the direction towards the front of the patient, posterior direction is used to describe the direction towards the back of the patient, superior direction is used to describe the direction towards the top of the patient's head, and inferior direction is used to describe the direction towards the soles of the patient's feet.

Figure 3:
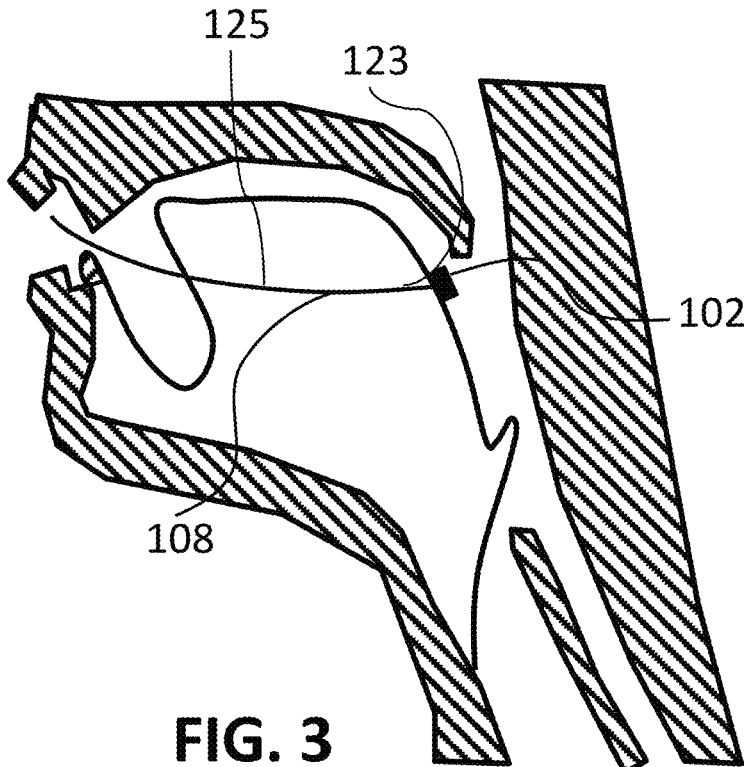
FIG. 3 shows one embodiment of a method of passing a tongue elongate member through a tongue and coupling a tongue anchor to the tongue elongate member on a dorsal surface of the tongue.
Figure 4:
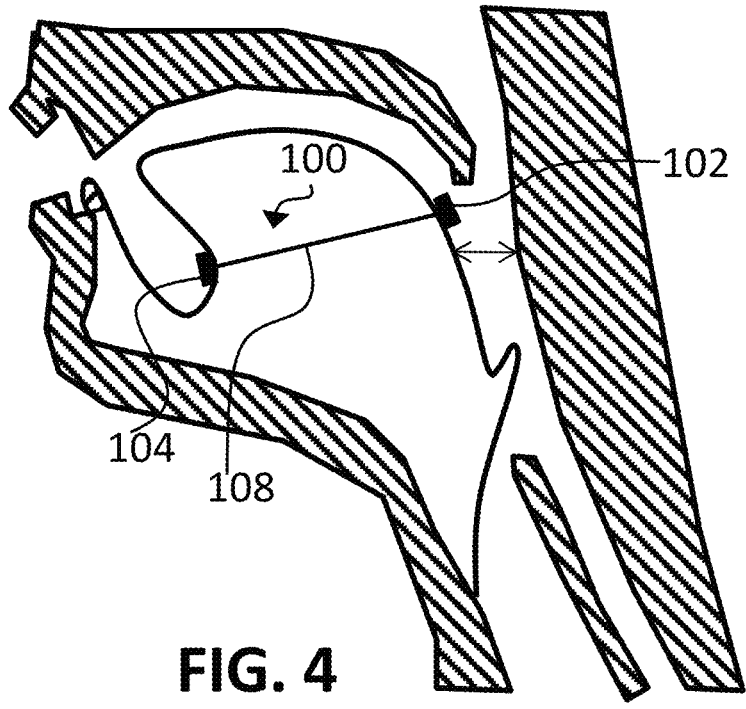
FIG. 4 shows one embodiment of a method of securing a second tongue anchor to an opposite end portion of the tongue elongate member.
Figure 5:
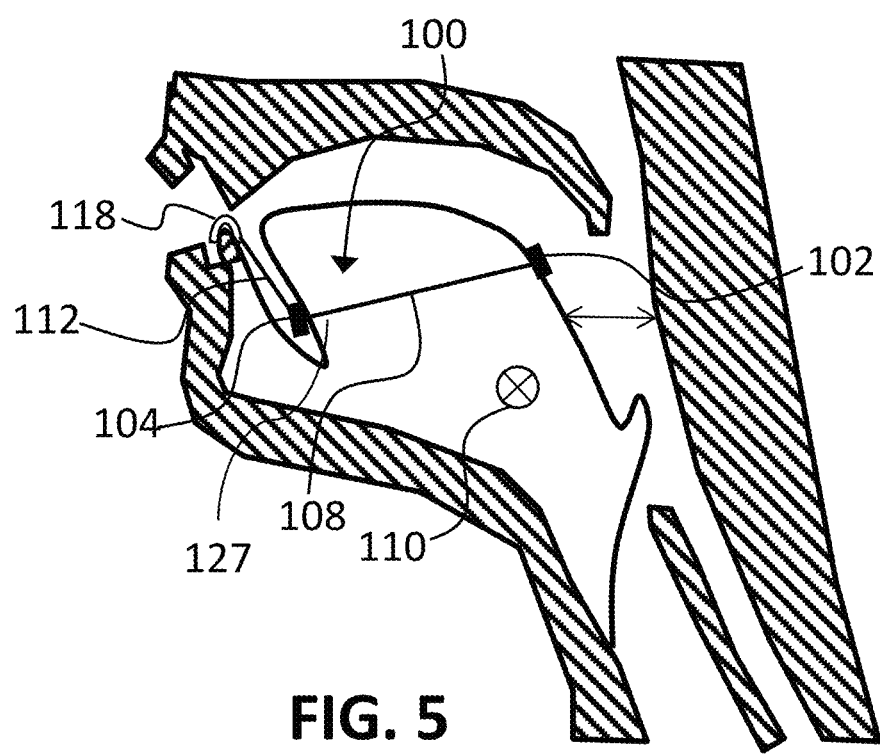
FIG. 5 shows one embodiment of a method of securing the elongate member to a bodily portion using an external anchor.

FIGS. 2-6 show a section through a human head showing the steps of an embodiment of a method of the present invention. At the step of FIG. 2, a penetrating element 120 is used to penetrate a portion of a patient's tongue. Examples of penetrating elements 120 include, but are not limited to needles, cannulas, stylets, trocars, and similar designs. Penetrating element 120 may comprise one or more hollow lumens. In the embodiment shown, a first end 121 of the penetrating element 120 pierces or penetrates a region on the ventral surface of the tongue, passes through a portion of the tongue, and emerges out of a region on the dorsal surface of the tongue. For example, the region of the tongue through which the penetrating element 120 exits may be a mid-region of the tongue, as opposed to a base or tip of the tongue. Further, as shown in FIG. 3, first tongue anchor 102 and first tongue elongate member 108 are placed in the anatomy using the penetration tract created by element 120. In one method embodiment, penetrating element 120 comprises a lumen and first elongate member 108 and anchor 102 are passed through the lumen of penetrating element 120. Once first elongate member 108 and anchor 102 are in place, penetrating element 120 is removed keeping first elongate member 108 and anchor 102 in the anatomy. First tongue anchor 102 may be placed on the dorsal surface of the tongue at a region defined by one or more anatomical landmarks. Examples of such landmarks include, but are not limited to: circumvallate papillae, distance from the tongue tip, distance from the lateral edges of the tongue, etc. In one such embodiment, first tongue anchor 102 is placed on the dorsal surface of the tongue at a region anterior to the circumvallate papillae. A first end 123 of elongate tongue member 108 is coupled to and extends from the first tongue anchor 102. A mid-portion 125 of the elongate tongue member 108 passes through a length of the tongue and emerges out of a region on the ventral surface of the tongue. The length of the tongue through which elongate tongue member 108 passes may range from about 1 cm to about 5 cm; about 0.5 cm to about 3 cm; about 2.5 cm to about 5 cm; about 3 cm to about 6 cm; etc. The region may be defined by one or more anatomical landmarks. Examples of such landmarks include, but are not limited to: tongue body, circumvallate papillae, distance from the tongue tip, distance from the lateral edges of the tongue, distance from the tongue base, etc. Further, as shown in FIG. 4, a second tongue anchor 104 is attached to a second end 127 of tongue elongate member 108. The attachment between the second tongue anchor 104 and the tongue elongate member 108 may be adjustable, reversible, or otherwise removable or adaptable. First tongue anchor 102 may be placed further posterior along the tongue than second tongue anchor 104, such that first tongue anchor 102 is positioned posteriorly and away from the teeth, and more superiorly than second tongue anchor 104. At this location, there is more space in the mouth for first tongue anchor 102. Further, as shown in FIG. 5, device 100 comprising first tongue anchor 102, first tongue elongate member 108, and second tongue anchor 104 is attached to an anatomical region. The attachment is through a second external elongate member 112 that attaches to an external anchor 118 that in turn attaches to a bodily region. In the embodiment shown, external anchor is a dental anchor and the bodily region is a region of the patient's teeth or gums.

Any of the dental anchors or other oral anchors disclosed herein may be designed such that they don't interfere with the natural closing (i.e., physiologic resting position) of the mouth. In one embodiment, the region of the anchor that lies between the patient's upper (maxillary) and lower (mandibular) teeth may be thin enough (e.g., having a thickness about less than 2 mm) such that the patients upper and lower teeth can close naturally when the patient is asleep. In such embodiments, a thickness of a dental anchor over an occluding surface of a tooth may be less than a thickness of the dental anchor over a non-occluding surface (e.g., a lateral surface) of the tooth. In one embodiment, a dental anchor is designed such that it fits into the freeway space i.e., the space between the occluding surfaces of the upper and lower teeth when the mandible is in physiologic resting position. Any of the anchors disclosed herein may be custom designed to fit the patient's anatomy. Such designs allow the patient to sleep more naturally when using the present invention.

Any of the dental anchors disclosed herein may be attached to one or more "side" teeth. Examples of side teeth include, but are not limited to: premolars and molars. In such embodiment, a component of the tension within an elongate member (e.g., elongate member 108, elongate member 112, etc.) is oriented to sideways or along the coronal plane. This force may deviate the tongue to one side when the patient is using the device embodiments of the present invention. Such embodiments are especially suited for patients who are side sleepers. The type and/or location of the dental anchor may be chosen based on which side the patient typically sleeps. In one such embodiment, a dental anchor is attached to a patient's left-side tooth if the patient sleeps on the right side. In one such embodiment, a dental anchor is attached to a patient's right-side tooth if the patient sleeps on the left side. In one embodiment, two dental anchors are attached: one on a left-side tooth and one on a right-side tooth such that the anchoring restricts tongue collapse on either side.

As used herein, external elongate member 112, 114 may form part of the same elongate member as tongue elongate member 108 or external elongate member 112, 114 may be separate from tongue elongate member 108. Said another way, any of the devices described herein may use one elongate member, two elongate members, three elongate members, etc. to accomplish the intended function of the device. Referring to the elongate members separately or as one elongate member is only intended to facilitate description of the various device configurations.

Embodiments of the present invention may be designed and/or placed to produce a clinical effect by a first mechanism discussed in this paragraph. For example, the devices described herein may only apply force to the tongue when the tongue falls back posteriorly. The attachment of device 100 to the region of the patient's teeth or gums may not produce a significant forward displacement force on the tongue when the patient is awake. However, when the patient sleeps, device 100 prevents or restricts the posterior region of the tongue from collapsing on to the posterior wall of the pharynx. In some embodiment herein, device 100 prevents or restricts the posterior movement of the body of the tongue. This is achieved through a therapeutic displacement force created by device 100, wherein at least one component of the displacement force is directed along the anterior direction, such that the displacement force prevents or reduces the posterior displacement of a portion of the posterior tongue when the patient sleeps. The displacement force may be generated using an anatomical region exterior to the tongue. At least one portion of the tongue may be prevented from being displaced in the posterior direction. At least one component of the displacement force is directed along the anterior direction, such that the displacement force causes displacement of a portion of the posterior tongue. In some embodiments herein, device 100 causes displacement of the body of the tongue. The displacement force may be generated using an anatomical region exterior to the tongue. The displacement force may be sufficient to overcome the effect of gravity on the tongue. At least one portion of the tongue is displaced in the anterior direction. As shown in FIG. 5, the displacement force has prevented one or more portions of the tongue from rotating about a rotation axis 110 in a clockwise direction. The rotation axis 110 is perpendicular to the plane of the figure (i.e., perpendicular to the mid-sagittal plane). The prevention or reduction of displacement of the tongue reduces the resistance to airflow in the patient's airway (e.g., in the oropharynx or hypopharynx) by portions of the tongue (e.g., portions of the tongue base). The displacement force may be zero when the patient is awake. For example, the connection between an external anchor (e.g., anchor 118 of FIG. 5) and a tongue anchor (e.g., anchor 104 of FIG. 5) may be removed or disconnected/detached when the patient is awake. Any of the external anchors disclosed herein (e.g., anchor 118 of FIG. 5) may be removed when the patient is awake.

Embodiments of the present invention may be designed and/or placed to produce a clinical effect by a second mechanism discussed in this paragraph. Device 100 itself or the attachment of device 100 to an anchoring region (e.g., a region of the patient's teeth or gums) produces a therapeutic displacement force on the tongue. At least one component of the displacement force is directed along the anterior direction, such that the displacement force causes displacement of a portion of the posterior tongue such that the tongue is displaced more anteriorly than its physiological resting position. In some embodiments herein, device 100 causes displacement of the body of the tongue. The displacement force may be generated using an anatomical region exterior to the tongue. At least one portion of the tongue is displaced in the anterior direction. As shown in FIG. 1E, the displacement force has caused one or more portions of the tongue to rotate about a rotation axis 110 in a counter-clockwise direction. The rotation axis 110 is perpendicular to the plane of the figure. The displacement of the tongue reduces the resistance to airflow in the patient's airway (e.g. in the oropharynx or hypopharynx) by portions of the tongue (e.g. portions of the tongue base). The displacement force may be zero when the patient is awake. For example, the connection between an external anchor (e.g., anchor 118 of FIG. 5) and a tongue anchor (e.g., anchor 104 of FIG. 5) may be removed or disconnected/detached when the patient is awake. Any of the external anchors disclosed herein (e.g., anchor 118 of FIG. 5) may be removed when the patient is awake.

In any of the embodiments herein, the patient may adjust the displacement force or other parameters including, but not limited to: the placement or positioning of one or more device components (e.g., first tongue anchor, second tongue anchor, external anchors, etc.), the amount of displacement(s) (e.g., tension on a tongue elongate member, length of tongue elongate member, force exerted on the tongue by the tongue elongate member, force exerted on the tongue by the external elongate member, etc.), distance by which the tongue can move posteriorly before a therapeutic force starts to act, etc. The adjustment(s) may be done before the patient goes to sleep. In one embodiment, the patient starts the therapy with a lower therapeutic force or less tension on the tongue elongate member. The patient then adjusts one or more parameters of the device such that the force increases gradually over one or more days. The force may be increased until a desired therapeutic effect is obtained and/or the patient has trouble tolerating the device. The force and other parameters of the device embodiments herein may be adjusted multiple times by the patient. One of the key advantages of the embodiments disclosed herein is that the devices can be easily adjusted multiple times by the patient.

Embodiments disclosed herein may exert a displacement force ranging from about N to about 5 N; about 0.2 N to about 3 N; about 1 N to about 2 N; about 0.05 N to about 2.5 N; about 1 N to about 5 N; etc. on one or more portions of the tongue and/or an anchor when the patient is sleeping. Embodiments disclosed herein may exert a displacement force such that the anterior component of the displacement force ranges from about 0.01 N to about 5 N on one or more portions of the tongue and/or an anchor when the patient is sleeping. Embodiments disclosed herein may produce a tension ranging from about 0.01 N to about 5 N within one or more regions of device 100 when the patient is sleeping. Examples of such regions include, but are not limited to one or more of: elongate members 108 and/or elongate members 112 and/or elongate members 114 disclosed herein.

Figure 6:
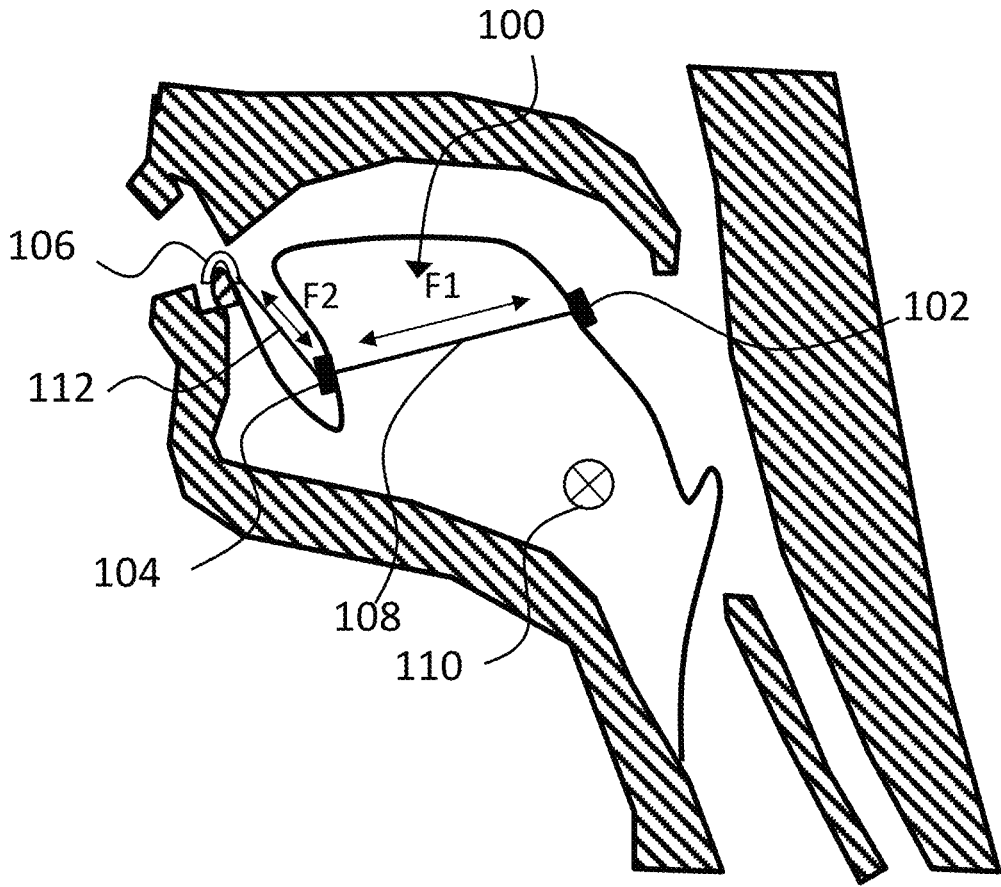
FIG. 6 shows one embodiment of a method of adjusting a displacement force on the tongue.

FIG. 6 shows the step of adjusting the displacement force on the tongue. Such a step of adjusting the displacement force may be used in any of the embodiments disclosed herein. Such adjusting of the displacement force may be performed by adjusting the tension in any of the elongate members disclosed herein. For example, as shown by arrow F1, a length of the tongue elongate member 108, or a length of tongue elongate member 108 between a first tongue anchor 102 and a second tongue anchor 104, may be increased or decreased to adjust displacement of the tongue. Further, for example, as shown by arrow F2, a length of external elongate member 112, or a length of the elongate member 112 that is between the second tongue anchor 104 and the external anchor 106, may be increased or decreased to adjust displacement of the tongue. The displacement force may be adjusted by methods including, but not limited to one or more of: changing the region of the patient's anatomy (e.g., teeth, gums, face, etc.) to which one or more portions (e.g., anchors) of device 100 attach, changing one or more physical parameters (e.g., length, stiffness, flexibility, elasticity, etc.) of any component (examples include, but are not limited to: anchors, elongate members), changing the location and/or orientation of any component (examples include, but are not limited to: anchors, elongate members), etc.

In some embodiments, adjusting the displacement force includes, but is not limited to: increasing or reducing a physiological effect of the invention, reducing a force on the tongue, increasing a force on the tongue, reducing a tension between the first and second tongue anchors, increasing a tension between the first and second tongue anchors, increasing an anterior displacement of the tongue, reducing an anterior displacement of the tongue, increasing a posterior displacement of the tongue, reducing a posterior displacement of the tongue, reducing one or more side-effects, reducing an abnormal sensation (e.g., pain/discomfort, excessive pulling sensation, excessive saliva production, etc.) felt by the patient, and producing a sensation (e.g., slight discomfort, pulling sensation, etc.) felt by the patient when the patient's tongue loses muscle tone. The step of adjusting the displacement force may be performed multiple times in the same patient. The step of adjusting the displacement force may be performed by a medical professional or by the patient.

In one such embodiment, the displacement force is increased to increase the displacement of the tongue in the anterior direction to increase the therapeutic effect of the invention. In another such embodiment, the displacement force is decreased to decrease the displacement of the tongue in the anterior direction to reduce the pain/discomfort felt by the patient.

Figure 7:
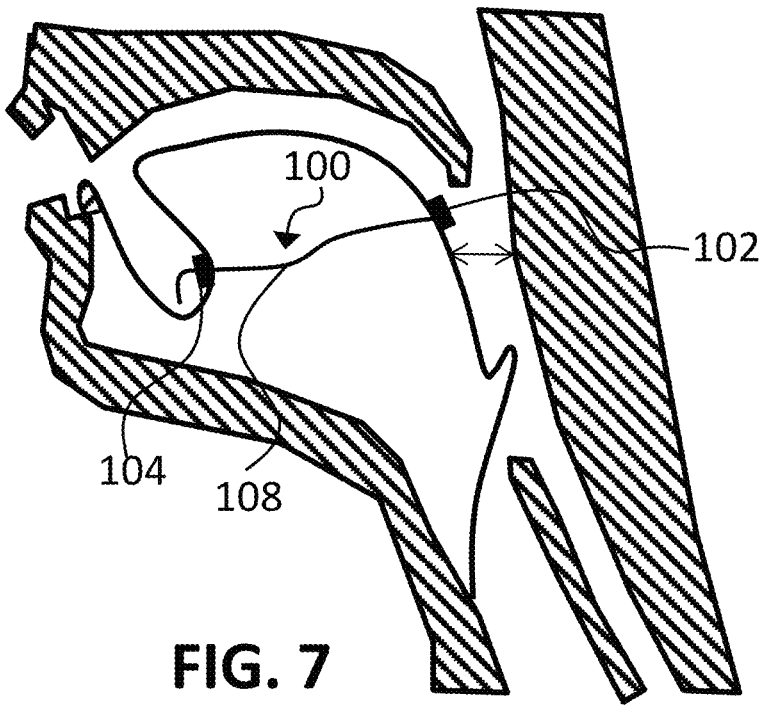
FIG. 7 shows one embodiment of an elongate member reversibly attached to a second tongue anchor.
Figure 8:
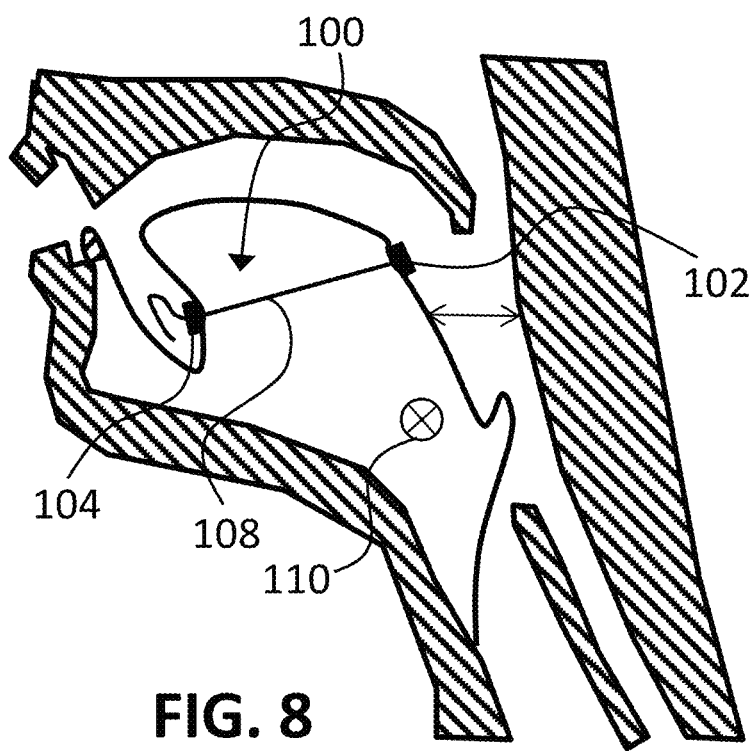
FIG. 8 shows one embodiment of an elongate member in a sliding arrangement relative to a second tongue anchor.

FIGS. 7-8 show a section through a human head showing an embodiment of the present invention comprising two anchors wherein the distance between the two anchors is adjusted to adjust the displacement force. In one such embodiment, as shown in FIG. 7, elongate member 108 is reversibly attached to second tongue anchor 104, such that second tongue anchor 104 can be attached and unattached from elongate member 108 to adjust a displacement force on the tongue. In another such embodiment, as shown in FIG. 8, tongue elongate member 108 is in a sliding arrangement relative to second anchor 104. For example, the second tongue anchor 104 may comprise a slide lock clasp, an adjustable slider clasp, a toggle spring stop, magnetic clasp, barrel clasp, clasp closure, clamp, spring coil, etc. Such adjustable designs may also be used for other embodiments disclosed herein including, but not limited to the embodiments shown in FIGS. 50-51.

Figure 9:
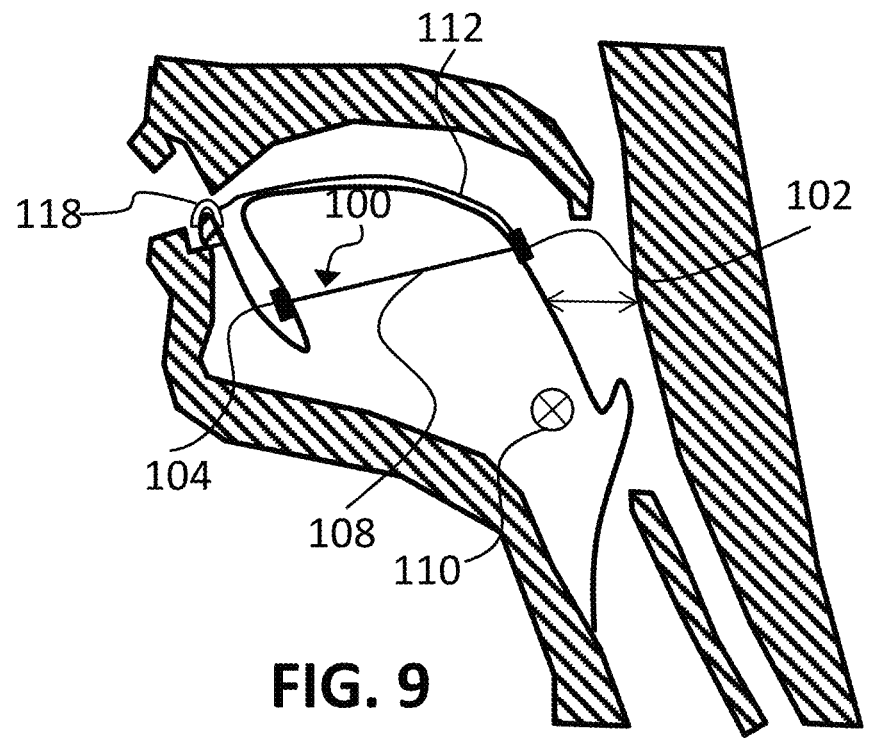
FIG. 9 shows one embodiment of an external elongate member reversibly attached or in sliding arrangement relative to a first tongue anchor.

In some embodiments, as shown in FIG. 9, an external or dorsal elongate member 112, coupled to external anchor 118, extends from the first tongue anchor 102, as opposed to the second tongue anchor 104. Tongue elongate member 108 extends between first tongue anchor 102 and second tongue anchor 104, but in this embodiment, the first tongue anchor 102 is either reversibly attached or slidably attached to tongue elongate member 108, as described above in FIGS. 7-8 for second tongue anchor 104.

Figure 10:
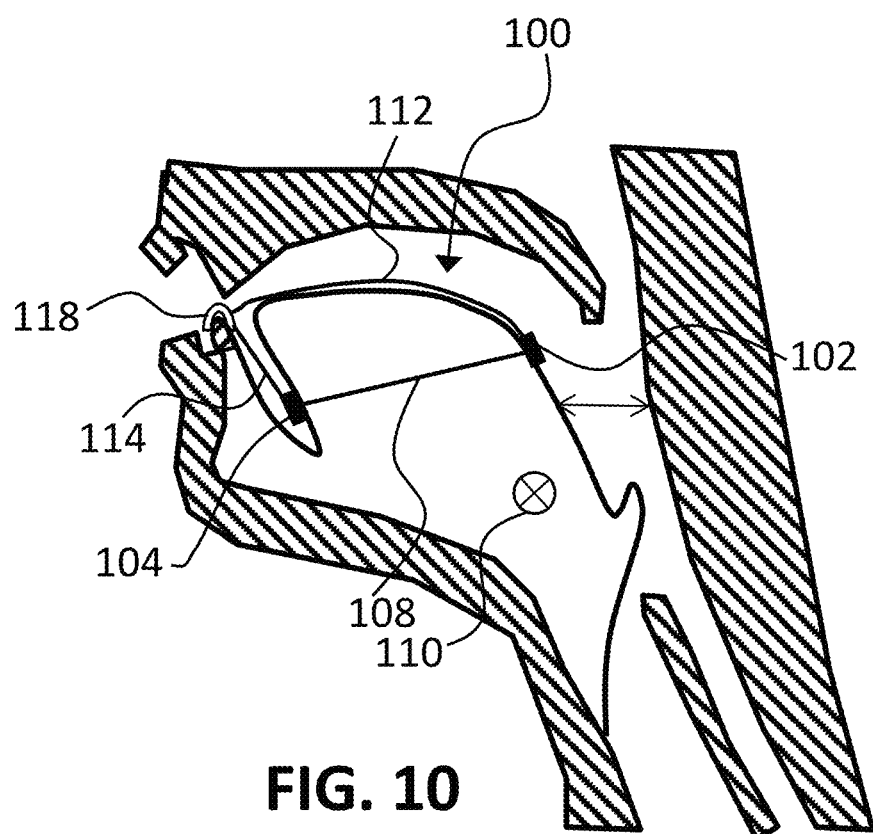
FIG. 10 shows one embodiment of an external elongate member extending from a second tongue anchor and a dorsal elongate member extending from a first tongue anchor, both of which are attached to an external anchor.

Further, as shown in FIG. 10, both a first tongue anchor 102 and a second tongue anchor 104 may interact with an external anchor 118. In such an embodiment, a dorsal elongate member 112 extends from the first tongue anchor 102 and a ventral or external elongate member 114 extends from the second tongue anchor 104. shows a section through a human head showing an embodiment of the present invention comprising a first tongue anchor, a second tongue anchor, and an external anchor. In this embodiment, external anchor 118 anchors to a region on the teeth of the patient. In this embodiment, second anchor 104 is connected to external anchor 118 through a third elongate member 114.

Figure 11:
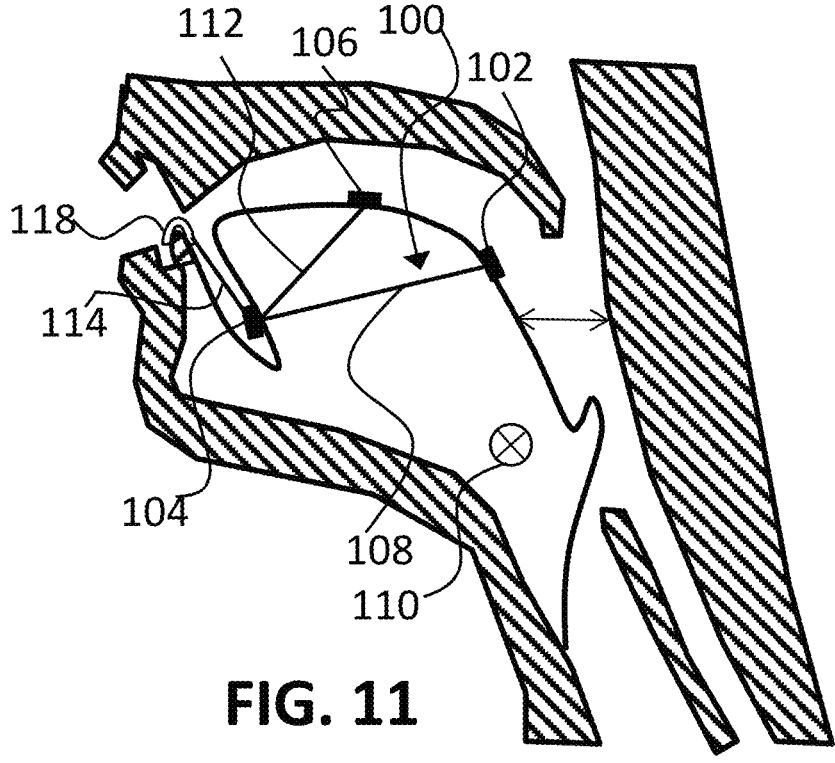
FIG. 11 shows one embodiment of a device comprising two substantially dorsally positioned tongue anchors and one substantially ventrally positioned tongue anchor.

In still another embodiment, as shown in FIG. 11, a first tongue anchor 102 is positioned substantially dorsally on the tongue and a second tongue anchor 104 is positioned substantially ventrally on the tongue, as shown elsewhere herein; however, in this embodiment, a third tongue anchor 106 is also positioned substantially dorsally on the tongue, but more anteriorly than first tongue anchor 102. As such, the tongue is engaged at three points 102, 104, and 106 and a displacement force is applied along a lower elongate member 108 and an upper elongate member 112, each of which extend through at least a portion of the tongue.

Further one or both elongate members 108, 112 may be adjustable through, via, or at second or ventral tongue anchor 104. External elongate member 114 extends from second tongue anchor 104 and engages with external anchor 118.

Figure 12:
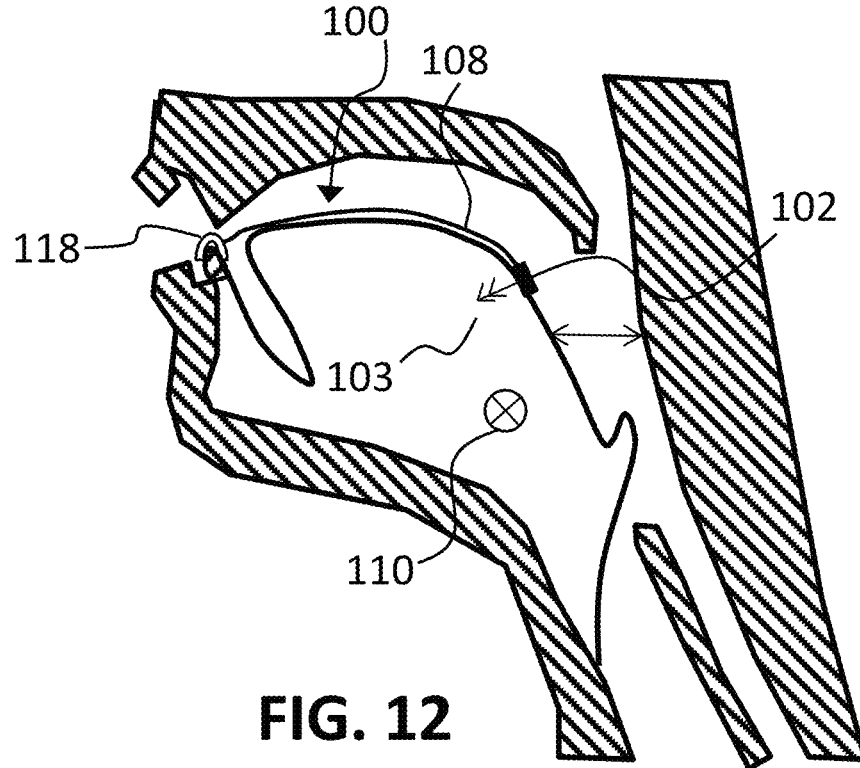
FIG. 12 shows one embodiment of a device comprising a first or dorsal tongue anchor comprising one or more tissue penetrating elements.

FIG. 12 shows a section through a human head showing an embodiment of the present invention comprising a dorsal tongue anchor and an external anchor wherein at least one portion of the dorsal tongue anchor is embedded into the tongue. Dorsal tongue anchor 102 comprises one or more tissue penetrating elements regions 103, examples of which include, but are not limited to: sharp tips, barbs, bent or curved regions, hooks, etc. The one or more tissue penetrating elements or regions 103 penetrate the tongue and anchor dorsal tongue anchor 102 to a region of the tongue, for example a dorsal region of the tongue.

Figure 13:
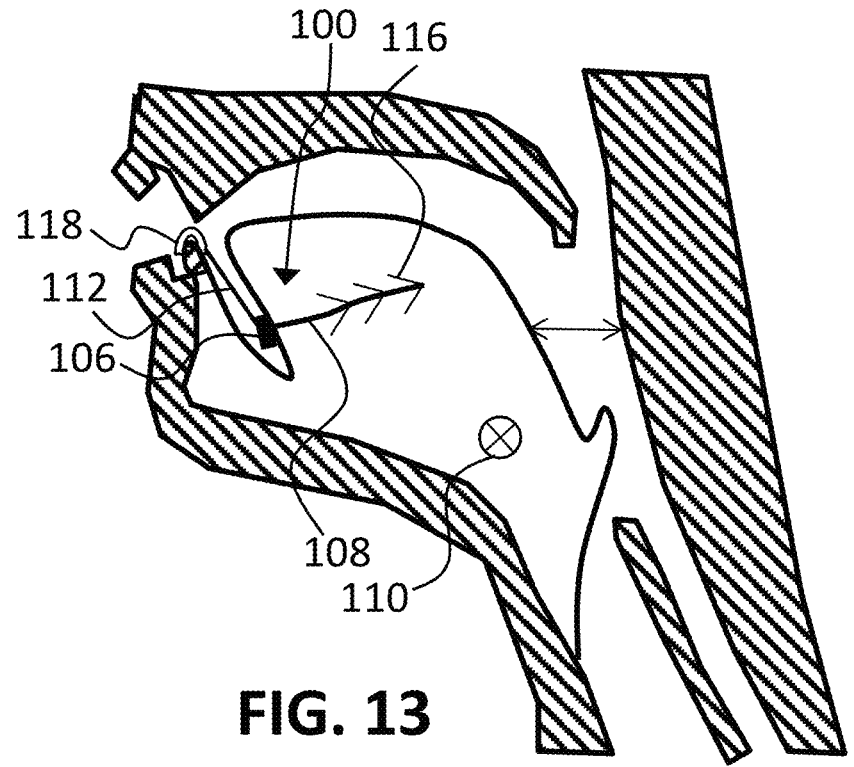
FIG. 13 shows one embodiment of a device comprising a second or ventral tongue anchor comprising one or more tissue penetrating elements.

FIG. 13 shows a section through a human head showing an embodiment of the present invention comprising a ventral tongue anchor 106 with one or more tissue penetrating elements 116 and an external anchor 118. Ventral anchor 106 is coupled to external anchor 118 via external elongate member 112, as described elsewhere herein. Ventral anchor 106 includes one or more tissue penetrating elements 116, examples of which include, but are not limited to: sharp tips, barbs, bent or curved regions, hooks, etc. The one or more tissue penetrating elements 116 embed into the tongue and anchor ventral anchor 106 to a region of the tongue, for example a ventral region of the tongue.

Figure 14:
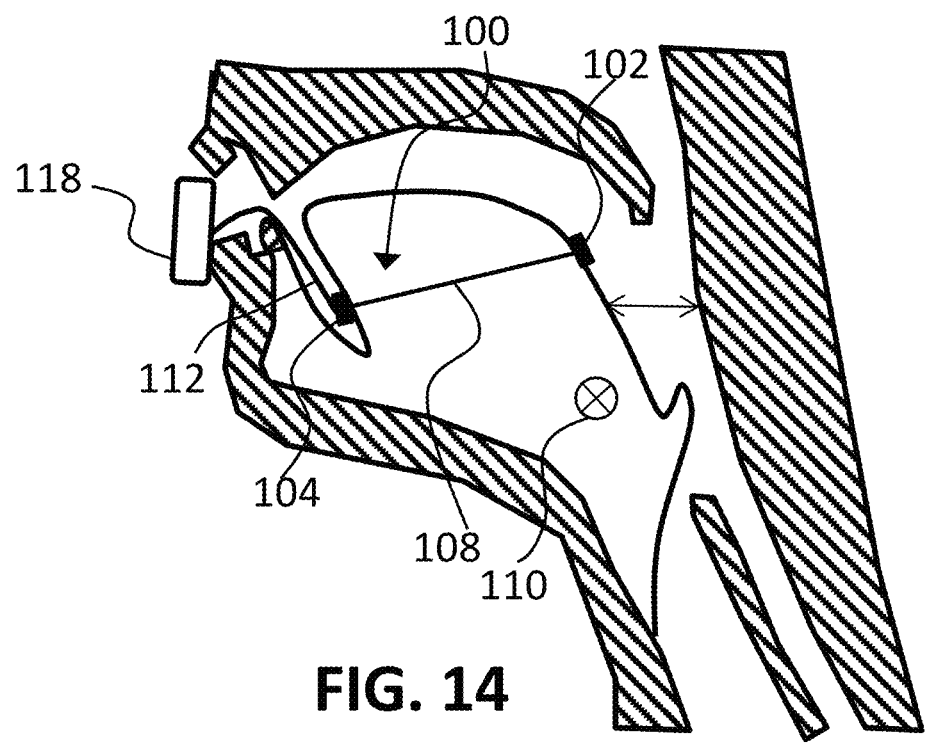
FIG. 14 shows one embodiment of a device comprising an external anchor that attaches to an external fixture.

FIG. 14 shows a section through a human head showing an embodiment of the present invention comprising a first or dorsal tongue anchor, a second or ventral tongue anchor, and an external anchor located outside the mouth of the patient. As shown in FIG. 14, examples of external anchor 118 include, but are not limited to: headgear; facemasks; attachments attached to the patient's head using mechanisms such as straps, adhesives, clips, bands, hooks, etc.; harnesses; head straps; and caps. In one such embodiment, external anchor 118 is similar to an anesthesia mask harness that is attached to the patient's head using one or more flexible and/or elastic straps. Further, as described elsewhere herein, tongue elongate member 108 connects first tongue anchor 102 to second tongue anchor 104 and second tongue anchor is connected to external anchor via external elongate member 112.

Figure 15:
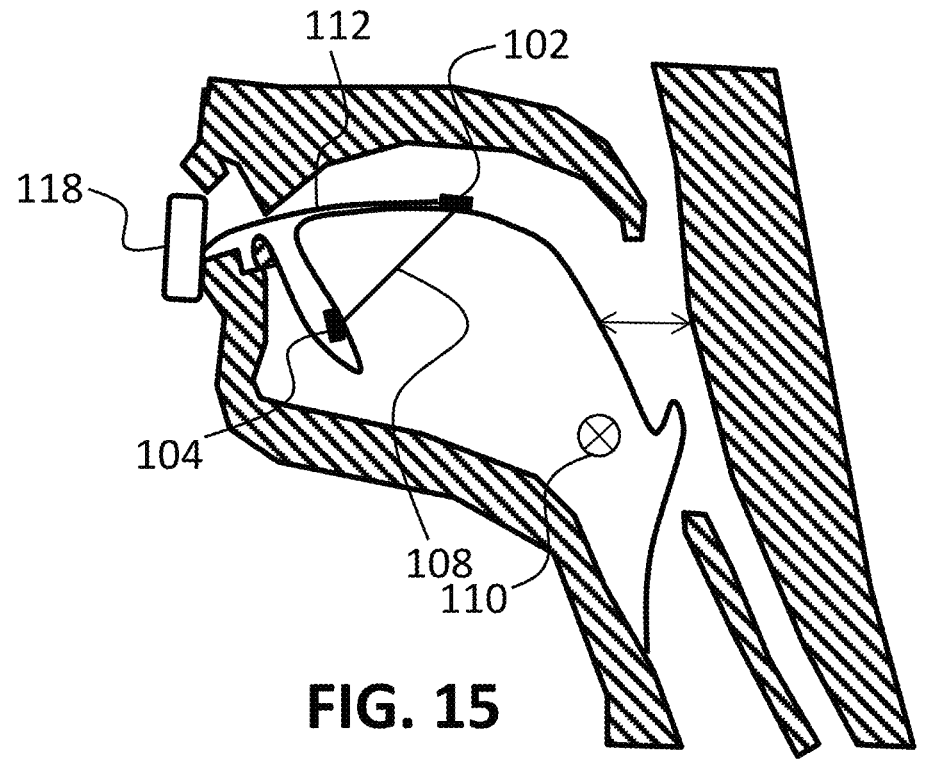
FIG. 15 shows another embodiment of a device comprising an external anchor that attaches to an external fixture.

FIG. 15 shows a section through a human head showing another embodiment of the present invention comprising a first or dorsal tongue anchor 102, a second or ventral tongue anchor 104, and an external anchor located outside the mouth of the patient, similar to that already described with respect to FIG. 14. In this embodiment, dorsal tongue anchor 102 is coupled to external anchor 118 via dorsal or external elongate member 112, as shown and described in FIG. 9.

Figure 16:
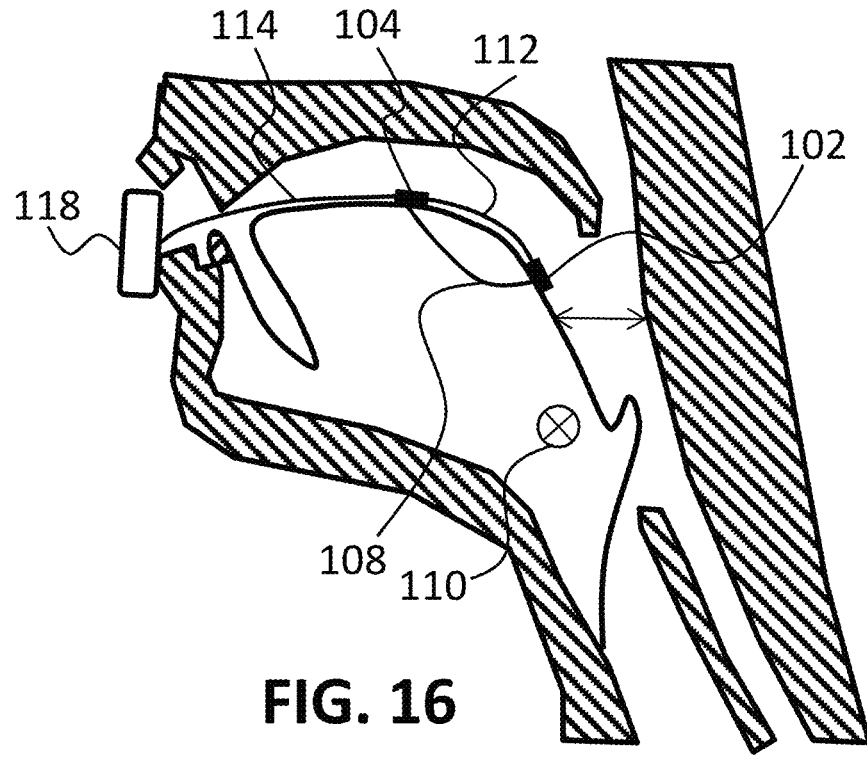
FIG. 16 shows another embodiment of a device comprising an external anchor that attaches to an external fixture.

FIG. 16 shows a section through a human head showing another embodiment of the present invention comprising a first dorsal tongue anchor 102, a second dorsal tongue anchor 104, and an external anchor 118 located outside the mouth of the patient, as described in FIG. 14. First dorsal tongue anchor 102 is positioned more posteriorly than second dorsal tongue anchor 104 or, said another way, second dorsal tongue anchor 104 is positioned more anteriorly than first dorsal tongue anchor 102. First elongate member 112 couples the first 102 and second 104 anchors and elongate member 114 couples the second tongue anchor to external anchor 118. As described elsewhere herein, first and second elongate members 112, 114 form a single elongate member that passes through or interacts with each anchor or they may be separate elongate members.

Figure 17:
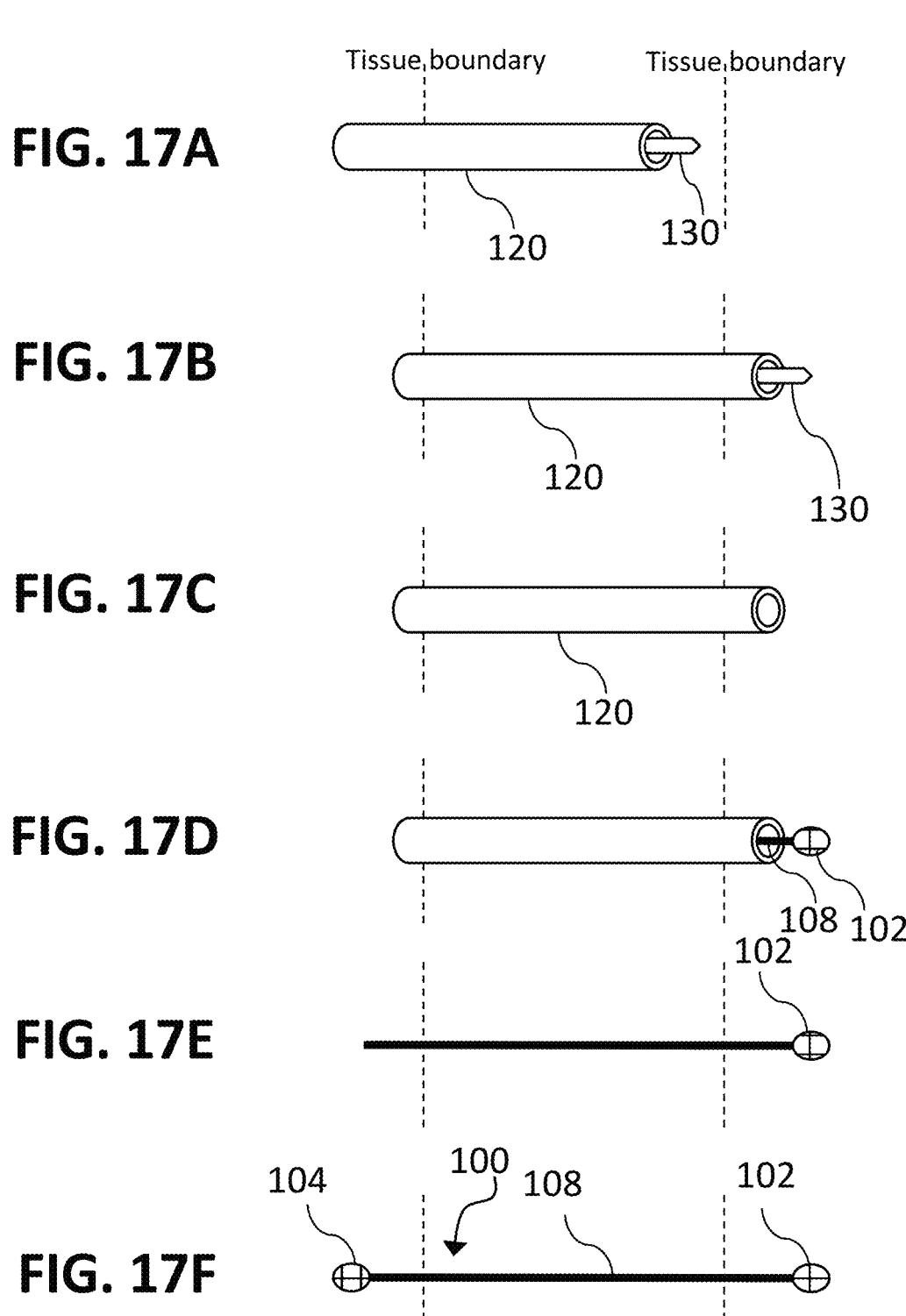
FIGS. 17A-17F show various steps of a method of positioning an elongate member through a tissue.

FIGS. 17A-17F show one embodiment of a method of placing device 100 across tissue. In FIG. 17A, a combination of penetrating element 120 and stylet 130 is used to pierce a tissue boundary. For example, a tissue boundary may include a surface of a tongue, a dorsal surface of a tongue, a ventral surface of a tongue, or other portion of a tongue. In other embodiments, tissue boundary may include a surface of an organ that needs to be retracted, for example to move it or displace it from a surgical field. In FIG. 17B, the combination of penetrating element 120 and stylet 130 is advanced such that the distal tip of penetrating element 120 emerges out of the tissue through another tissue boundary. In FIG. 17C, stylet 130 is removed without removing penetrating element 120. In FIG. 17D, first anchor 102 connected to an elongate member 108 is advanced through a lumen defined by penetrating element 120. In FIG. 17E, penetrating element 120 is removed leaving behind first anchor 102 connected to elongate member 108. In FIG. 17F, second anchor 104 is connected to elongate member 108 creating device 100. Although the above steps are described sequentially according to the figures, one of skill in the art will appreciate that the steps may be executed in any sequence without departing from the original scope or intent of this disclosure.

In this embodiment, a combination of penetrating element 120 and stylet 130 are used together to penetrate tissue. In other embodiments, penetrating elements, including, but are not limited to: laser emitting elements, mechanical members with a sharp tip, radiofrequency or microwave emitting elements, heating elements, elements loaded using a spring or other mechanical component, and a part of device 100, are used to penetrate one or more tissue regions.

Figure 18:
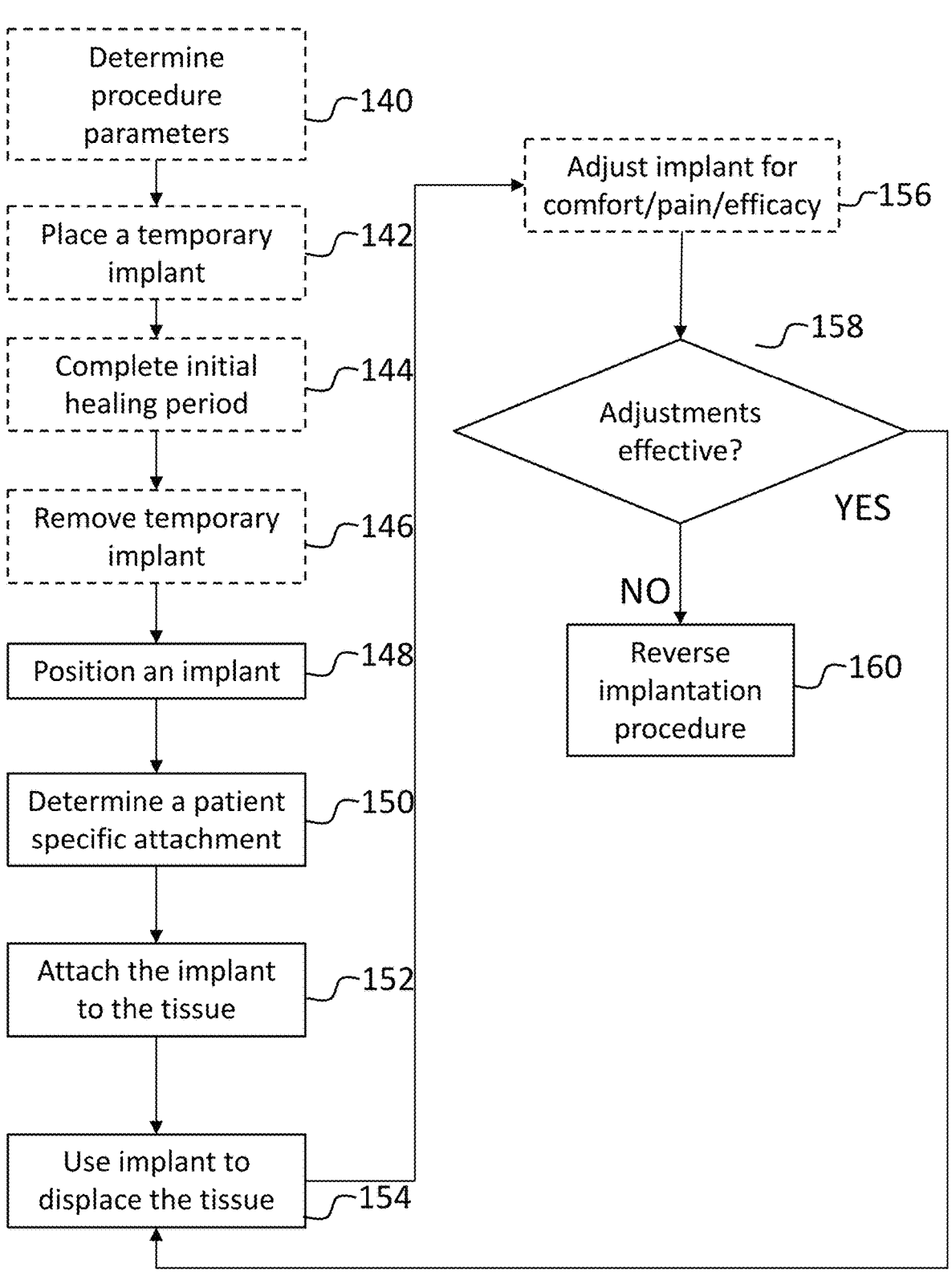
FIG. 18 shows one embodiment of a method of positioning or implanting a device.

FIG. 18 shows an embodiment of a method of the present invention wherein device 100 comprises a long-term (e.g., permanent, placed for more than a week, etc.) implant. At optional step 140, a healthcare provider (e.g., a surgeon, a dentist, physician, etc.) determines one or more parameters of the procedure. Examples of such parameters include, but are not limited to: device type (including size) or number of components of device 100, location of placement of one or more implants, direction of one or more implants, degree of restriction and/or displacement of the tissue, direction and/or magnitude of forces to be applied to the tongue, etc. At optional step 142, a temporary implant is placed into the tissue. In one embodiment, the temporary implant is placed using one or more steps shown in FIGS. 17A-17F. At optional step 144, an initial healing period is completed. The healing period may range from 2-3 days to about a month. During the healing period, one or more of: swelling, inflammation, and pain may reduce. At optional step 146, the temporary implant is removed. At step 148, an implant (e.g., a long-term implant but could also be a short-term implant) is positioned in or relative to a tissue of the patient. Examples of such implants includes any of the implants disclosed elsewhere herein. At step 150, a patient specific attachment (e.g., an external anchor 118) is determined (e.g., a face mask, a dental attachment, gum attachment, a retainer attachment, a mouth guard attachment, etc.). Alternatively, a desired attachment may be selected for the patient. At step 152, attach the implant to the determined structure (e.g., face mask, teeth, gums, retainer, etc.). The device functions or is used to displace the tissue, as disclosed elsewhere herein. At optional step 156, the effect of the device is adjusted for one or more of: comfort/pain, pulling sensation, side effects, and/or efficacy. At step 158, a determination is made whether the adjustments to the implant were effective and/or are obtaining the desired clinical effect. When the patient is satisfied, the patient continues to use the device and the method returns to step 154. When the adjustments are not effective at step 158, the implantation procedure is reversed at step 160. A major advantage of the minimally invasive methods and devices disclosed herein is that the entire clinical procedure can be reversed without causing long term or permanent changes to the patient's anatomy. Although the above steps are described sequentially according to the figures, one of skill in the art will appreciate that the steps may be executed in any sequence without departing from the original scope or intent of this disclosure.

Figure 19:
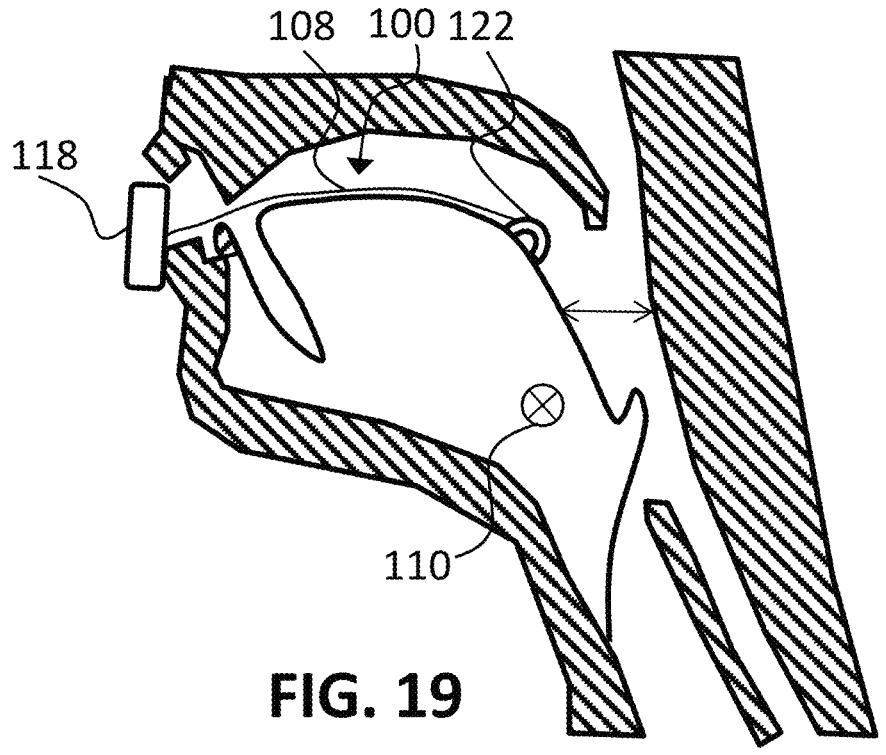
FIG. 19 shows one embodiment of a device comprising a surface anchor.

FIG. 19 shows a section through a human head showing an embodiment of the invention comprising a tongue surface anchor and an external anchor. In one method embodiment, temporary placement of devices 100 (e.g., those comprising a tissue surface anchor) is used to determine one or more of: patient tolerability to devices 100; resolution of symptoms; dimensions and/or type of one or more elements (e.g., anchors, elongate members, etc.) of devices 100; anatomical location and number of one or more implants, etc. This information, in turn, may be used to: decide the suitability of patients to more invasive devices 100 (e.g., those that involve tissue penetration); decide the aspects of subsequent procedures, e.g., placement of one or more anchors, type of anchors and elongate members, etc.

In one embodiment, surface anchor 122 is a suction anchor. Examples of suction anchors 122 include, but are not limited to: suction anchors 122 that are directly attached to a vacuum generating element; suction anchors 122 that are indirectly attached to a vacuum generating element; and suction anchors that have an integrated vacuum generating element. A suction anchor 122 may be attached to the vacuum generating element through one or more of: tethers, wires, tubes, pistons, elements comprising a displaceable portion that generates a vacuum, etc. Examples of vacuum generating elements include, but are not limited to: balloon structures, bulbs, vacuum and other pumps, syringes, elements comprising a displaceable portion that generates a vacuum, etc. In another embodiment, surface anchor 122 is an anchor attachable to a region of the tongue using glue. One or more portions of suction anchors may be made of rigid materials, examples of which include, but are not limited to: metals, plastics, polymers (e.g., silicone), rigid rubber materials, etc. One or more portions of suction anchors may be made of flexible materials, examples of which include, but are not limited to: metals, plastics, polymers (e.g., silicone), rubber materials, foams, gels, elastic materials, etc. To effectively maintain vacuum, one or more flexible materials such as foams and hydrocolloids may be used. Such materials may be a part of surface anchor 122 or a separate element. As shown and described elsewhere herein, surface anchor 122 may be coupled to elongate member 108, which is coupled to external anchor 118, for example anchored to a bodily portion (e.g., teeth, gums, etc.) or to a fixture (e.g., retainer, head gear, mask, etc.).

Any of the elongate members disclosed herein may be made of an elastic material. In such embodiments, the elastic elongate member(s) perform one or more actions including, but not limited to: allowing easier use of device 100, preventing excessive forces on that anatomy, maintaining a force on the anatomy, etc.

Figure 20:
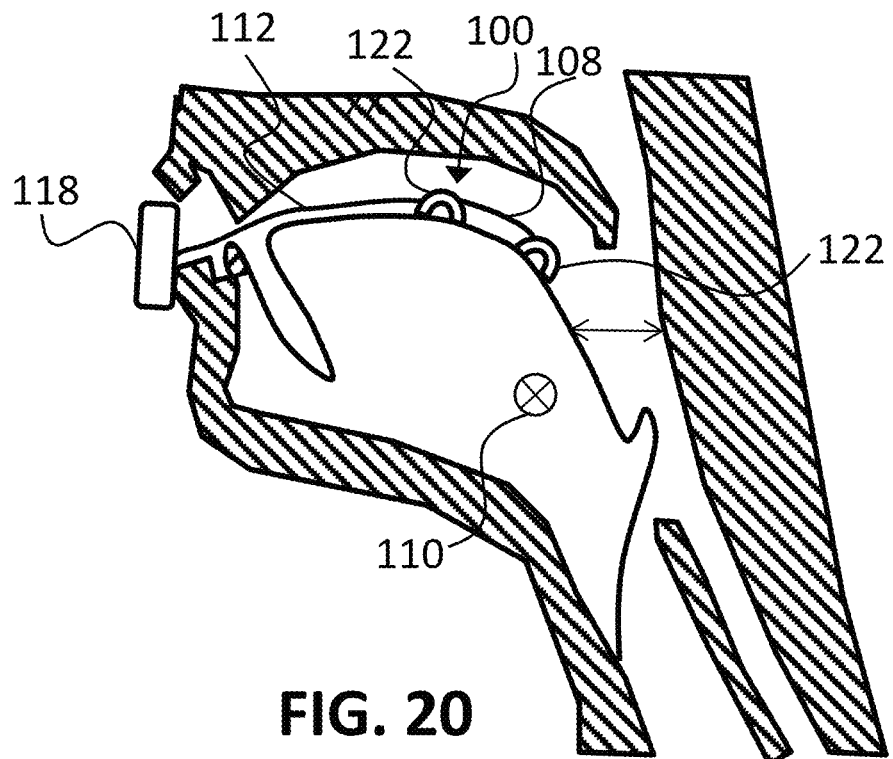
FIG. 20 shows another embodiment of a device comprising a surface anchor.

FIG. 20 shows a section through a human head showing an embodiment of the invention comprising two surface anchors (e.g., suction anchors) and an external anchor. In such an embodiment, a second surface anchor 122 may be positioned on the tissue more anteriorly than a first surface anchor 108. Said another way, a first surface anchor 108 may be positioned more posteriorly than a second surface anchor 122. Second surface anchor 122 may be coupled to an elongate member 122, which is coupled to external anchor 118, as described elsewhere herein.

Figure 21:
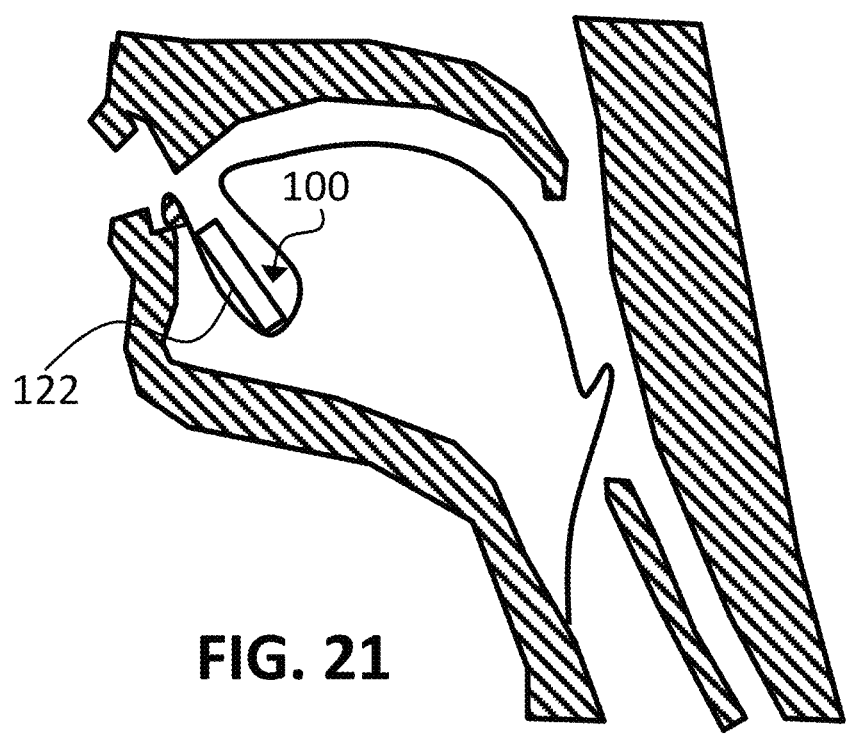
FIG. 21 shows another embodiment of a device comprising a surface anchor in an inactive configuration.
Figure 22:
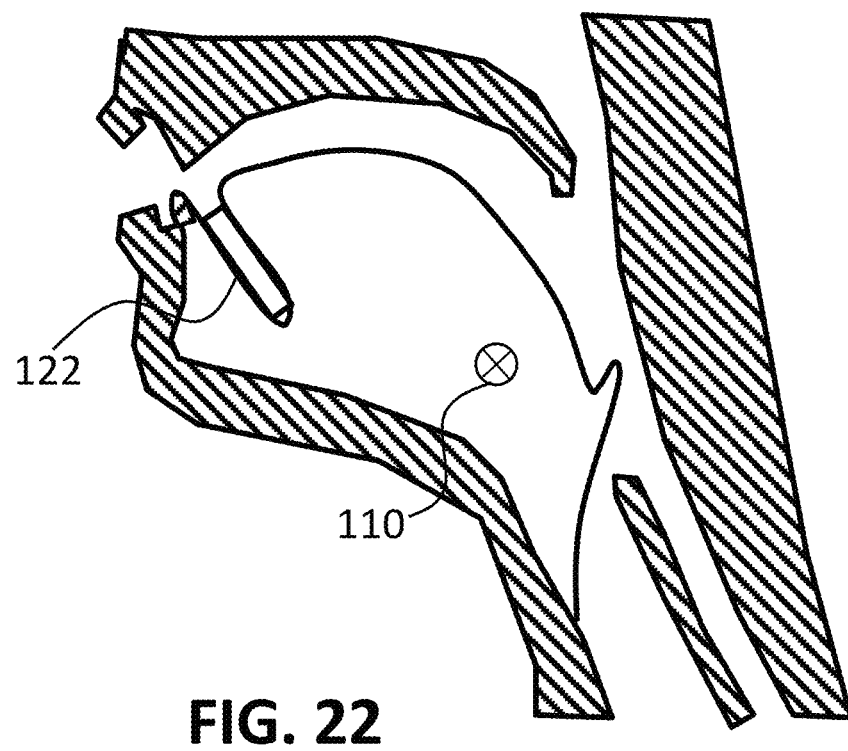
FIG. 22 shows another embodiment of a device comprising a surface anchor in an active configuration.

FIGS. 21-22 show a section through a human head showing an embodiment of a method of the present invention that uses a sub-lingual surface anchor 122 (e.g., a suction anchor). As shown in FIG. 21, a surface anchor 122 is positioned sub-lingually, between a floor of the mouth and a ventral surface of the tongue. FIG. 21 shows the inactive, no suction applied, configuration. In FIG. 22, suction is applied, creating an active configuration, to the surface anchor causing the tongue to move forward and contact the surface anchor 122.

Figure 23:
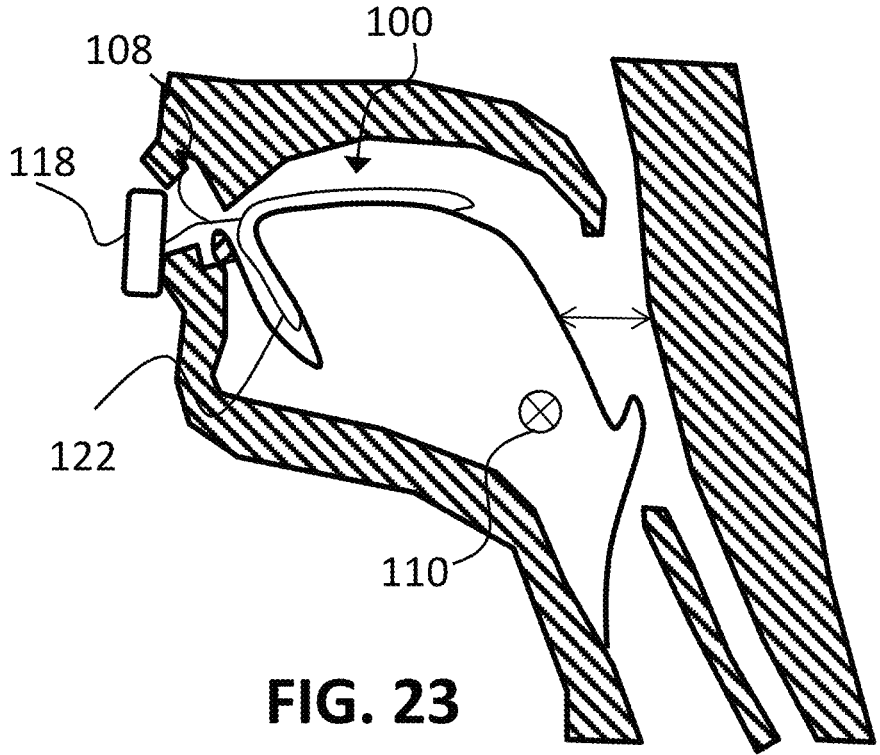
FIG. 23 shows another embodiment of a device comprising a surface anchor.

FIG. 23 shows a section through a human head showing another embodiment of the invention comprising a surface anchor 122 (e.g., a suction anchor) and an external anchor 118. In this embodiment, the surface anchor 122 is attached to the tip of the tongue. As shown in FIG. 23, surface anchor 122 contacts and interacts with at least a ventral portion of the tongue and at least a dorsal portion of the tongue. When vacuum is applied to surface anchor 122, surface anchor 122 securely holds the tongue and the tongue is displaced relative to the posterior wall of the pharynx by external anchor 118 that is coupled to surface anchor 122. External anchor 118 may couple to surface anchor at a tip of the tongue, on a ventral surface of the tongue, or on a dorsal surface of the tongue.

Figure 24:
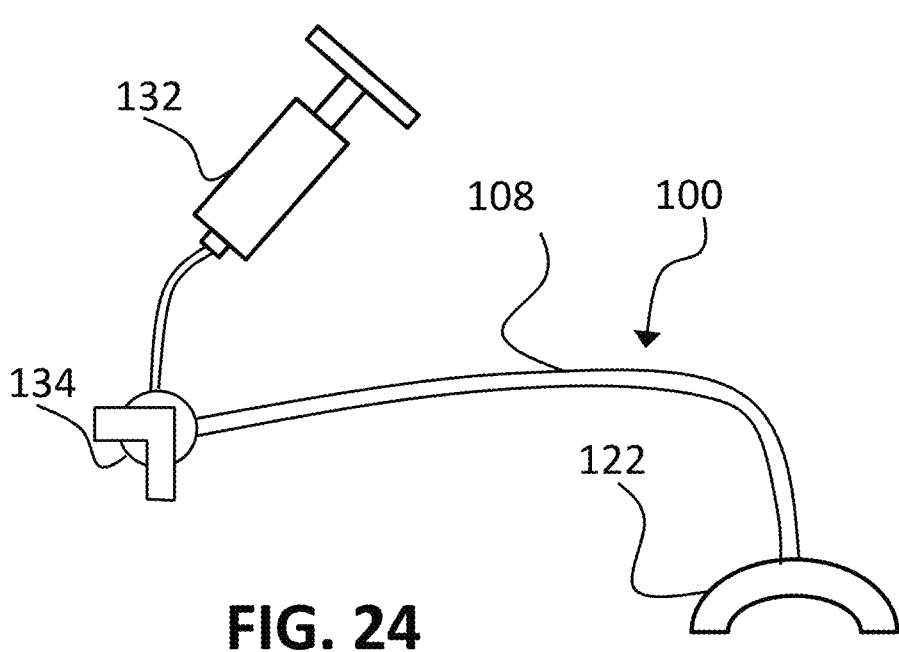
FIG. 24 shows another embodiment of a device comprising a surface anchor.

FIG. 24 shows a device embodiment of the present invention comprising a suction anchor than can be reversibly attached to a tongue. In FIG. 24, suction anchor 122 is connected to a syringe 132 through a first elongate member 108. First elongate member 108 is in fluid communication with syringe 132. For example, elongate member 108 may define a lumen therethrough that is in fluid communication with a chamber defined by syringe 132. Syringe 132 acts as a vacuum generating element. This embodiment further comprises a valve 134 (e.g., a stopcock, a self-sealing valve, etc.) that can be used to allow or block a fluid communication between syringe 132 and suction anchor 122. A user can keep valve 134 open and create a vacuum using syringe 132. Thereafter, the user can close valve 134 and remove syringe 132. In embodiments of self-sealing valves, the valve may be designed such that it opens when connected to a specific device (e.g., a syringe) and seals it self when the device is removed. Any of the valves disclosed in any embodiment herein may be a check valve that controls the flow direction of air or other fluids. Any of the valves disclosed herein may be single-configuration check valves designed to prevent back flow in only one direction. The valves may comprise designs including, but not limited to: diaphragm valves, sleeve valves, flap valves, ball check valves, etc. Such valves may comprise diaphragms or sleeves made of materials such as silicone or rubber housed in a polymer housing. The length and other dimensions of elongate member 108 may be such that suction anchor 122 is allowed to extend the tissue to a target displaced position while preventing the tongue from falling too deep into the patient's throat and obstructing the airflow.

Figure 25A:
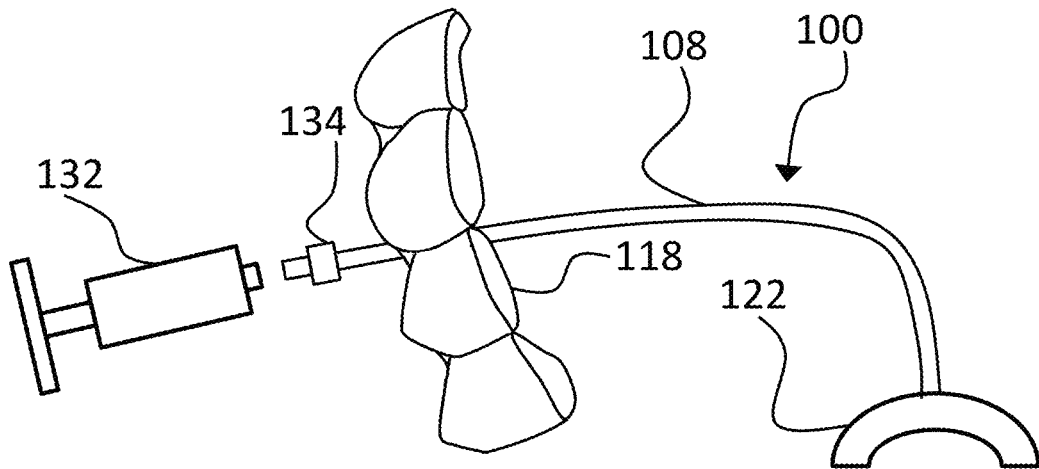
FIG. 25A shows another embodiment of a device comprising a surface anchor.

FIG. 25A shows an integrated device embodiment of the present invention wherein two anchors are connected to each other through an elongate member. In the embodiment shown, one of the anchors is a suction anchor 122 than can be reversibly attached to a tongue. Suction anchor 122 is connected to an external anchor 118 through a first elongate member 108. In one embodiment, suction anchor 122 is permanently connected to an external anchor 118 through a first elongate member 108. In another embodiment, suction anchor 122 is reversibly connected to an external anchor 118 through a first elongate member 108. The length of first elongate member 108 between suction anchor 122 and external anchor 118 may be adjustable. In method embodiments using such a design, the length of first elongate member 108 between suction anchor 122 and external anchor 118 may be adjusted based on parameters disclosed elsewhere in this specification. In the embodiment shown in FIG. 25A, external anchor 118 is a dental anchor. One embodiment of vacuum generation is shown in FIG. 25A. Vacuum is generated using a syringe 132 that is in fluid communication with suction anchor 122. A valve 134 (e.g., a stopcock, a self-sealing valve, etc.) may be provided that allows or blocks a fluid communication between syringe 132 and suction anchor 122. Valve 134 may be opened or kept closed to create/remove or maintain a vacuum. Valve 134 may be a self-sealing valve that opens when connected to a specific device (e.g., a syringe) and seals itself when the device is removed. The length and other dimensions of elongate member 108 may be such that suction anchor 122 is allowed to extend the tissue to a target displaced position while preventing the tongue from falling too deep into the patient's throat and obstructing the airflow.

FIGS. 25B and 25C show two configurations of an embodiment of a suction anchor comprising a soft or deformable region. Any of the suction anchors 122 disclosed herein may comprise one or more regions that are soft enough to deform on application of a vacuum. For example, a tissue contacting region of suction anchor 122 may be made of a material that has a Shore A hardness less than about 60 or a Shore 00 hardness less than about 90. In a particular embodiment, a tissue contacting region of suction anchor 122 is made of a material that has a Shore A hardness less than about 20 or a Shore 00 hardness less than about 70. In a particular embodiment, a tissue contacting region of suction anchor 122 is made of a material that has a Shore 00 hardness less than about 60. The non-tissue contacting regions of any suction anchors 122 disclosed herein may be made of harder or stiffer materials. Examples of materials that may be used to manufacture suction anchors 122 disclosed herein are mentioned elsewhere in this specification. FIG. 25B shows the shape of a soft suction anchor 122 before applying a vacuum. On applying a vacuum, the shape of suction anchor 122 changes as shown in FIG. 25C. As shown in FIG. 25C, the height H of suction anchor 122 reduces on application of a vacuum. Further, the width W of suction anchor 122 increases on application of a vacuum. Thus, on application of a vacuum, suction anchor 122 deforms and mechanically adjusts to the tongue surface instead of the tongue alone deforming into a shape that fits into a suction anchor 122. This design increases the comfort of the patient when using device 100 and also allows a better retention of a vacuum during use. For example, a height H1 between a first configuration (FIG. 25B) and a height H2 of a second configuration (FIG. 25C) may decrease by about 0.1×; about 0.5×; about 1×; about 2×; about 3×; about 4×; between about 0.5× to about 2×; about 1× to about 3×; etc. Further for example, a width W1 between a first conformation (FIG. 25B) and a width W2 of a second conformation (FIG. 25C) may increase by about 0.05×, about 0.1×, about 0.2×; about 0.5×; about 1×; about 2×; about 3×; about 4×; between about 0.5× to about 2×; about 1× to about 3×; etc. As shown in FIG. 25C, in the deployed configuration of suction anchor 122, an angle 131 between the wall of suction anchor 122 at the perimeter of the device (or at the tissue contacting region of suction anchor 122) and the wall at a non-tissue contacting surface of the device may be greater than about 90 degrees. As show in the embodiment, angle 131 may be greater than about 130 degrees. For example, angle about 131 may be greater than about 135 degrees or even greater than about 140 degrees. The perimeter may be at an interface between a first tissue contacting side of the device and a second non-tissue contacting side of the device.

Any of the anchors disclosed herein (including, but not limited to anchor 102 and anchor 104) may be manufactured using soft materials that deform during use. For example, anchor 102 and/or anchor 104 of FIG. 5 may deform when a force is applied in the step shown in FIG. 5. Such soft anchors are especially useful to increase the comfort of the patient e.g., during sleep. Further, soft anchors may be used to divide a force over a large tissue area, essentially reducing the pressure on a tissue area, which in turn helps to prevent and/or reduce one or more of: pain/discomfort, sensation of a foreign object, tissue necrosis, reduction in tissue perfusion, tissue erosion, and/or migration of device 100 components.

Any of the suction anchors may be detached from the tongue by temporarily increasing the pressure inside the suction anchor to reduce the vacuum inside the suction anchor. This may be achieved, for example, by applying pressure (e.g., using a finger) to a suction anchor to change the shape of the anchor, which in turn reduces the vacuum inside the anchor.

Any of the suction anchors 122 disclosed herein may be designed and used with a vacuum sufficient to distort tongue tissue and/or suction anchor 122 such that a portion of tongue tissue comes into physical contact with an inner portion of suction anchor 122. One example is shown in FIG. 25C, wherein the region where a portion of tongue tissue comes into physical contact with an inner portion of suction anchor 122 is marked with a dashed circle 129. Any of the suction anchors 122 disclosed herein may be designed such that the tissue contacting region of the suction anchor 122 is roughly planar such that the plane of the tissue contacting region is parallel to the plane of the contacted tissue. Any of the suction anchors 122 disclosed herein may be designed such that the region of contact between the suction anchor 122 and the tissue increases as the amount of applied vacuum increases. Such a design allows a better retention of a vacuum during use.

Figure 26:
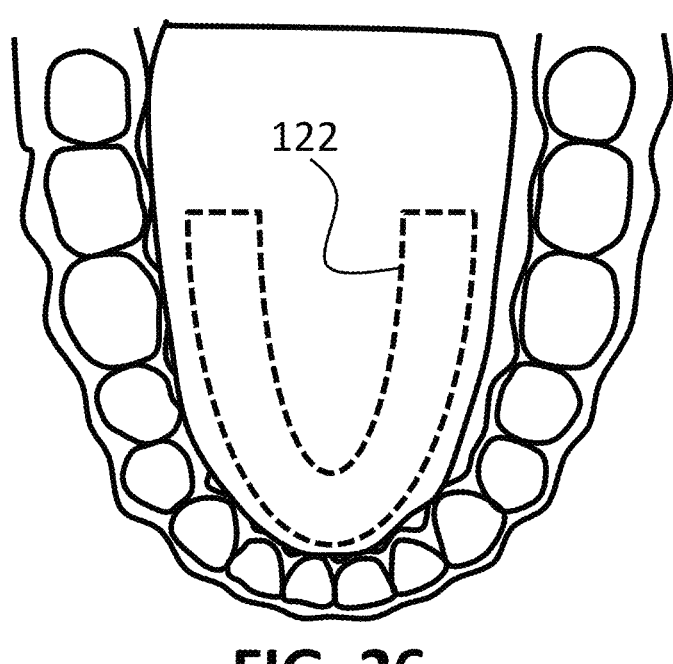
FIG. 26 shows one embodiment of a device comprising a sub-lingual anchor.
Figure 27:
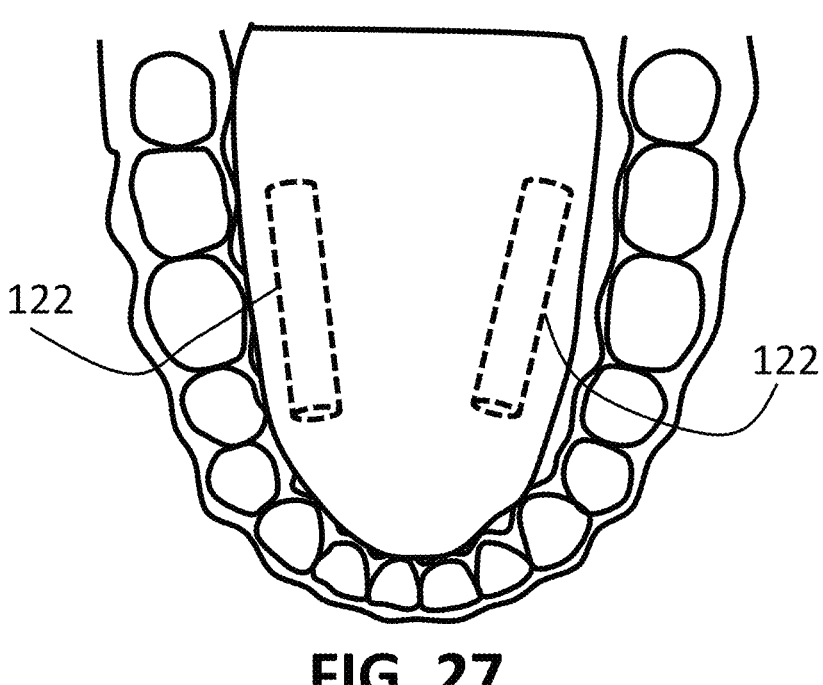
FIG. 27 shows another embodiment of a device comprising a sub-lingual anchor.
Figures 28, 29:
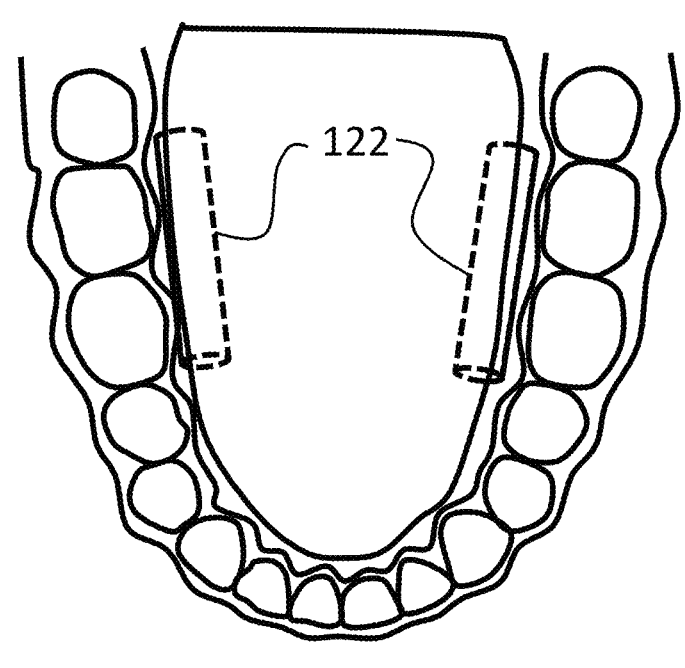
FIG. 28 shows another embodiment of a device comprising a sub-lingual anchor.
FIG. 29 shows another embodiment of a device comprising a surface anchor.

FIG. 26-29 show embodiments of the present invention that comprise one or more surface anchors (e.g., suction anchors) that can be reversibly attached to a tongue. FIG. 26 shows a U-shaped or curved suction anchor 122 that is located below the tongue. Suction anchor 122 attaches to one or more portions of the ventral side of the tongue to a tissue region inferior to the tongue. In some embodiments, the curvature of suction anchor 122 may be designed or configured to substantially match a curvature of a patient's mouth or jaw. For example, dimensions of a patient's tongue, mouth, jaw, etc. may be measured such that an implant can be designed specifically for the patient. FIG. 27 shows two elongate suction anchors 122 that are located below the tongue as shown. Suction anchors 122 attach, collectively, to two or more portions of the ventral side of the tongue to a tissue region inferior to the tongue. The dimensions of each suction anchor 122 may be the same or different, such that the dimensions may be adjusted to achieve the desired tissue displacement or therapeutic effect. FIG. 28 shows two elongate suction anchors 122 that are located below the tongue as shown. Suction anchors 122 attach, collectively, to two or more portions of the ventral side of the tongue to a tissue region inferior to the tongue.

Suction anchors 122 in FIG. 28 are located more lateral to those in FIG. 27, for example on a perimeter of a tongue. In FIG. 29, suction anchor 122 has sufficient physical dimensions such that it attaches to a region on the dorsal surface of the tongue and also to a region of the hard palate. Thus, the region on the dorsal surface of the tongue gets mechanically and/or reversibly fixed to the region of the hard palate.

The location, type, attachment force, vacuum, etc. of any of the suction anchors 122 disclosed herein may be adjusted and/or altered to adjust and/or alter the clinical effect of device 100 comprising the suction anchor 122. Any of the suction anchors 122 disclosed herein may be connected to an element of any embodiment of devices 100 disclosed herein.

Figure 30:
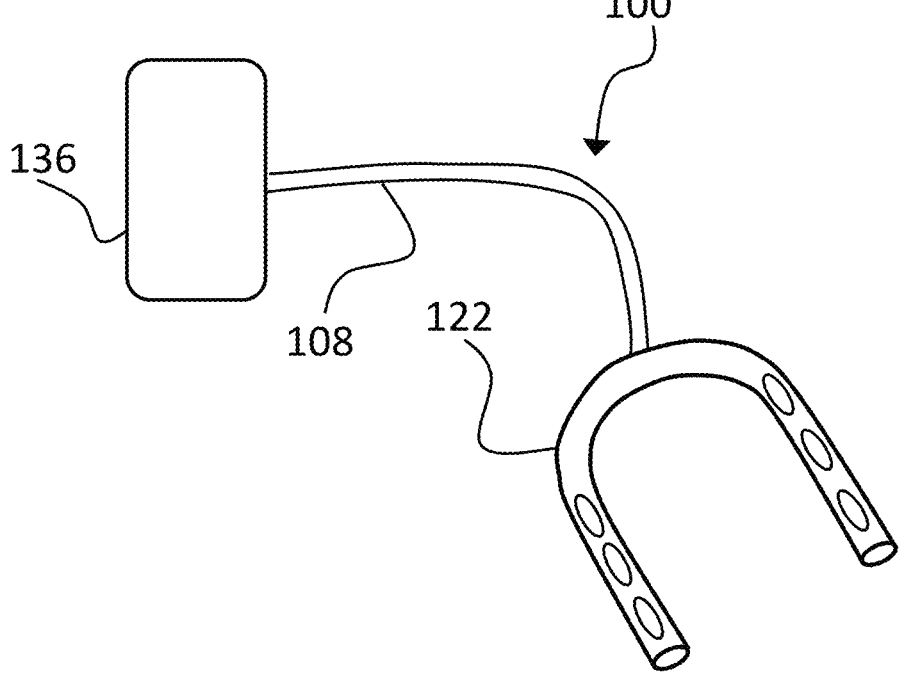
FIG. 30 shows another embodiment of a device comprising a sub-lingual anchor.

FIG. 30 shows a device embodiment of the present invention comprising a suction anchor 122 than can be reversibly attached to a tongue, wherein the suction anchor is connected to a vacuum pump 136. In FIG. 30, suction anchor 122 is connected to a vacuum pump 136 through a first elongate member 108 defining a lumen therethrough. First elongate member 108 is in fluid communication with vacuum pump 136. vacuum pump 136 acts as a vacuum generating element. This embodiment may further comprise a valve e.g., valve 134 of FIG. 24 that can be used to allow or block a fluid communication between vacuum pump 136 and suction anchor 122. The length and other dimensions of elongate member 108 may be such that suction anchor 122 is allowed to extend the tissue to a target displaced position while preventing the tongue from falling too deep into the patient's throat and obstructing the airflow. A size and/or shape of suction anchor 122 may be substantially similar to that of the patient's mouth or jaw. In some embodiments, a size and/or shape of suction anchor 122 is personalized for the patient, such that measurements are taken to determine a best fit between the patient's mouth and the suction anchor 122.

Figure 31:
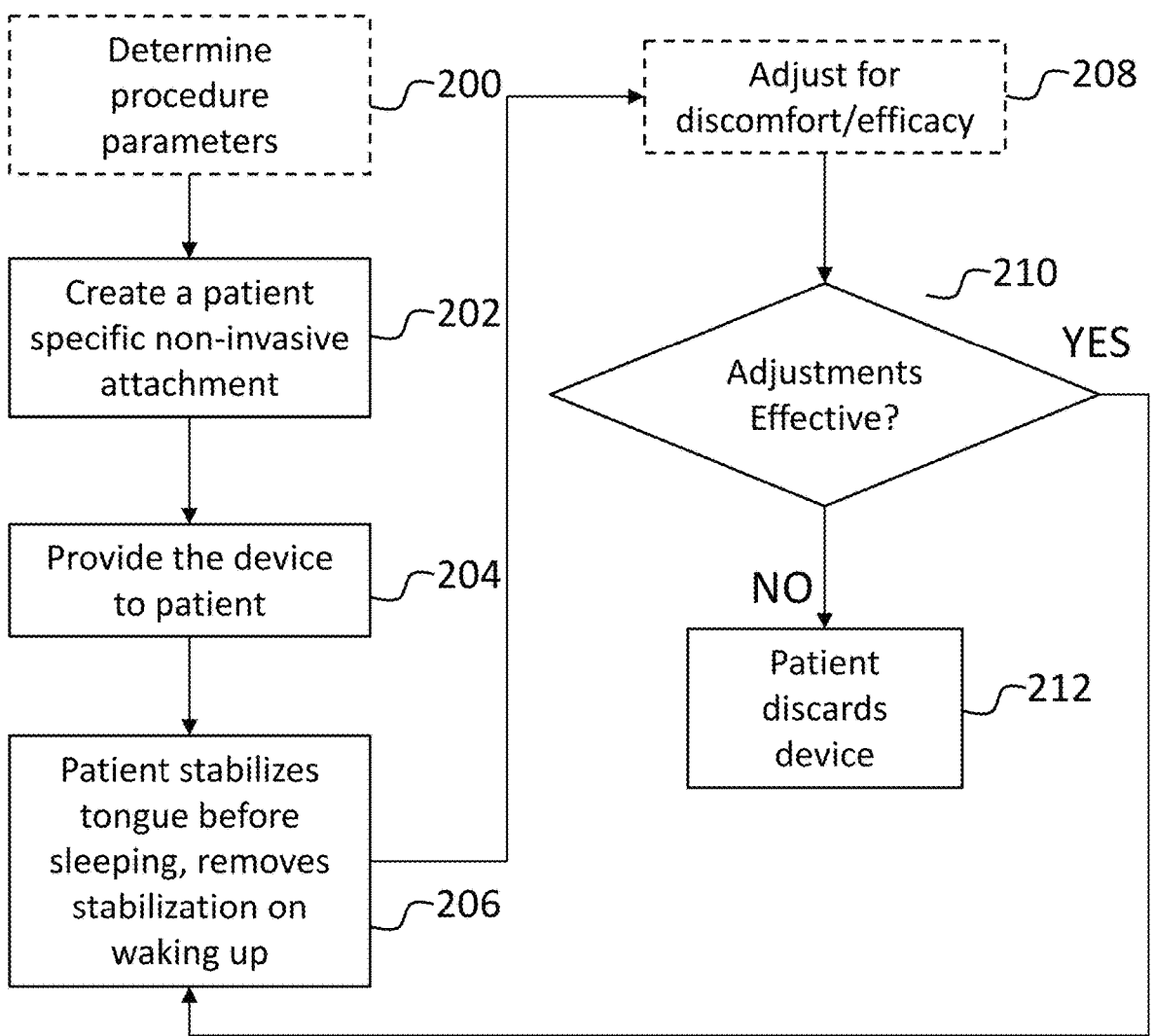
FIG. 31 shows another embodiment of a method of positioning or implanting a device.

FIG. 31 shows an embodiment of a method of the present invention wherein device 100 is non-invasive. At optional step 200, a healthcare provider (e.g., a surgeon, a dentist, etc.) determines one or more parameters of the procedure. Examples of such parameters include, but are not limited to: implant type (including size) or number of components of device 100 (e.g., suction anchor 122), location of one or more anchors, direction of one or more components of device 100, degree of restriction and/or displacement of the tongue, direction and/or magnitude of forces to be applied to the tongue, etc. At step 202, a patient specific non-invasive attachment (e.g., an external anchor 118) is created. Alternatively, a desired attachment may be selected for the patient. At step 204, the device (e.g., combination of one or more components such as suction anchor 122, external anchor 118, one or more elongate members, etc.) is provided to the patient. At step 206, the patient uses the device to stabilize the tongue as disclosed elsewhere herein. At optional step 208, the effect of the device is adjusted for one or more of: comfort/pain, pulling sensation, side effects, and efficacy. At step 210, a determination is made whether the adjustments are effective, for example are the adjustments achieving the desired clinical effect. When the adjustments are determined to be effective, the patient continues to use the device and the method returns to step 206. When the adjustments are determined to not be effective at step 210, the device 100 may be removed from the patient. A major advantage of the non-invasive methods and devices disclosed herein is that there are no long term or permanent changes to the patient's anatomy. Although the above steps are described sequentially according to the figures, one of skill in the art will appreciate that the steps may be executed in any sequence without departing from the original scope or intent of this disclosure.

Figure 32:
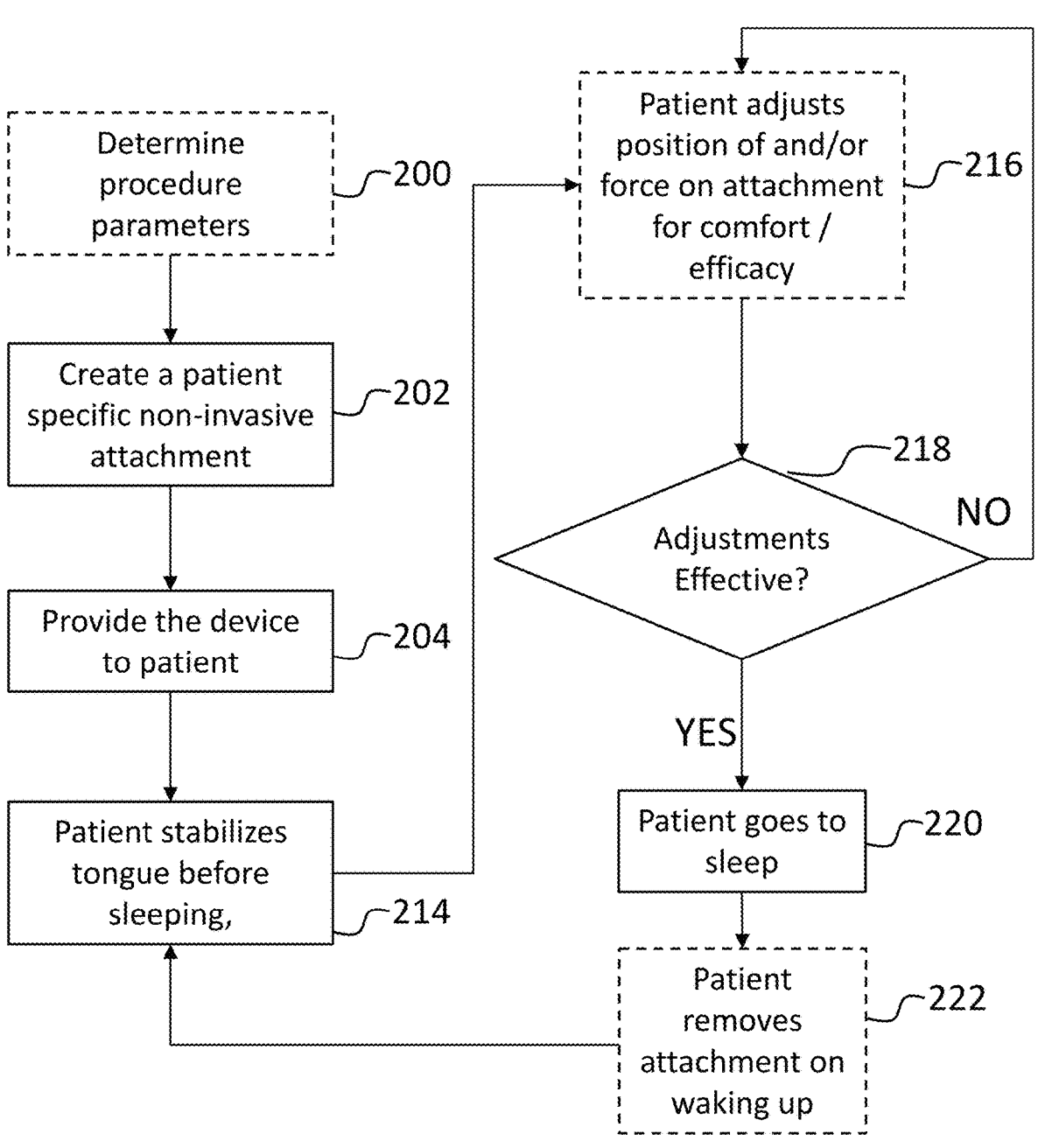
FIG. 32 shows another embodiment of a method of positioning or implanting a device.

FIG. 32 shows another embodiment of a method of the present invention wherein device 100 is non-invasive. Steps 200-204 are similar to those shown in FIG. 31. At step 214, the device is positioned and/or configured to stabilize the tongue as disclosed elsewhere herein. At optional step 216, the effect of the device is adjusted for one or more of: comfort/pain, pulling sensation, side effects, and/or efficacy. This may be performed by the patient or a physician by adjusting the position of and/or the force on one or more device regions. As described elsewhere herein, any of the devices described herein may be adjusted either by a health-care provider or by the patient. At step 218, a determination is made whether the adjustments are effective. When the adjustments are determined to not be effective at step 218, additional adjustments may be performed. When the adjustments are determined to be effective at step 218, the device continues to be used by the patient. At optional step 222, the attachment may be removed upon waking (depending on which device was selected for the patient—at least portions of certain embodiments can remain with the patient throughout the day). The method then returns to step 214. Although the above steps are described sequentially according to the figures, one of skill in the art will appreciate that the steps may be executed in any sequence without departing from the original scope or intent of this disclosure.

Figure 33:
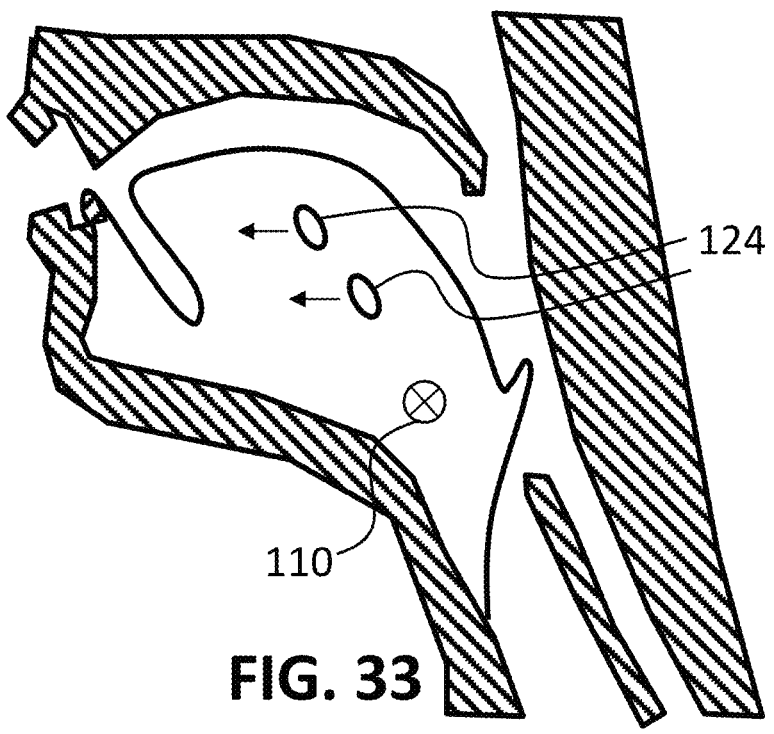
FIG. 33 shows one embodiment of a device comprising a magnet-based anchor.

FIG. 33 shows a section through a human head showing an embodiment of the present invention that comprises magnetic anchors 124. One or more magnetic anchors 124 may be embedded or implanted in or on the tongue. Magnetic anchors 124 may be adjusted by adjusting a magnetic force experienced by the anchors 124. The magnetic force experienced by the anchors 124 may be produced by an external magnet and/or a metallic material. The magnetic force may be adjusted in terms of magnitude and/or direction by varying the position of external magnetic materials. The magnetic force may be adjusted in terms of magnitude and/or direction by varying the position and/or action of external magnets. The adjustment may be performed based on any of the conditions disclosed herein. The adjustment may be performed to achieve any of the clinical effects disclosed herein.

Figure 34:
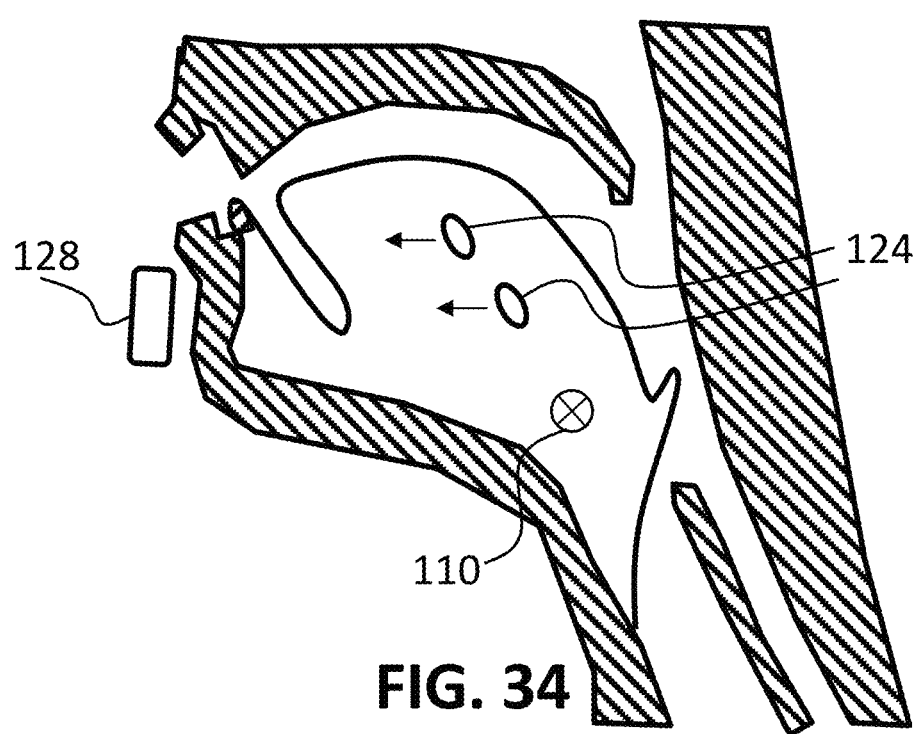
FIG. 34 shows another embodiment of a device comprising a magnet-based anchor.

FIG. 34 shows a section through a human head showing another embodiment of the present invention that comprises magnetic anchors. Magnetic anchors 124 may be adjusted by adjusting a magnetic force experienced by the anchors 124. In this embodiment, the magnetic force is adjusted based on input of sensor 128. The sensor may be coupled to the patient, for example via head gear, face mask, coupled to a bodily portion, etc. The adjustment may be performed based on any of the conditions disclosed herein. The adjustment may be performed to achieve any of the clinical effects disclosed herein.

Figure 35:
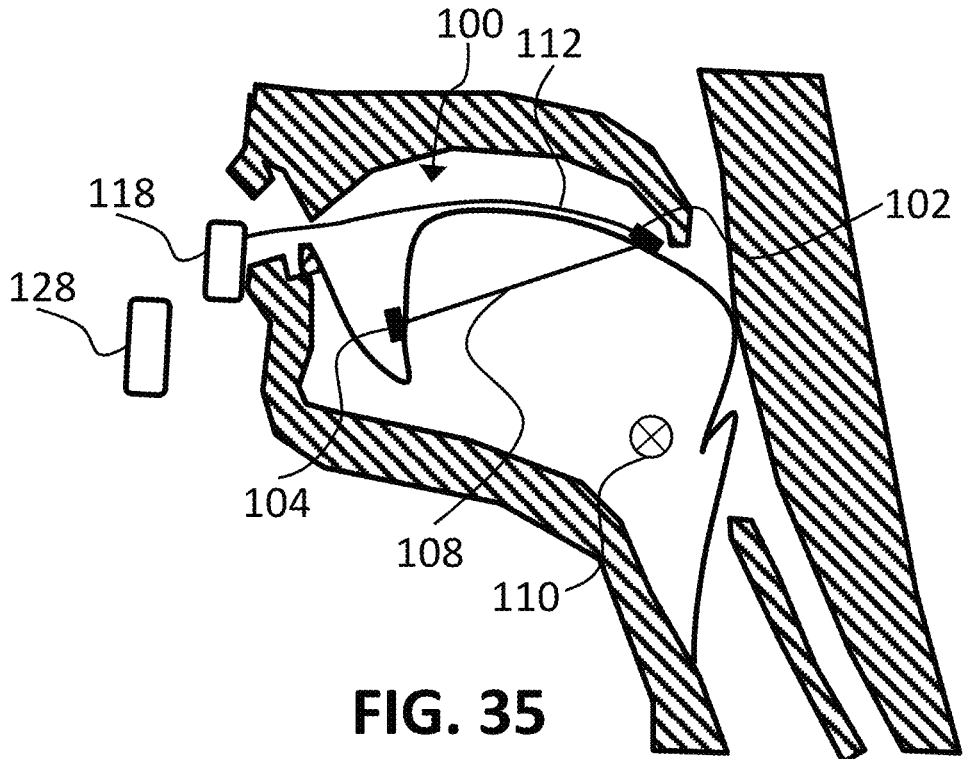
FIG. 35 shows one embodiment of a device that is adjustable based on sensor input.
Figure 36:
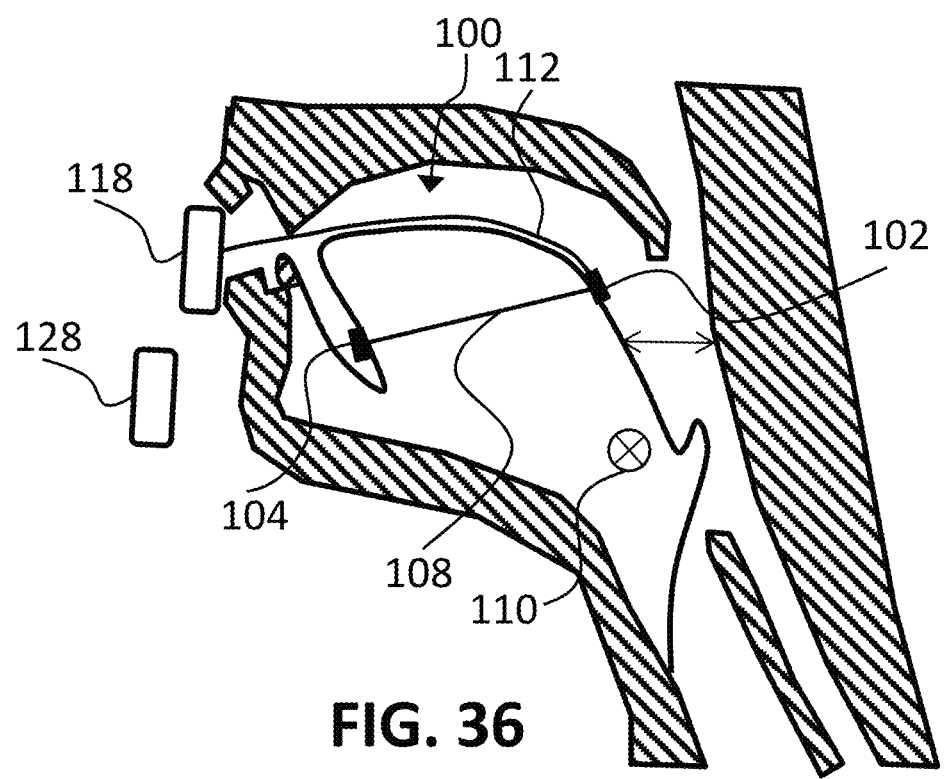
FIG. 36 shows another embodiment of a device that is adjustable based on sensor input.
Figure 37:
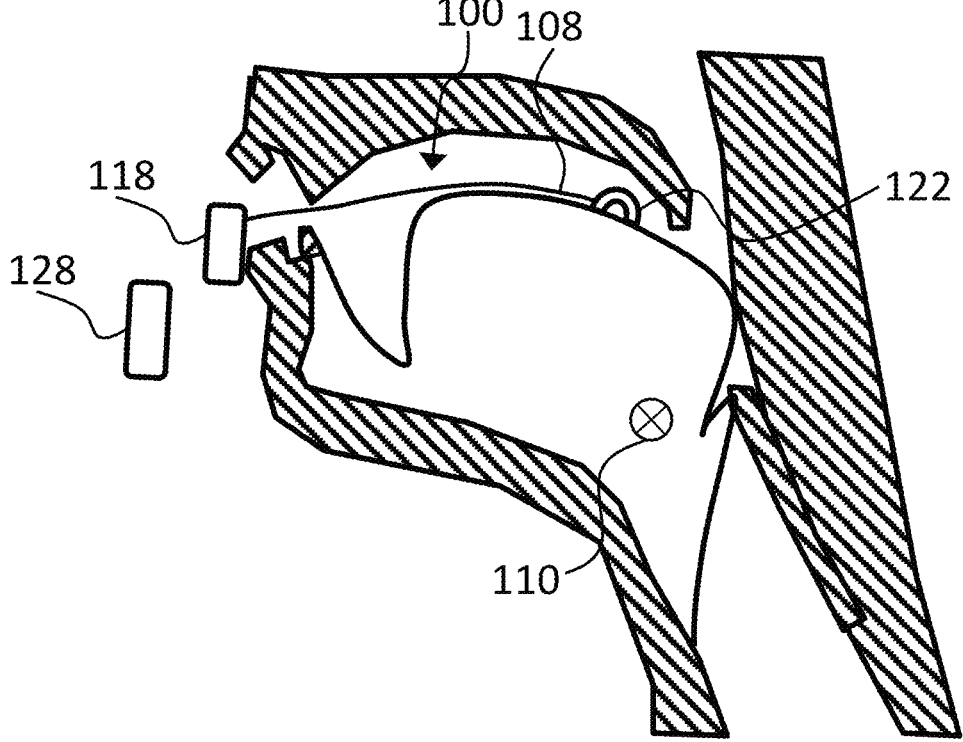
FIG. 37 shows another embodiment of a device that is adjustable based on sensor input.

FIGS. 35-37 show a section through a human head showing embodiments of devices that comprise or otherwise use an external sensor. FIG. 35 shows an embodiment comprising first or dorsal anchor 102, second or ventral anchor 104, and first elongate member 108. First anchor 102 is connected to an external anchor 118 through a second or dorsal elongate member 112. The clinical effect of device 100 can be adjusted using any of the methods herein. Examples of such methods include, but are not limited to: adjusting the tension on second member 112, adjusting the length of an elongate member, adjusting the force on an anchor, etc. The adjustment is made using input from a sensor 128. Any sensor 128 disclosed herein may detect and/or measure one or more parameters comprising one or more of: snoring and other noises, brain activity, eye movement, blood oxygen levels, breathing, sleep apnea, bio-impedance, motion of one or more body regions, orientation of one or more body regions, etc. Any sensor 128 disclosed herein may detect and/or measure one or more parameters throughout the night or throughout the patient's sleep. For example, in response to sensing one or more parameters, the device may be adjusted to improve or otherwise alter a therapeutic effect of the device. Sensor 128 may be located on the face or other bodily regions or may be located near to the patient, e.g., on or near the patient's bed. Sensor 128 may be located on bands around the chest or abdomen, on a film, or on a wearable device. Sensor 128 may comprise one or more microelectronic systems. Specific examples of sensors 128 include, but are not limited to: sensors on Smart Nora™; smart phones loaded with apps such as SnoreLab; sensors located on anti-snore pillows such as Smart Sensor Anti-Snore Pillow; sensors located on SmartSleep Snoring Relief Band made by Philips North America Corporation, Andover, MA; etc.

In FIG. 36, device 100 is adjusted by increasing a pull force, anteriorly, on dorsal anchor 102 by external anchor 118. This may cause the forward displacement of one or more portions of the tongue as seen in FIG. 36. In one embodiment, sensor 128 detects the breathing and/or snoring of the patient. The pull force on anchor 102 is increased when the patient breathes in and is released/reduced when the patient breathes out. In this way, the effect of device 100 is timed to the patient's physiological condition. In another embodiment, sensor 128 detects lowered blood oxygen saturation or sleep apnea. Thereafter, the pull force on anchor 102 is increased to remove one or more airway obstructions (e.g., due to posterior region of the tongue) thereby increasing the patient's blood oxygen saturation. Conversely, the pull force on anchor 102 may be reduced or maintained when the patient's blood oxygen saturation is at a desired level or when sleep apnea is not detected. In another embodiment, sensor 128 detects snoring by the patient. Thereafter, the pull force on anchor 102 is increased to remove one or more airway obstructions (e.g., due to posterior region of the tongue) thereby reducing the patient's snoring. Conversely, the pull force on anchor 102 may be reduced or maintained when snoring is not detected.

FIG. 37 shows an embodiment comprising suction anchor 122 connected to an external anchor 118 through a first or dorsal elongate member 108. The clinical effect of device 100 can be adjusted using any of the methods herein. Examples of such methods include, but are not limited to: adjusting the tension on first elongate member 108, adjusting the length of elongate member 108, adjusting the force on anchor 122, etc. The adjustment is made using input from a sensor 128 through any of the methods disclosed herein.

FIG. 38A shows an embodiment of an implant that is a component of device 100. Such implants may be used with any of the methods and devices disclosed herein. The implant shown in FIG. 38A comprise a first anchor 102 and a second anchor 104 that are connected by a first elongate member 108. In one embodiment, anchor 102 is permanently attached to member 108. Member 108 comprises an attachment mechanism that is used to securely attach second anchor 104 to elongate member 108. In the embodiment shown, the attachment mechanism is a screw mechanism.

FIG. 38B shows an embodiment of an attachment mechanism of device 100. Such attachment mechanisms may be used with any of the methods and devices disclosed herein.

The attachment mechanism may be attached to a suitable implant or an anchor shown herein. The attachment mechanism comprises an external anchor 118 that is attached to an elongate member 112. In the embodiment shown, external anchor 118 is designed to be attached to the patient's teeth. For example, external anchor 118 may comprise a mouth guard, bite splint, dental fixture, etc. In the embodiment shown, elongate member 112 is a flexible strap that defines one or more openings or apertures 500. These apertures 500 may be pressed onto an anchor to secure the anchor (e.g., first anchor 102, second anchor 104, etc.) to elongate member 112. The force on the tongue by device 100 and other parameters (examples of which include, but are not limited to distances, displacements, etc.) can be adjusted to multiple levels as per any of the methods disclosed herein by adjusting or altering which aperture 500 that connects to or is coupled to an anchor. Any of the embodiments disclosed herein may be designed to allow multiple levels of adjustment to one or more working parameters. Examples of such working parameters include, but are not limited to: magnitude and/or direction of one or more forces, displacements, distances, locations, etc. For example, devices 100 may be designed such that the length of elongate members between anchors can be adjusted. This adjustment may be performed by the patient. The adjustment may be performed by changing the site of attachment of one or more anchors on an elongate member.

FIG. 38C shows an embodiment of device 100 comprising a non-invasive mechanism for stabilizing the tongue. Such devices 100 may be used with any of the methods and devices disclosed herein. Device 100 comprises an external anchor 118 that is attached to an elongate member 112. In the embodiment shown, external anchor 118 is designed to be attached to the patient's teeth. In the embodiment shown, elongate member 112 is a flexible strap that defines one or more openings or apertures 500. These apertures 500 may be pressed onto one or more suction anchors 122 to secure anchor attachment 502 to member 112. The force on the tongue by device 100 can be adjusted as per any of the methods disclosed herein by adjusting or altering which aperture 500 connects to an anchor 122. Any suitable embodiments disclosed herein such as the embodiment of FIG. 38C may be designed as a single integrated device wherein the components of device 100 that are placed on bodily regions do not physically separate from each other. This design reduces the risk of component separation and choking during use. In one such embodiment, suction anchor 122 has an attachment (e.g., mechanical connector(s), strings, wires, etc.) to elongate member 112 which allows repositioning of suction anchor 122 on various apertures 500 but prevents physical separation of suction anchor 122 from the rest of device 100 even if suction anchor 122 is separated from an aperture 500.

Device embodiments disclosed herein may be designed to reduce or eliminate the hazard of triggering a gag reflex or producing a choking hazard during use. In one such embodiment, additional mechanical connections are provided that connect one or more components of device 100. For example, in embodiments comprising two anchors connected by an elongate member, a separate mechanical connector may be provided that connects the two anchors. In case the elongate member breaks, the anchors mechanically will still remain connected through the mechanical connector. The mechanical connector may have a higher strength than the elongate member. The mechanical connector may be longer than the elongate member. In another embodiment, elongate members and/or one or more connections disclosed herein may be reinforced for extra mechanical strength. Examples of reinforcements include, but are not limited to: metallic materials such as wires embedded in or otherwise attached to device components, use of thicker materials, use of coating(s) that reinforce device components, etc. In another embodiment, device 100 is designed such that a loss of function occurs before mechanical separation of one or more components. For example, loss of function may be felt through one or more of: loss of vacuum/suction, loss of a force, loss of a clinical action, etc. before mechanical separation occurs. In one specific example, breakage of an elongate member 108 causes a vacuum loss before complete breakage of elongate member.

Device embodiments disclosed herein may be designed to reduce or eliminate the hazard of triggering a gag or producing a choking hazard during use.

Figure 39:
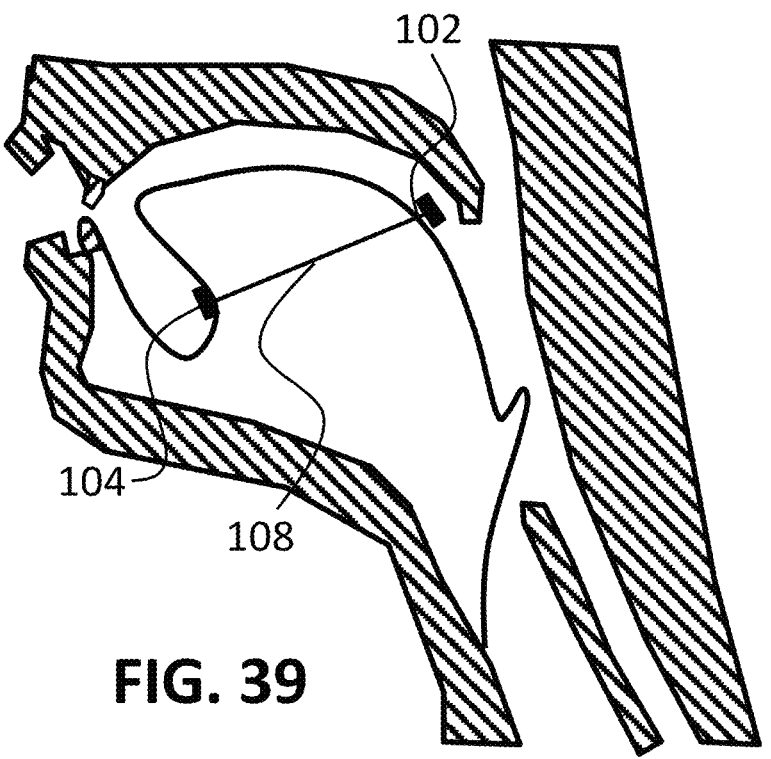
FIGS. 39-42 show various steps of a method of applying a displacement force to a tongue using a tongue anchor-based device.
Figure 40:
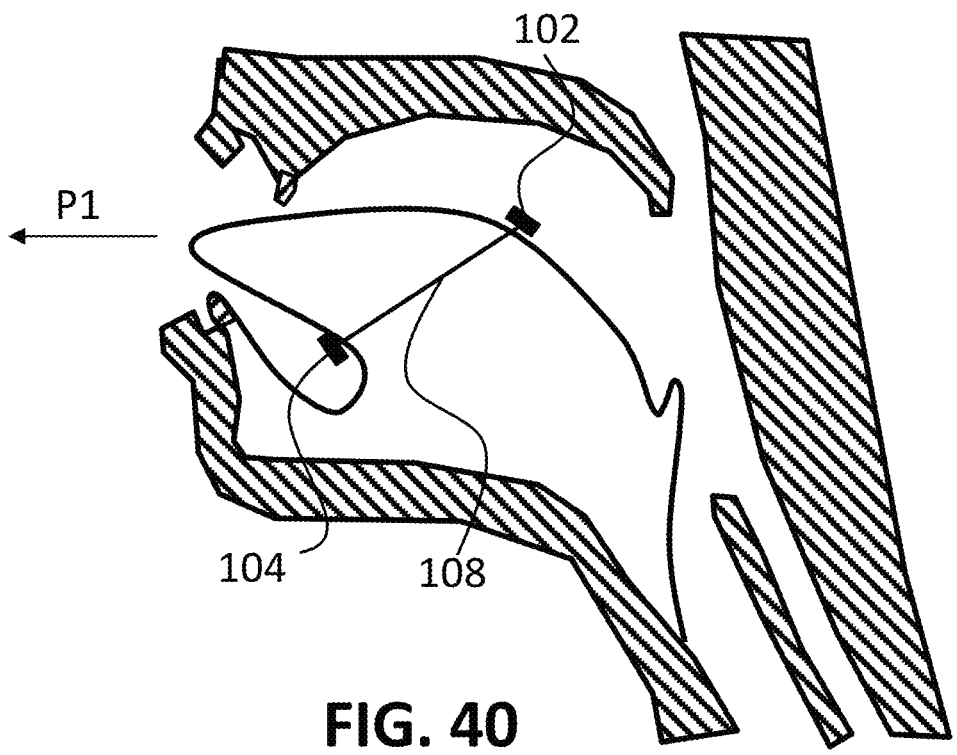
Figure 41:
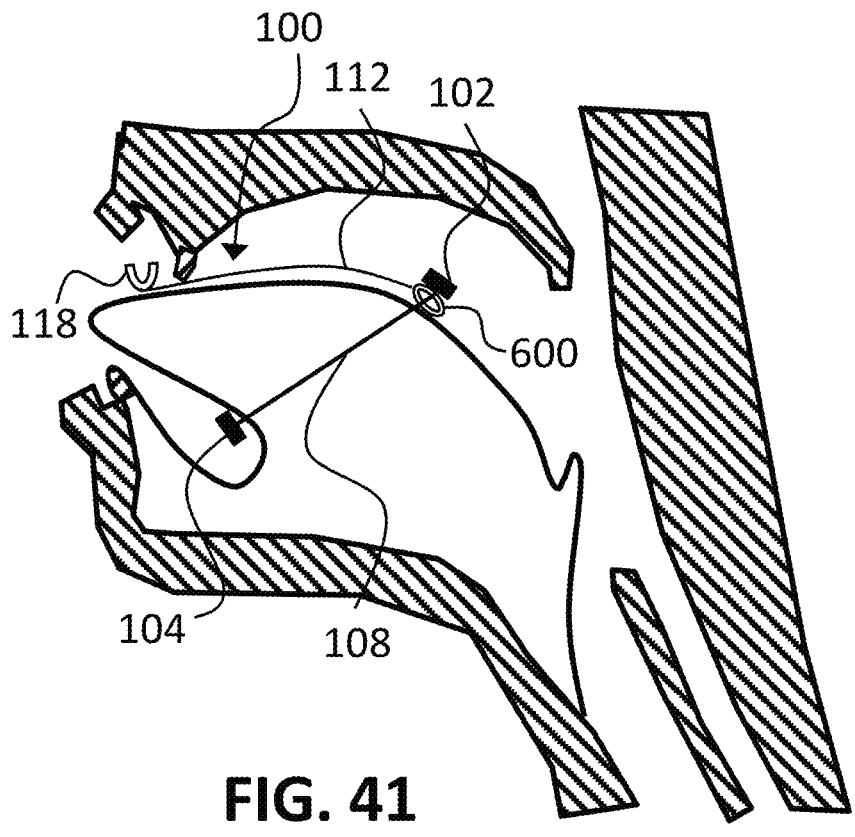
Figure 42:
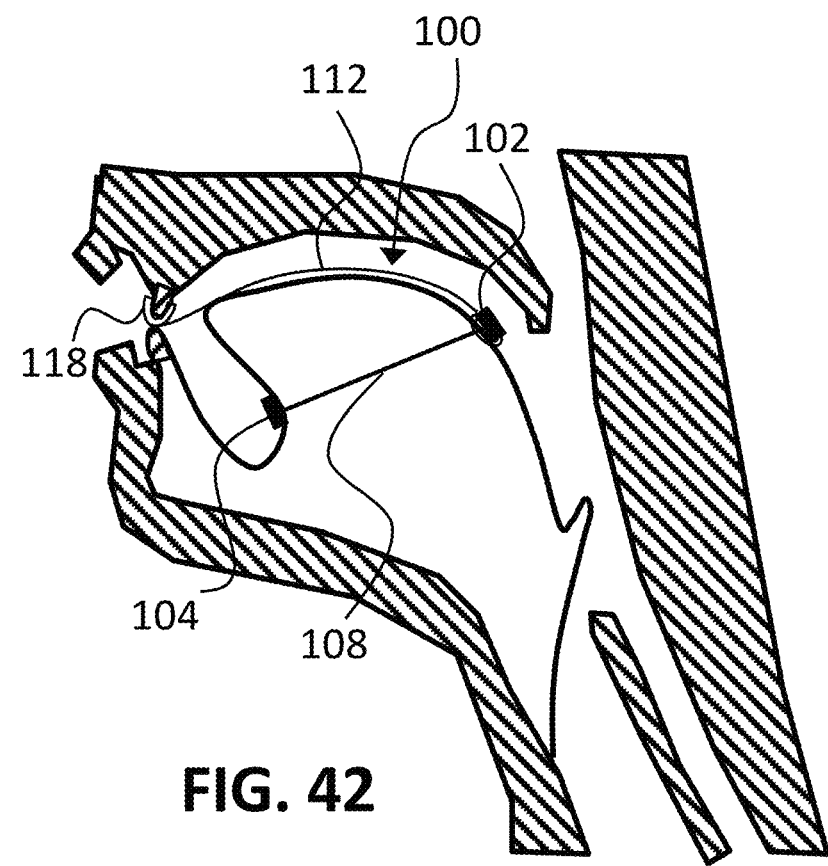

FIGS. 39-42 show an embodiment of a method of reversibly stabilizing the tongue. This may be used, for example, when the patient is going to sleep and wants to keep the airway open. FIG. 39 shows the normal resting position of the tongue. In FIG. 40, the patient pulls the tongue forward, shown as arrow P1, so that a first or dorsal anchor 102 is made more accessible to the attachment shown in FIG. 41. In FIG. 41, an attachment is inserted into the mouth. The attachment comprises an external anchor 118 connected to a coupling element 600 (e.g., loop, lasso, hook, clip, etc.) via a second or dorsal elongate member 112. The patient connects the coupling element 600 to the implant of FIG. 40 (e.g., via first or dorsal anchor 102). This may be performed, by example, by attaching coupling element 600 to first anchor 102. Thereafter, in the step shown in FIG. 42, external anchor 118 is connected to a region of the patient's upper or lower teeth. This stabilizes the tongue and prevents the tongue from falling posteriorly when the patient is asleep. The patient may then relax the tongue and go to sleep. When the patient wakes up and no longer needs the tongue stabilization, the tongue is advanced forward and coupling element 600 is detached from first anchor 102. External anchor 118 is detached from the patient's teeth and the attachment is removed from the patient's mouth.

In any of the embodiments herein, one or more anchors such as first anchor 102 and second anchor 104 may be designed and/or positioned such that one or more anchors or each anchor is physically separated by a distance from the tissue boundary. Thus, there may be a physical gap between an anchor and the tissue in the working position of the device. This allows the patient to easily attach elements such as coupling element 600 to the anchors.

In any of the embodiments herein, one or more anchors such as first anchor 102 and second anchor 104 may be designed and/or placed such that the anchors are easily accessed by the patient without needing to reach deeply inside the mouth or without producing a gag reflex. This may be achieved by placing the anchors at accessible regions such as the tongue body and avoiding regions such as the tongue base. This placement allows the patient to easily attach elements such as coupling element 600 to one or more anchors.

Figure 43:
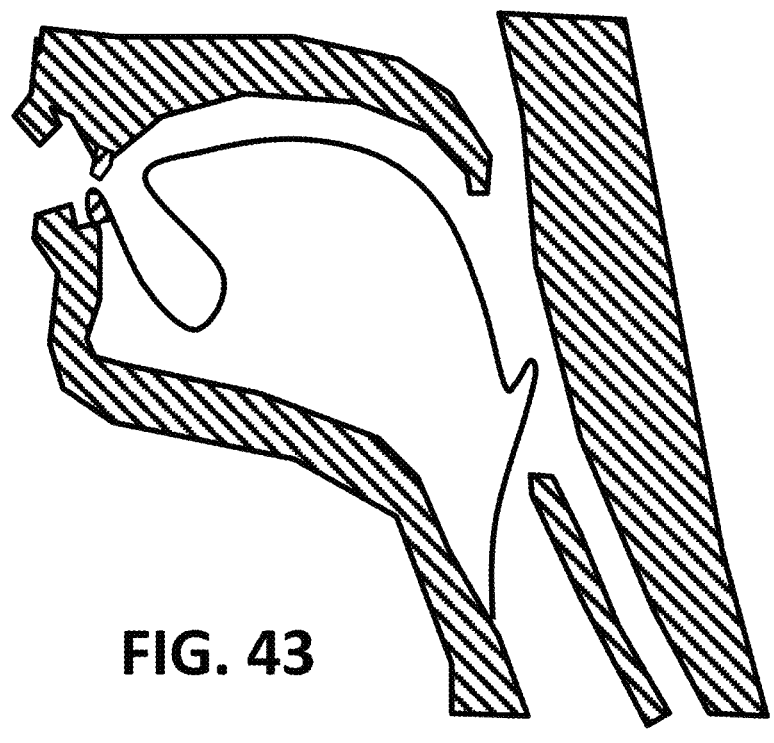
Figure 44:
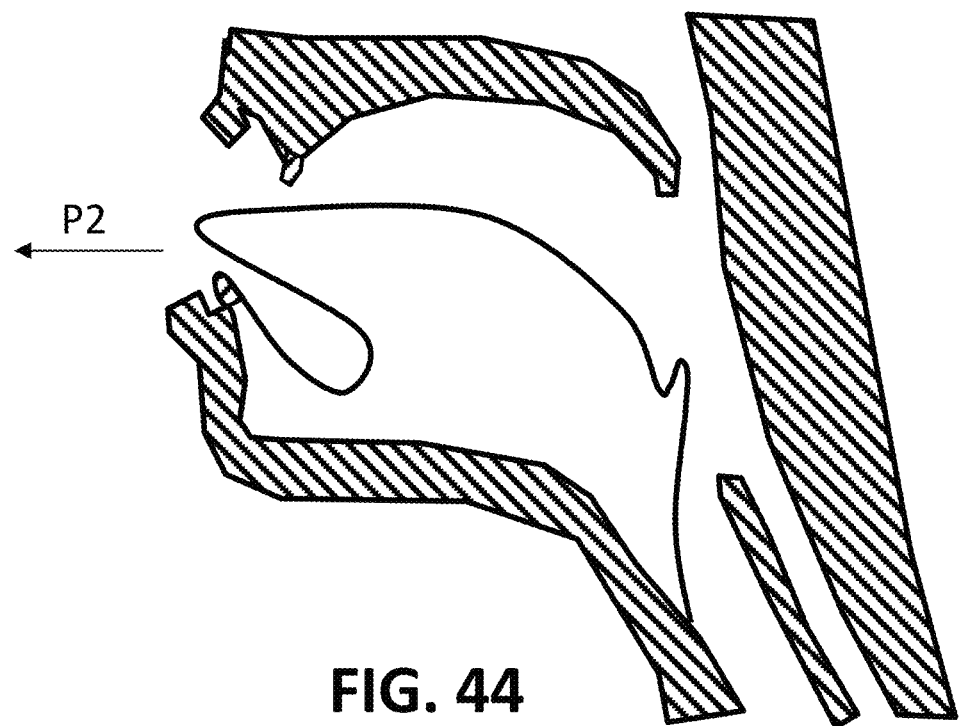
Figure 45:
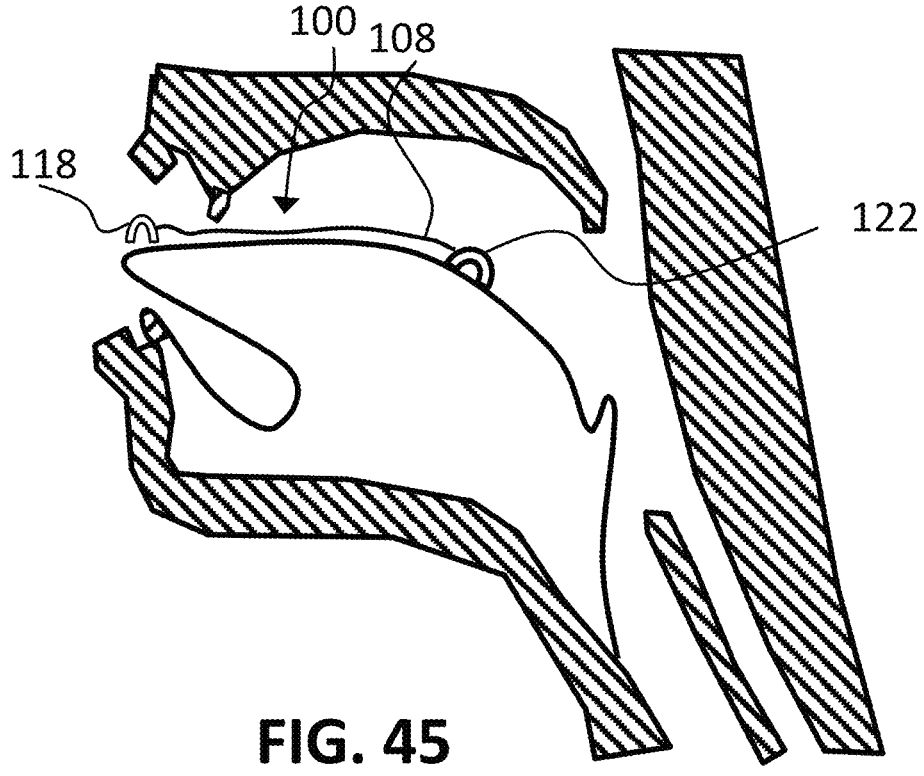

FIGS. 43-46A show one embodiment of a method of reversibly stabilizing the tongue using a non-invasive device. This may be used, for example, when the patient is going to sleep and wants to keep the airway open. FIG. 43 shows the normal resting position of the tongue. In FIG. 44, the patient pulls the tongue forward, shown as arrow P2, so that the target location of the tongue for suction anchor 122 is made more accessible. In FIG. 45, device 100 is inserted into the mouth. Device 100 comprises an external anchor 118 connected to a suction anchor 122 through a first elongate member 108. The patient attaches suction anchor 122 to the tongue using any suitable method, examples of which are disclosed elsewhere herein. In the step shown in FIG. 46A, external anchor 118 is connected to a region of the patient's lower or upper teeth. This stabilizes the tongue and prevents the tongue from falling posteriorly when the patient is asleep. The patient may then relax the tongue and go to sleep. When the patient wakes up and no longer needs the tongue stabilization, the tongue is advanced forward and suction anchor 122 is detached from the tongue. External anchor 118 is detached from the patient's teeth and device 100 is removed from the patient's mouth.

Figure 46A:
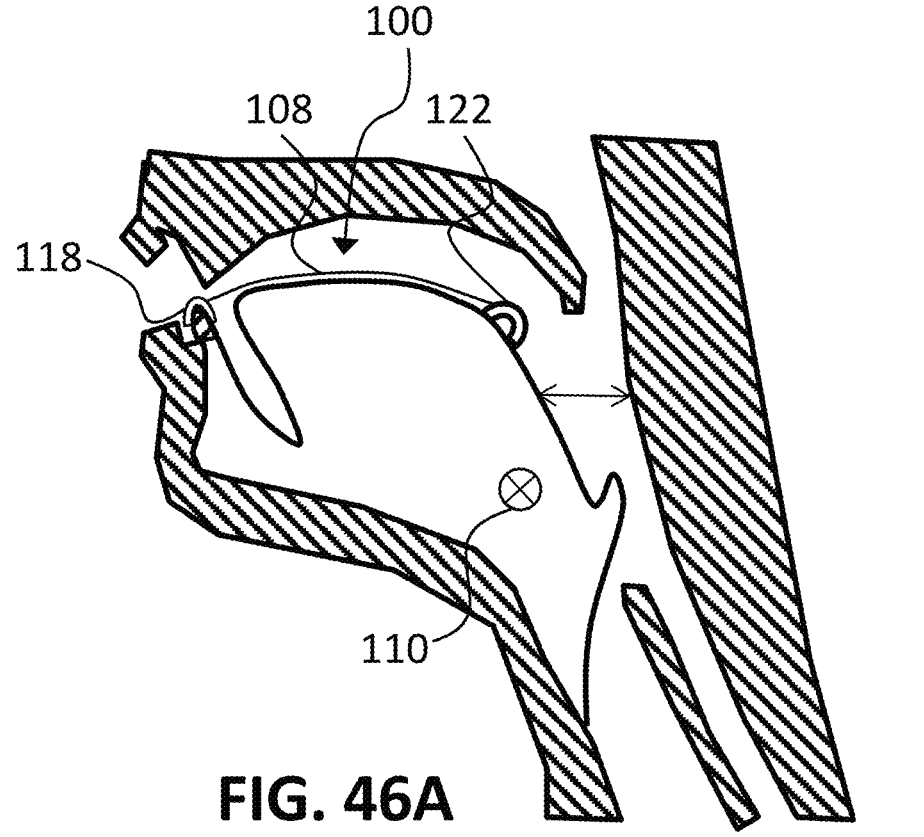
Figure 46B:
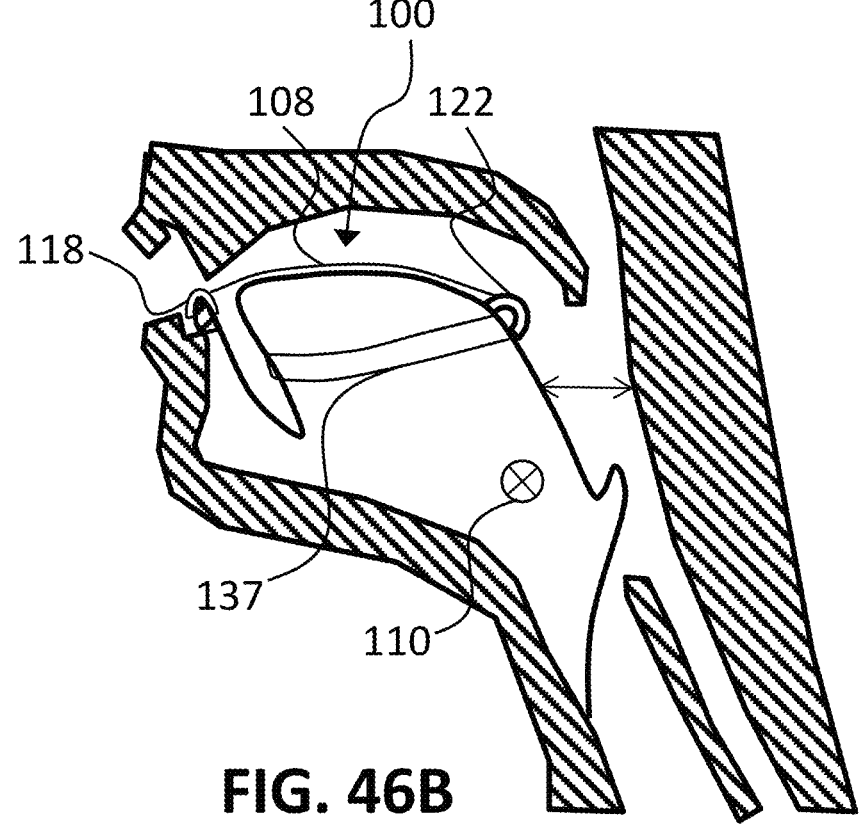
FIG. 46B shows an embodiment similar to the embodiment shown in FIG. 46A that comprises a band that envelops a portion of the tongue.

FIG. 46B shows an embodiment similar to the embodiment shown in FIG. 46A that comprises a band that envelops a portion of the tongue. Band 137 is designed such that it envelops a portion of or the entirety of the circumference of a tongue region. Band 137 may be made of elastic or non-elastic materials. In the embodiments disclosed herein, band 137 may provide one or more of the following functions: increase the force with which an anchor presses on to the tongue, improves contact of an anchor with the tongue, prevents an anchor from sliding relative to the tongue surface, prevents the loss of vacuum, increases patient comfort when a patient uses the device, stabilizes the orientation of an anchor relative to the tongue (e.g. prevents rotation of an anchor relative to the tongue), and/or prevents aspiration or choking from one or more device components. In one embodiment, elongate member 108 is mechanically connected to band 137 such that as elongate member 108 is pulled, the increased tension in band 137 causes band 137 to tighten around the tongue. In one embodiment, an elastic band 137 pushes a suction anchor closer to the tongue thereby creating a better seal between the anchor and the tongue, which in turn prevents the loss of vacuum from the suction anchor. The length of band 137 may be adjusted to achieve one or more of: achieve a desired position of band 137 on the tongue, achieve a desired force between an anchor and the tongue, etc. Such bands 137 that go around a portion of the tongue may be incorporated into other embodiments disclosed herein.

Figure 47:
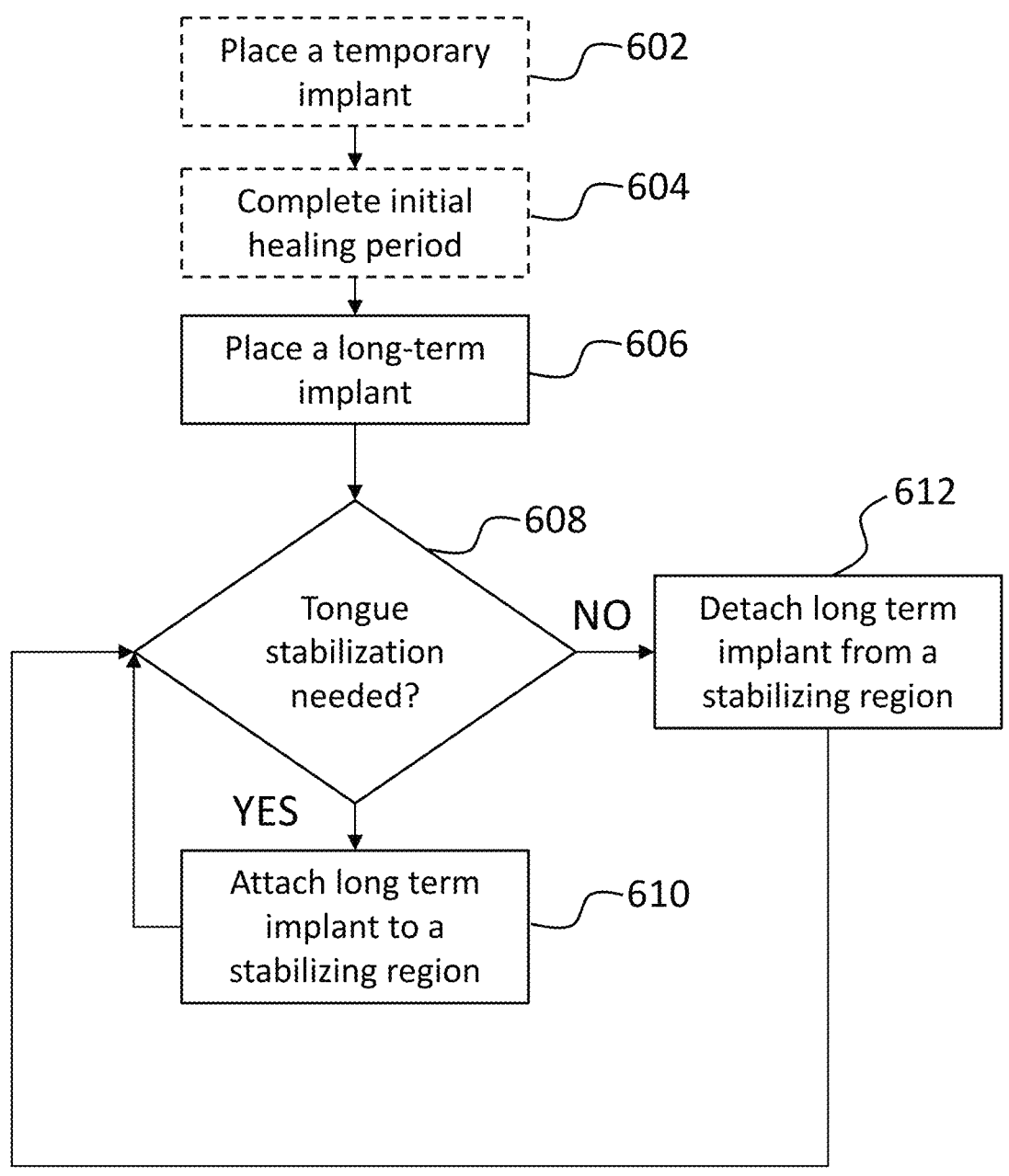
FIG. 47 shows one embodiment of a method of stabilizing a tongue of a patient.

FIG. 47 shows an embodiment of a method for reversibly stabilizing the tongue when needed and removing the stabilization when not needed. At optional step 602, a temporary implant is placed as disclosed elsewhere herein. At optional step 604, an initial healing period is completed as disclosed elsewhere herein. At step 606, a long-term implant is placed as disclosed elsewhere herein. At step 608, the user determines when tongue stabilization is needed. When tongue stabilization is needed, at step 610, the long-term implant is attached to a stabilizing region (e.g., the patient's teeth). When tongue stabilization is not needed, at step 612, the long-term implant is detached from the stabilizing region so that it does not interfere with the normal tongue functions like tasting, talking, eating, etc. In this way, an "on-demand" tongue stabilization action may be used to improve the airflow through the airway.

Figure 48:
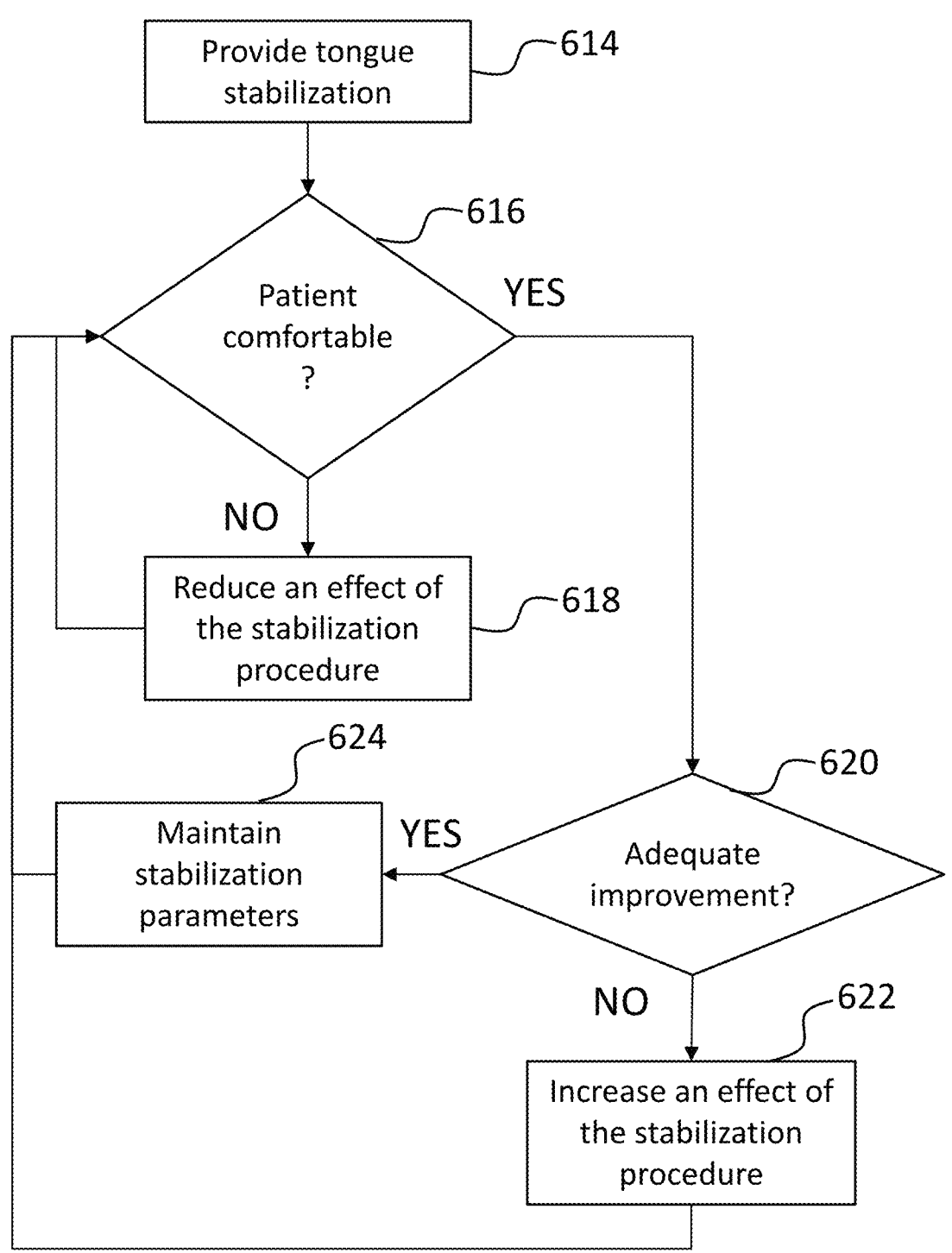
FIG. 48 shows another embodiment of a method of stabilizing a tongue of a patient.

FIG. 48 shows an embodiment of a method for adjusting a stabilizing effect on the tongue. At step 614, a method described herein is used to provide tongue stabilization. At step 616, the patient determines when the tongue stabilization is comfortable. When it is comfortable, the patient determines when the improvement in symptoms due to tongue stabilization is adequate. In one such embodiment, the patient determines when the improvement in snoring is adequate. In one such embodiment, the patient determines when the improvement in sleep apnea is adequate. In one such embodiment, the patient determines when the improvement in a sleep or respiration parameter is adequate. When the improvement is not adequate, the effect (e.g., force increased on implant attached to the tongue) of the stabilization procedure is increased at step 622. For example, this effect may be increased by increasing a stabilization force on the tongue. The method then proceeds back to step 616. When the improvement is adequate, the stabilization parameters (including, but not limited to: type of device 100, locations of one or more components of device 100, forces on the tongue, etc.) are maintained and the method returns to step 616. When at step 616, the patient determines that the tongue stabilization is not comfortable, the effect of the stabilization procedure is reduced at step 618. For example, this effect may be reduced by reducing a stabilization force on the tongue.

Figure 49:
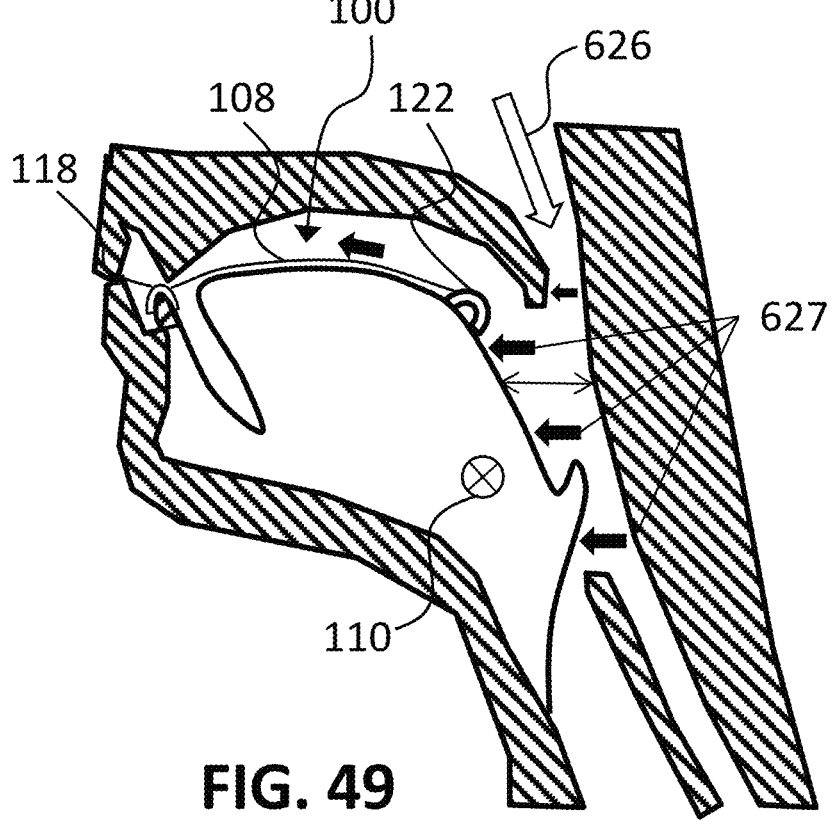
FIG. 49 shows a combination embodiment that includes an implant and positive airway pressure.

Any of the embodiments disclosed herein may be used in combination with any therapy that generates a positive airway pressure; examples of which include, but are not limited to: Continuous Positive Airway Pressure (CPAP) systems and nasal resistance devices. In such combination embodiments, forces are applied on the tongue and other anatomical regions from: the devices disclosed herein and/or the positive pressure acting on tissue surfaces. FIG. 49 shows an embodiment of a method of treating a patient using an embodiment disclosed herein in combination with positive airway pressure. The open arrow 626 in FIG. 49 shows the direction of the airflow and the solid arrows 627 show the forces exerted on the tongue and soft palate. As shown in FIG. 49, the positive airway pressure creates an anterior displacement force on one or more of: tongue regions and soft palate regions. Also, the tongue interventions (any disclosed herein although a suction anchor is shown) disclosed herein create a displacement force on one or more tongue regions. This displacement force comprises an anterior component. Thus, in such combination embodiments, the forces act on the soft palate and also on the tongue. This may improve sleep disordered breathing. The combination embodiments are especially useful in obese patients and in patients where the soft palate is also contributing to snoring or OSA. Such combination embodiments may create a synergistic effect that keeps the airway open. One or more tongue interventions disclosed herein may be used to prevent or reduce the tongue from falling back on (i.e., exerting a posterior force on) portions of the soft palate. When these forces are prevented or reduced, posterior displacement of the soft palate is also prevented or reduced. A positive airway pressure modality can then act on the soft palate and easily displace the soft palate anteriorly. This synergistic effect means that the forces needed to splint the airway open by displacing portions of the soft palate and/or the tongue are significantly reduced. This in turn means that the positive airway pressure modality can achieve its desired effect even with lower airway pressures. This significantly increases the tolerability and patient acceptance of such modalities.

Any of the embodiments disclosed herein may be used in combination with any therapy that affects a portion of the airway. One example (combination with a therapy that generates a positive airway pressure) was disclosed in the previous paragraph. Other examples of such therapies include, but are not limited to: nasal surgery (e.g. surgical modification of the septum or turbinates), nasal valve modification (heat or radiofrequency based remodeling of nasal cartilage and/or soft tissue), oral devices, drugs (e.g. anti-allergy drugs, anti-inflammatory drugs, etc.), reducing the resistance to airflow at one or more airway locations, neurostimulation of the upper airway (e.g. INSPIRE® therapy), external neurostimulation, etc.

In one method embodiment, a tongue device is placed on or implanted on the patient's tongue. Thereafter, a patient starts the action of a tongue device. Several examples of such procedures and actions are listed in this specification. The patient then turns on the positive airway pressure modality. The effect of the combination procedure may be adjusted based on one or more of: efficacy and tolerability of the combination procedure. One or more parameters of the combination procedure may be adjusted based on the above. Examples of such parameters include, but are not limited to: forces applied on the tongue, location of one or more device portions on the tongue, location of one or more external anchors, lengths of one or more connectors, pressure levels, etc. The combination procedures may be used for gradually weaning the patient off or tapering off one or more treatments. In one embodiment, a combination procedure starts with a larger force on the tongue and a lower airway pressure. Thereafter, the force on the tongue and/or airway pressure is adjusted for increased efficacy and/or tolerance. In one embodiment, a combination procedure starts with a smaller force on the tongue and a higher airway pressure. Thereafter, the force on the tongue and/or airway pressure is adjusted for increased efficacy and/or tolerance. Eventually, a combination procedure may transition to only a single mechanism—tongue displacement or positive airway pressure.

Figure 50:
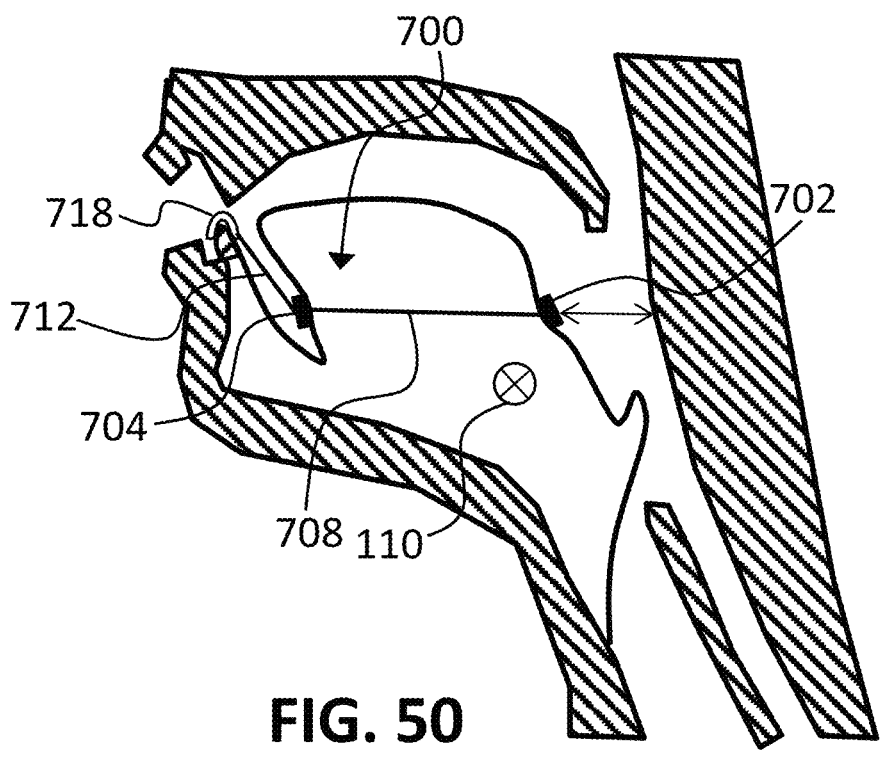
FIG. 50 shows one embodiment of a device configured for positioning at a tongue base.
Figure 51:
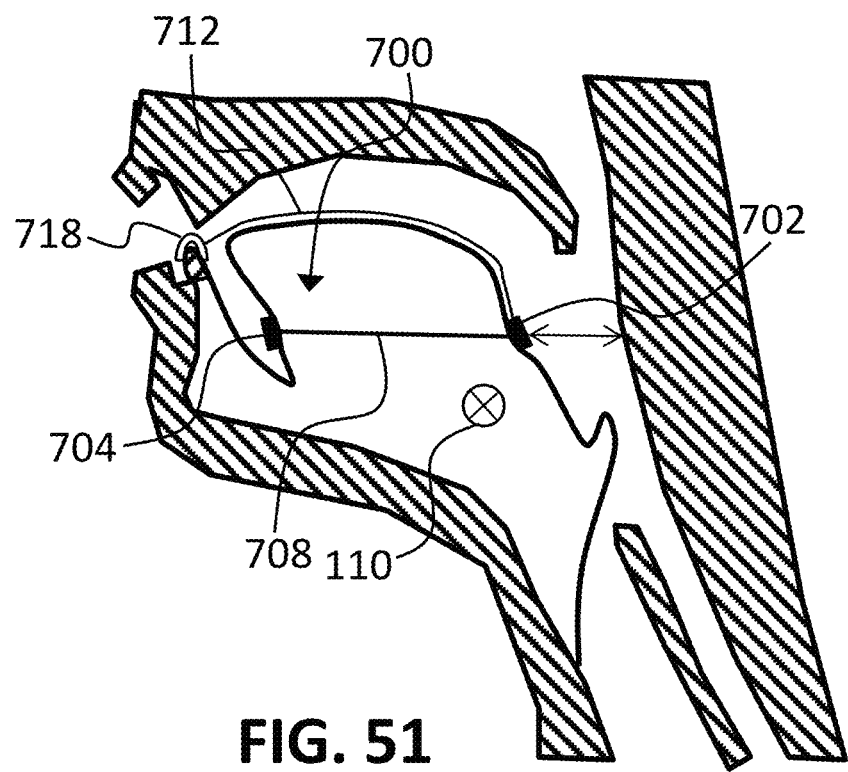
FIG. 51 shows another embodiment of a device configured for positioning at a tongue base.

FIGS. 50-51 show two embodiments, respectively, of devices 700 of tongue stabilization that also compress one or more regions of the tongue base. In FIGS. 50-51, the tongue base has been compressed using an implant comprising a first tongue base anchor 702, a first elongate member 708, and a second anchor 704. In FIG. 50, an attachment comprising an external anchor 718 (connected to the lower teeth) and a second elongate member 712 (connected to second anchor 704) are used to stabilize the tongue. In FIG. 51 an attachment comprising an external anchor 718 (connected to the lower teeth) and a second elongate member 712 (connected to first tongue base anchor 702) is used to stabilize the tongue. Examples of such attachments are disclosed elsewhere herein. Examples of methods and devices to compress one or more regions of the tongue base are disclosed in US patent publication no. 20200069320; U.S. Pat. No. 10,195,010; and US patent publication no. 20200330262; the entire disclosures of each of which are incorporated herein by reference. Such compression devices may be attached to attachment devices disclosed herein using methods disclosed herein to provide tongue stabilization in addition to tongue compression.

The force generated by any of the embodiments herein may be sufficient to displace a portion of the tongue and/or supraglottis to reduce the resistance to airflow at the level of the oropharynx or hypopharynx.

Figure 52:
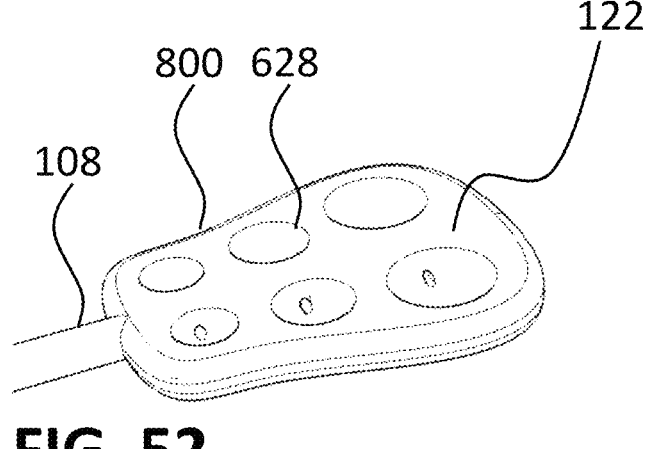
FIG. 52 shows a bottom view of one embodiment of a suction-based device comprising one or more suction wells.
Figure 53:
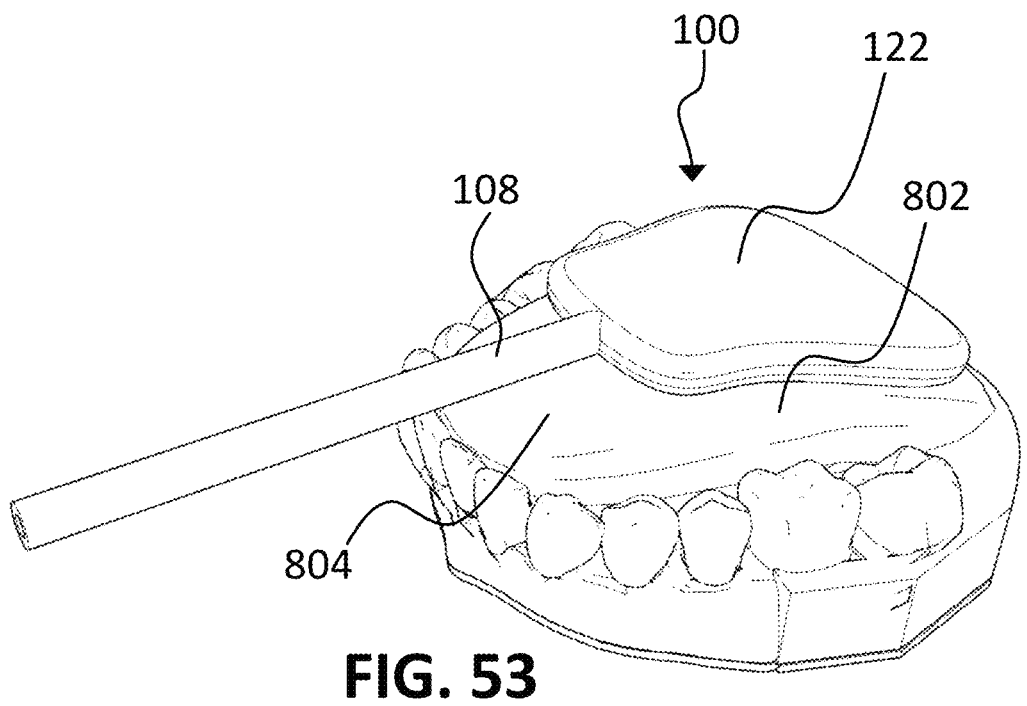
FIG. 53 shows a top view of the embodiment of FIG. 52.

FIGS. 52 and 53 show two views of a device comprising a suction anchor of the present invention. FIG. 52 shows the underside or bottom of suction anchor 122 comprising one or more suction wells 628 that apply suction to the anatomy such that suction anchor 122 reversibly attaches to the anatomy. Suction anchor 122 is connected to an elongate member 108. Vacuum may be supplied to suction wells 628 through elongate member 108. For example, a housing or body 800 of suction anchor 122 may be at least partially define a cavity therein such that the cavity is in fluid communication with a lumen defined by the elongate member 108 so that a vacuum force is applied through the lumen and the cavity onto a surface of a tongue. The size of the suction wells 628 may not be similarly sized or differentially sized. Further, as one of skill in the art will appreciate, the suction wells 628 may be any shape, for example, circular, oval, square, rectangular, etc. Suction wells 628 may be designed to fit the tongue surface. For example, larger tongues may require suction wells with a larger surface area or volume or a higher density of suction wells 628 on the bottom of the suction anchor 122. Similarly, smaller tongues may require suction wells with a smaller surface area or volume or a lower density of suction wells 628 on the bottom of the suction anchor 122. Of course, the opposite configuration for each tongue size is also envisioned. Suction wells 628 may comprise one or more valves to retain vacuum once suction anchor 122 is placed on the tissue and/or a vacuum source is removed. In one such embodiment, each suction well 628 comprises a single valve. The edges of suction wells 628 may be tapered or may comprise a soft and/or porous material to ensure that the applied vacuum is not lost. The dimensions of suction anchor 122 may vary along its length and/or be custom sized for a size or shape of an individual's tongue or anatomy. For example, the distal region of suction anchor 122 may be wider or narrower than its proximal region. Again, this feature may also be sized or shaped based on an individual's anatomy.

FIG. 53 shows the suction anchor 122 attached to the dorsal surface 802 of the tongue 804. Such a suction anchor 122 may be used for any of the methods and devices disclosed herein. Suction anchors 122 may be made of materials such as silicone, Thermoplastic Polyurethane, urethane, natural rubbers, or other materials listed in this specification. Suction anchors 122 may be designed such that the tissue contacting region (e.g., tongue contacting region) is made of a soft durometer material for increased patient comfort. The tissue contacting region may comprise one or more of the suction wells 628 and/or a bottom surface of the suction anchor 122 (shown in FIG. 52). Suction anchors 122 may be designed to be flat such that they comfortably fit in the mouth of the patient.

Figure 54:
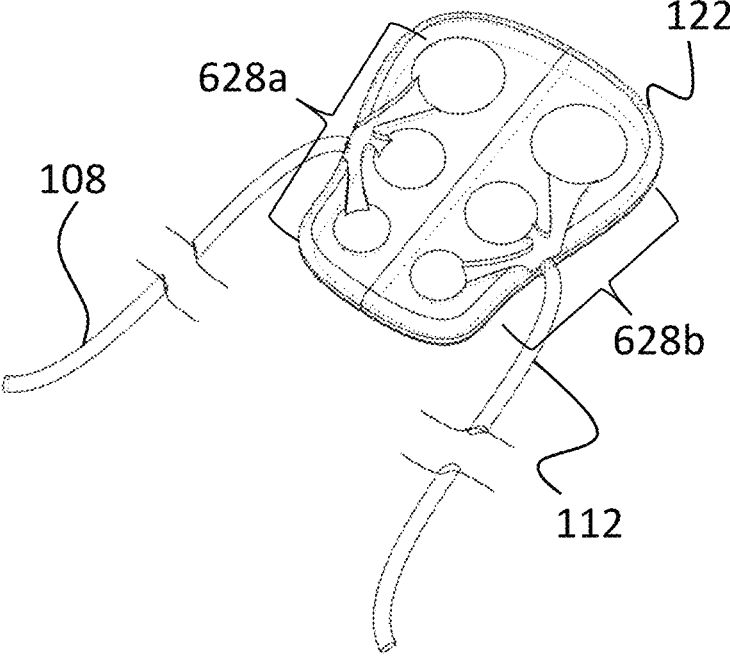
FIG. 54 shows another embodiment of a suction-based device comprising multiple suction wells.

FIG. 54 shows a view of an alternative embodiment of a suction anchor comprising multiple suction wells. Suction anchor 122 is connected to first elongate member 108 and second elongate member 112. Vacuum may be supplied to suction wells 628 through one or both of first elongate member 108 and second elongate member 112. In the embodiment shown, a first set of suction wells 628a are in fluid communication with first elongate member 108 and a second set of suction wells 628b are in fluid communication with second elongate member 112. Thus, even if vacuum is lost from one set of suction wells 628a, 628b, the other set will ensure that suction anchor 122 stays attached to the tissue. In another embodiment, the suction wells 628b on one side of suction anchor 122 are in fluid communication with first elongate member 108 and the suction wells 628a on the other side are in fluid communication with second elongate member 112. In still a further embodiment, all or substantially all suction wells are in communication with both elongate members 108, 112, such that if suction is lost through one member, the other can compensate for all wells.

FIGS. 55 and 56 show alternate embodiments of suction anchors comprising multiple suction wells. As shown in FIG. 55, the body 800 defines a suction lumen 810 that at least partially circumscribes one or more wells 628. The suction lumen 810 is in fluid communication, via fluid connection 812, to each of the suction wells 628 so that a vacuum force can be applied to each well. In FIG. 56, multiple suction wells 628 are in fluid communication with each other through one or more fluid connections 630. Each fluid connection may comprise a first end fluidly coupled to a first well and a second end fluidly coupled to a second well. The first and second wells may be adjacent, orthogonally, diagonally, in line, or otherwise relative to one another.

FIG. 57 shows an embodiment of a suction anchor with a palate actuated suction mechanism comprising multiple suction wells. Suction anchor 122 comprises a device pad 632 on the side of suction anchor 122 opposite to suction wells 628 (and thus opposite the side contacting the anatomy or tissue). Device pad 632 defines a cavity therein that when force is applied to it, expels any fluid in the cavity to create a negative pressure in the cavity. In one method embodiment, the patient places suction anchor 122 on the dorsal side of the tongue and moves the tongue superiorly to press device pad 632 against the palate. This would cause the palate to press on device pad 632 with a sufficient force which would expel fluid or air from the device pad 632 and thus suction anchor 122. Moving the tongue away from the palate will create a vacuum in each of the wells of the suction anchor 122 that are in contact with the tissue, which would cause adhesion of suction anchor 122 to the tongue. The region of device pad 632 that contacts the palate may be made of a soft durometer material for increased patient comfort.

Any of the suction anchors 122 disclosed herein may comprise a suction cup that is pinched or squeezed by the patient. In one method embodiment of using such a suction anchor, the patient pulls the tongue out and pinches or squeezes the suction cup to force air out of the suction cup and create a vacuum. The position of such a suction anchor 122 on the tongue may be adjusted one or more times as disclosed elsewhere in this specification. The patient may pull the tongue out and press or squeeze the suction cup again to detach it from the tongue.

Even though the above embodiments show multiple suction wells on a single suction anchor 122, the suction wells may be located on multiple suction anchors 122. Examples of such embodiments are disclosed later in this specification. Two or more of such suction anchors 122 may be mechanically coupled to each other. In any of the embodiments herein, two or more of such suction wells 628 or suction anchors 122 may be supplied with independent vacuum channels such that a loss of vacuum in one suction well 628 or suction anchor 122 does not cause the loss of vacuum in another suction well 628 or suction anchor 122.

Further, any of the embodiments of FIGS. 52-57 may be tethered to another anatomy of the patient, for example teeth, as described elsewhere herein, to displace the tongue anteriorly. Additionally, or alternatively, where any elongate member is used to supply the vacuum to the suction anchor, the elongate member may provide the anterior force needed to displace the tongue.

Figure 58:
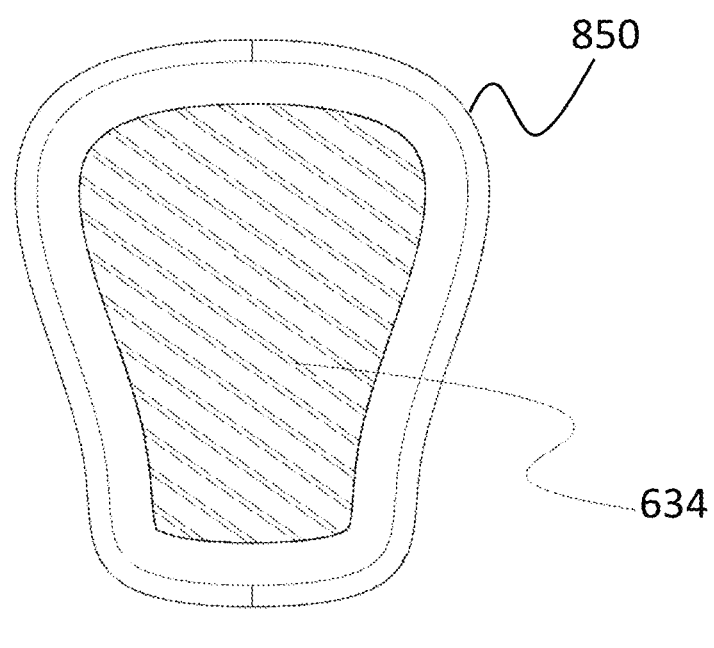
FIG. 58 shows an embodiment of an anchor comprising an adhesive region.

One or more adhesives may be used to attach an anchor including, but not limited to tongue anchors disclosed herein to a bodily region. FIG. 58 shows an embodiment of an anchor comprising an adhesive region. In the embodiment shown, anchor 850 is designed to be a tongue anchor and adhesive region 634 comprises an adhesive for attaching anchor 850 to the tongue. In one embodiment, adhesive region 634 is covered with a peel-off layer that is removed by the patient before attaching anchor 850 to the tongue.

Figure 59:
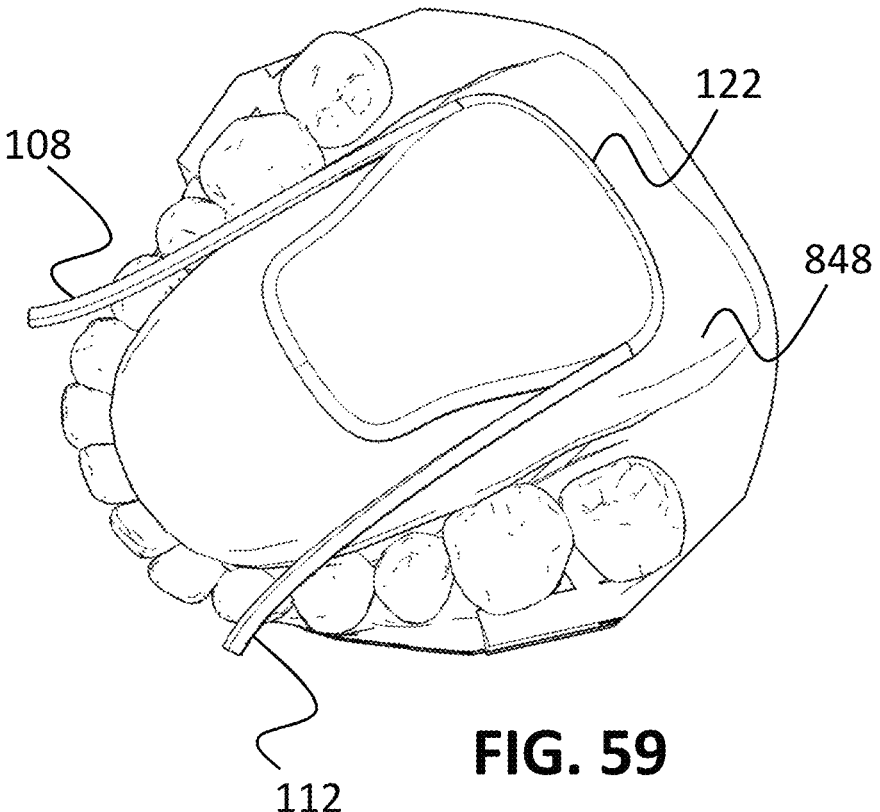
FIG. 59 shows another embodiment of an anchor comprising an adhesive region.

FIG. 59 shows an embodiment of a suction anchor 122, as described elsewhere herein, comprising an adhesive region 634 (shown in FIG. 58) attached to the tongue 848. Suction anchor 122 of FIG. 59 is connected to first elongate member 108 and second elongate member 112 for vacuum, as described elsewhere herein.

Examples of adhesives that can be used in the present invention include, but are not limited to: acrylates (e.g. cyanoacrylates), silicone based adhesives (e.g. adhesives similar to those used for attaching ostomy pouches), natural rubber latex based adhesives, hydrocolloids, hydrogels, polyurethanes, pressure sensitive adhesives, temperature sensitive adhesives, adhesives similar to denture adhesives, zinc or zinc oxide based adhesives, protein based adhesives (including elastin based adhesives, adhesives based on bio-mimicry (e.g. based on mollusk adhesion principles), etc.

Any of the adhesives disclosed herein may be loaded on a backing layer. Examples of materials used for the backing layer include, but are not limited to: cloth, foam, paper, plastic, silk or other natural materials, films (e.g. semiper-meable transparent films incorporating materials such as silicone or acrylate), etc. An adhesive may be bonded to a backing layer using a primer. Any of the device disclosed herein (especially adhesive based devices) may comprise one or more release coatings or layers.

During use, the user may press one or more regions of the device onto the tongue to activate the adhesive by increasing the surface area contact.

Any of the devices and components disclosed herein may comprise or may be used with a protectant to protect tissue surfaces like tongue surface, or a surface of the oral cavity. The protectant may protect the tissue surface from irritation by forming a protective interface between the tissue surface and one or more device surfaces or adhesives. Such protectants may be an external agent (including, but not limited to: liquid barrier films, sprays, foams, wipes, ointments, moisturizing agents, creams, etc.) or may be incorporated in or on the device.

Figures 60, 61:
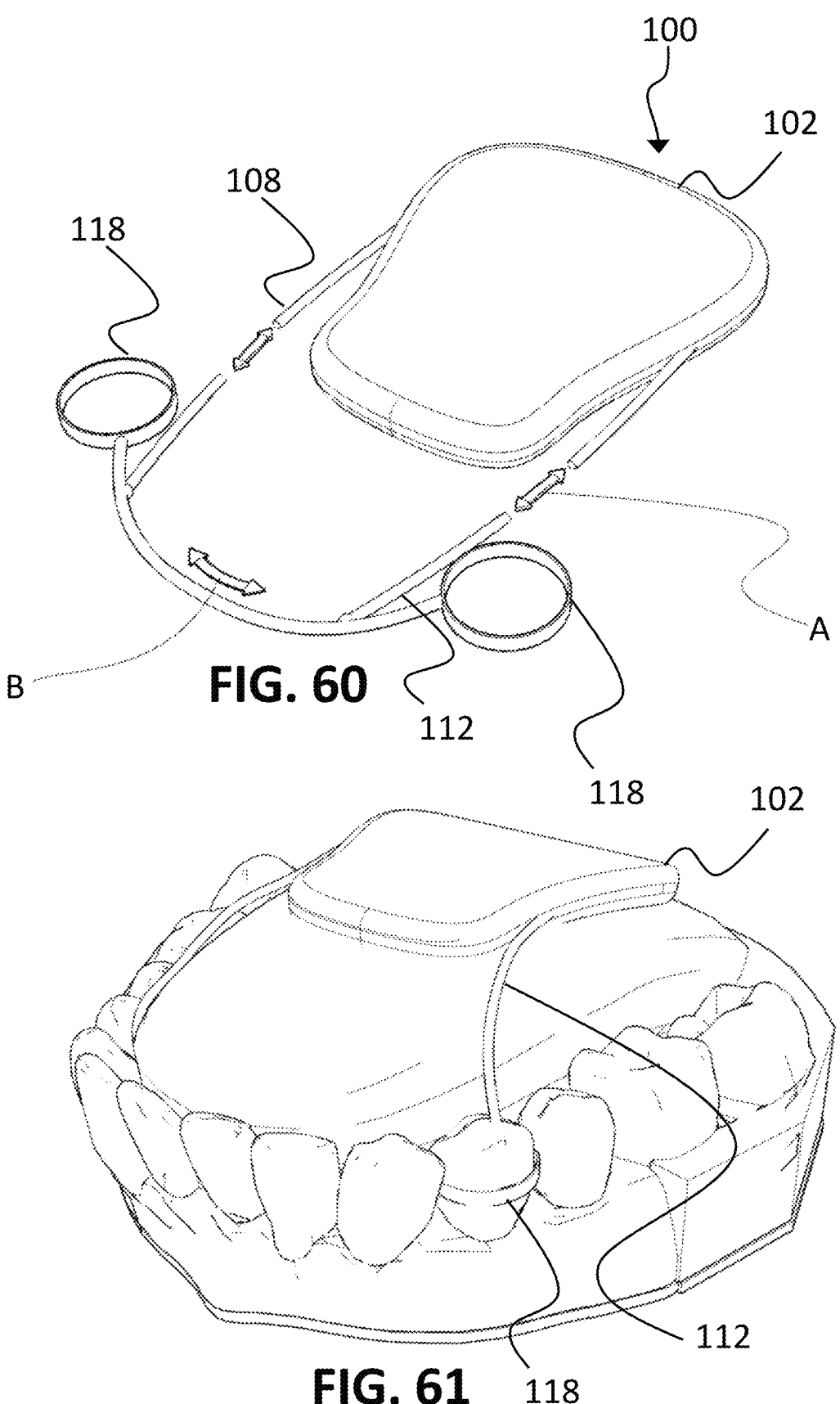
FIG. 60 shows an embodiment of a device showing two alternate mechanisms for adjusting the functioning of the device.
FIG. 61 shows an embodiment of a device that is attached to one or more teeth on the mandible.

FIG. 60 shows an embodiment of a device showing two alternate mechanisms for adjusting the functioning of the device. Device 100 comprises an anchor 102 connected to a first elongate member 108 and a second elongate member 112. First elongate member 108 and second elongate member 112 may be connected to one or more external anchors 118. In the embodiment shown, external anchors 118 are designed to be attached to one or more teeth. Mechanism A shown may be used to adjust one or both of first elongate member 108 and second elongate member 112 to adjust the action of device 100 as disclosed elsewhere in this specification. Mechanism A may be operated by the patient or by a healthcare professional. The mechanism may be used to adjust one or more of: length, orientation, stiffness, etc. of one or both of first elongate member 108 and second elongate member 112. Mechanism B shown may be used to adjust the dimensions of device 100 to adjust the action of device 100 as disclosed elsewhere in this specification. Mechanism B may be operated by the patient or by a healthcare professional. The mechanism may be used 44 adjust one or more of: length, orientation, stiffness, etc. of device portions other than first elongate member 108 and second elongate member 112.

FIG. 61 shows an embodiment of a device that is attached to one or more teeth on the mandible. Device 100 comprises an anchor 102 that is connected by one or more elongate members 108 to one or more external anchors 118. Examples of anchor 102 are disclose elsewhere in this specification. External anchors 118 in this embodiment are designed to be attached to one or more teeth on the mandible. Any of the elongate anchors 108 disclosed herein (including those in FIG. 61) may be flexible or rigid or semi-flexible.

Any of the devices disclosed herein may comprise a mechanism configured to resist dislodgement of the suction anchor. For example, FIG. 62 shows an embodiment of a suction anchor comprising one or more internal flaps 138 that contact the surface of the tongue and are configured to resist dislodgement of the suction anchor. In the embodiment shown, flaps 138 are located within a cavity of suction anchor 102. In one embodiment, flaps 138 are located around a majority of or a portion of the internal perimeter of suction anchor 102. One or more flaps 138 may be flexible such that the angle of a flap 138 relative to the rest of suction anchor 102 changes as a force is applied to suction anchor 102. As suction anchor 102 is pulled away from tissue (e.g., because of a force on a connector), the volume enclosed by suction anchor 102 and the tissue surface increases. Since the amount of air within suction anchor 102 doesn't change, the increase in volume causes the pressure inside suction anchor 102 to fall, thereby increasing the vacuum inside suction anchor 102. Thus, the force with which suction anchor 102 is attached to tissue increases which in turn resists dislodgement of suction anchor 102 i.e., increases stability of the attachment between suction anchor 102 and the tissue. Thus, flaps 138 act as a mechanism to resist dislodgement of suction anchor 102. Flaps 138 may also perform one or more functions including, but not limited to: resisting rotation of suction anchor 102, resisting sliding of suction anchor 102 over a tissue surface, and increasing a vacuum on application of a force to the suction anchor 102.

FIG. 63 shows an embodiment of a suction anchor comprising one or more external flaps 139 that contact the surface of the tongue and are configured to resist dislodgement of the suction anchor. In the embodiment shown, flaps 139 are located on an external region of the suction anchor 102. In one embodiment, flaps 139 are located at least partially around a perimeter of suction anchor 102. The perimeter may reside at an interface between a first side of a body of the device and a second side of the body of the device. One or more flaps 139 may be flexible such that the angle of a flap 139 relative to the rest of suction anchor 102 changes as a force is applied to suction anchor 102. As suction anchor 102 is pulled away from tissue (e.g., because of a force on a connector), the volume enclosed by suction anchor 102 and the tissue surface increases. Since the amount of air within suction anchor 102 doesn't change, the increase in volume causes the pressure inside suction anchor 102 to fall, thereby increasing the vacuum inside suction anchor 102. Thus, the force with which suction anchor 102 is attached to tissue increases which in turn resists dislodgement of suction anchor 102 i.e., increases stability of the attachment between suction anchor 102 and the tissue. Thus, flaps 139 act as a mechanism to resist dislodgement of suction anchor 102. Flaps 139 may also perform one or more functions including, but not limited to: resisting rotation of suction anchor 102, resisting sliding of suction anchor 102 over a tissue surface, and increasing a vacuum on application of a force to the suction anchor 102. In the embodiment of FIG. 63, suction anchor 102 comprises both internal flaps 138 and external flaps 139. In other embodiment, suction anchor 102 may comprise only one or more external flaps 139 or only one or more internal flaps 138. Any of the flaps 138 or 139 disclosed herein may be designed such that their mechanical properties vary along the radial direction away from a suction anchor. In one such embodiment, the outermost region of an external flap 139 is softer or less stiff than a region of external flap 139 closest to anchor 102. In another such embodiment, the innermost region of an internal flap 138 is softer or less stiff than a region of internal flap 138 closest to anchor 102. Any of the flaps 138 or 139 disclosed herein may be made of stiff or flexible materials, examples of which include, but are not limited to: metals, plastics, polymers (e.g., silicone), rubber materials, foams, gels, elastic materials, etc.

FIGS. 64A and 64B show one mechanism of action of an embodiment of a suction anchor comprising one or more external flaps. In the embodiment shown, suction anchor 102 comprises one or more external flaps 139 and a connector 108 i.e., a first elongate member 108. Any of the connectors described herein, attached to a vacuum source, may define a lumen that is in fluid communication with the vacuum source, After suction anchor 102 is attached to a tongue surface, the flaps 139 contact the surface of the tongue and are parallel to the tongue surface. During use, suction anchor 102 experiences forces exerted by connector 108. These forces prevent the posterior displacement of the tongue thereby proving a clinical benefit to the patient as disclosed elsewhere in this specification. However, the forces exerted on suction anchor 102 by connector 108 also may cause the detachment of suction anchor 102 from the tissue. Since suction anchor 102 is attached to tissue, these forces create a torque which in turn may cause suction anchor to rotate and detach from the tissue. In FIG. 64B, there is a slight rotation of suction anchor 102, however, this rotation causes the flaps 139 on the side of the connector to push into the tissue as shown. As shown, the angle and/or orientation of the flaps 139 on the side of the connector relative to the rest of suction anchor 102 changes. This in turn mechanically resists the rotation of suction anchor 102. This in turn resists the detachment of suction anchor 102 from the tissue, thereby improving the stability of the attachment of suction anchor 102 to the tissue. Flaps 139 may be elastic such that on removal of the torque, suction anchor 102 reverts to the configuration shown in FIG. 64A. Flaps 139 may also perform other actions as disclosed elsewhere in this specification, examples of which include, but are not limited to: resisting sliding of suction anchor 102 over a tissue surface and increasing a vacuum on application of a dislodging force to suction anchor 102.

Figure 65:
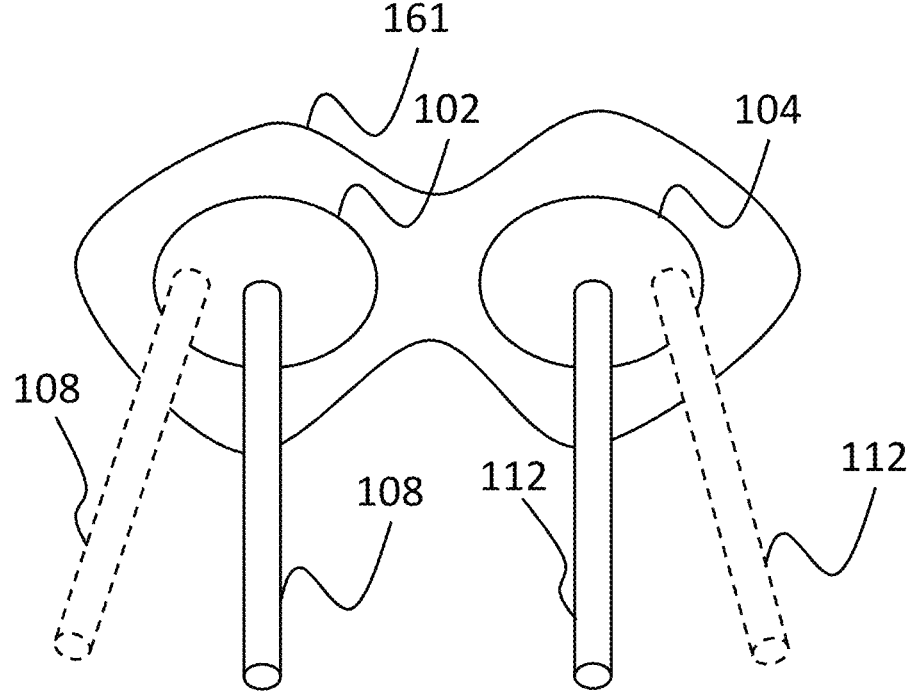
FIG. 65 shows an embodiment of a device comprising multiple anchors connected to each other.
Figure 66:
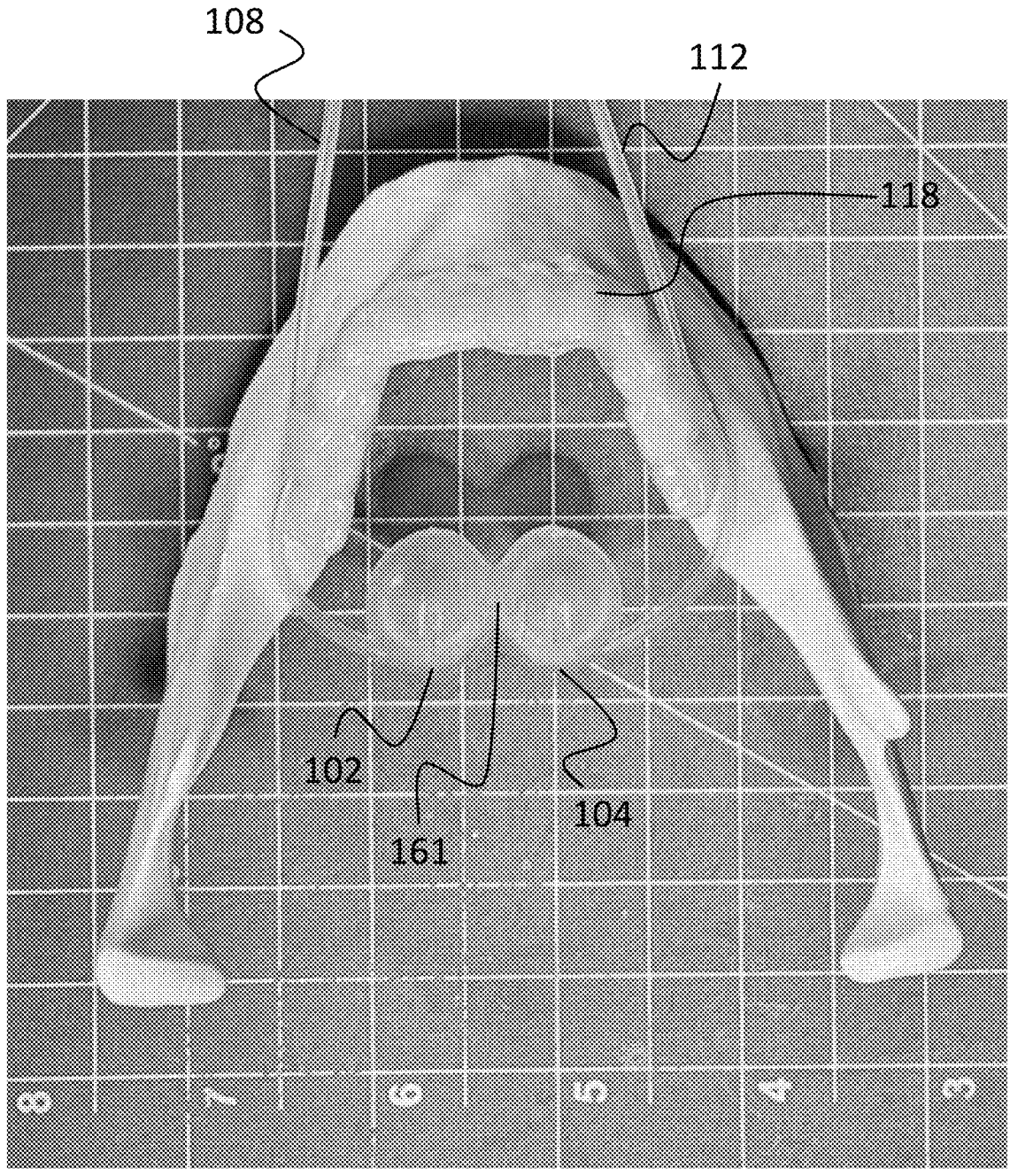
FIG. 66 shows an embodiment of a device comprising a dental anchor and two suction anchors shown in relation to a mandible.

FIG. 65 shows an embodiment of a device comprising multiple anchors connected to each other. In the embodiment shown, a first anchor 102 and a second anchor 104 are connected to each other through an anchor coupler 161. First anchor 102 and second anchor 104 may be any of the anchors disclosed herein that are connected to each other through a flexible anchor coupler 161. One advantage of an embodiment comprising multiple independently-acting anchors is that the dislodgement of one anchor from tissue may not cause the loss of a therapeutic action of the device if the second anchor is still attached to the tissue. For example, the loss of vacuum in suction anchor 102 may not cause the loss of a therapeutic action of the device if second anchor 104 is still attached to the tissue. First anchor 102 and second anchor 104 may be connected or stabilized to a region of the body through first elongate member 108 and second elongate member 112 respectively. In the embodiment shown, first elongate member 108 and second elongate member 112 are oriented along the anterior direction. However, any of the connectors disclosed herein may be oriented in alternate directions, one example of which is shown by the orientations of first elongate member 108 and second elongate member 112 represented as dashed lines. First anchor 102 and second anchor 104 may create two independent vacuum attachments at two different locations on the tongue. Coupler 161 may also act as an external flap 139. Coupler 161 may be sufficiently flexible to allow the deployment or attachment of first anchor 102 and second anchor 104 in two different orientations on the tissue. Coupler 161 may be designed such that it creates a sift junction to isolate suction anchors from each other. Coupler 161 may be designed such that at least 0.5 mm of coupler 161 is located around at least one portion of first anchor 102 and second anchor 104. In one embodiment, the distance of coupler 161 between of first anchor 102 and second anchor 104 is at least about 1 mm. In one embodiment, first anchor 102 and second anchor 104 are directly connected to each other through a flexible interface that acts as a coupler 161. FIG. 66 shows an embodiment of a device comprising a dental anchor and two suction anchors shown in relation to a mandible. In the embodiment shown, the device comprises a dental anchor 118 that acts as an external anchor 118 and is attached to the teeth as shown. The device further comprises a first anchor 102 and a second anchor 104 that are connected to the dental anchor 118 through first elongate member 108 and second elongate member 112 respectively. First elongate member 108 and second elongate member 112 comprise a lumen through which a suction is applied to a suction well of both first anchor 102 and second anchor 104. In one embodiment, a single vacuum source (not shown) provides a vacuum to both first anchor 102 and second anchor 104 through first elongate member 108 and second elongate member 112. In one such embodiment, first elongate member 108 and second elongate member 112 each comprise a one-way valve (not shown) that retains vacuum after the vacuum source is removed. In an alternate embodiment, first anchor 102 and second anchor 104 each comprise a one-way valve (not shown) that retains vacuum after the vacuum source is removed. In this way, vacuum on a suction anchor is retained even if the other suction anchor loses its vacuum. In one embodiment, the device comprises a single valve. Dental anchor 118 may be formed using processes such as molding, casting, forming, heat setting, etc. such that it is customized to fit one or more teeth of the patient. First elongate member 108 and second elongate member 112 or other device regions are attached to dental anchor 118 while dental anchor 118 is being manufactured. This may be done using techniques such as embedding or fusing or bonding materials. In an alternate embodiment, one or more connectors or other device regions are attached to the dental anchor after the dental anchor is manufactured. The distance of first elongate member 108 between dental anchor 118 and first anchor 102 and the distance of second elongate member 112 between dental anchor 118 and second anchor 104 may be fixed or may be adjustable. In one embodiment, these distances are customized to one or more of: the patient's anatomy and the patient's clinical condition. In one embodiment, these distances are adjusted after an initial use a disclosed elsewhere in this specification. Although FIG. 66 shows first elongate member 108 and second elongate member 112 oriented at an angle of about 50-60 degrees to the central axis of the mandible, that angle in any embodiment disclosed herein may range from zero degrees (i.e., first elongate member 108 and second elongate member 112 oriented along the central axis and pointing in the anterior direction) to more than about 90 degrees. The angle of orientation of first elongate member 108 and second elongate member 112 may be customized to a patient's anatomy to ensure a good fit in the patient's mouth and for patient comfort. Since elongate member 108 transmits a force during use, the direction of the force exerted by elongate member 108 on suction anchor 102 is directly related to the orientation of elongate member 108.

Figure 67:
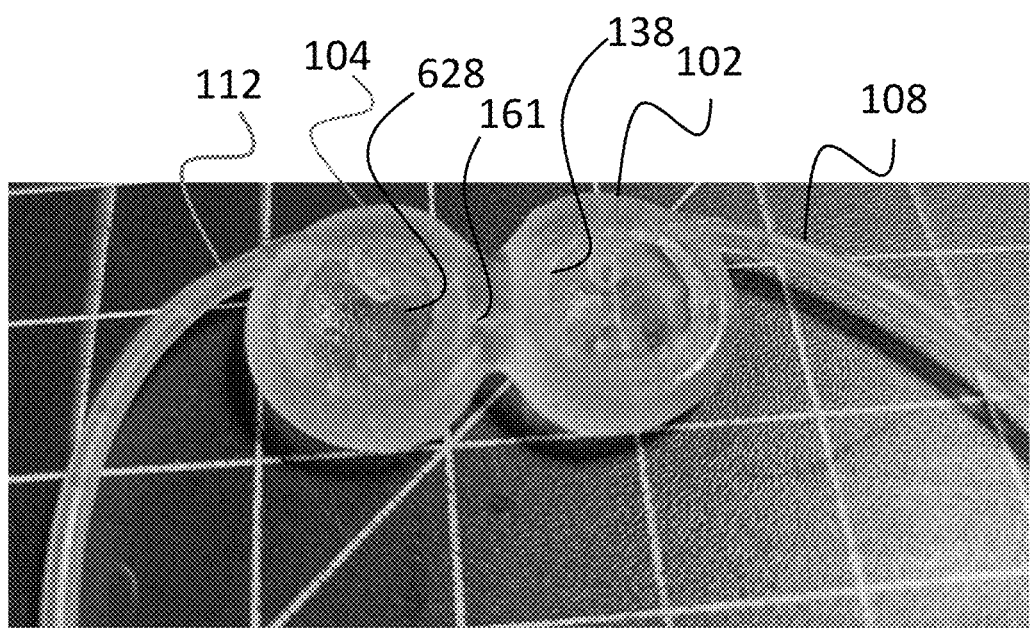
FIG. 67 shows the design details of the suction anchors shown in FIG. 66.

FIG. 67 shows the design details of the suction anchors shown in FIG. 66. The device in FIG. 67 comprises a first anchor 102 and a second anchor 104 in fluid communication with first elongate member 108 and second elongate member 112 respectively. Each suction anchor is roughly rounded in shape and comprises a suction well 168. The diameter of each suction anchor may range from about 3 mm to about 2 cm, about 3 mm to about 1 cm, about 5 mm to about 1 cm, etc. Each suction anchor further comprises an internal flap 138. In the embodiment shown, internal flaps 138 of both first anchor 102 and second anchor 104 are located around the entire internal edge of both anchors.

Figure 68:
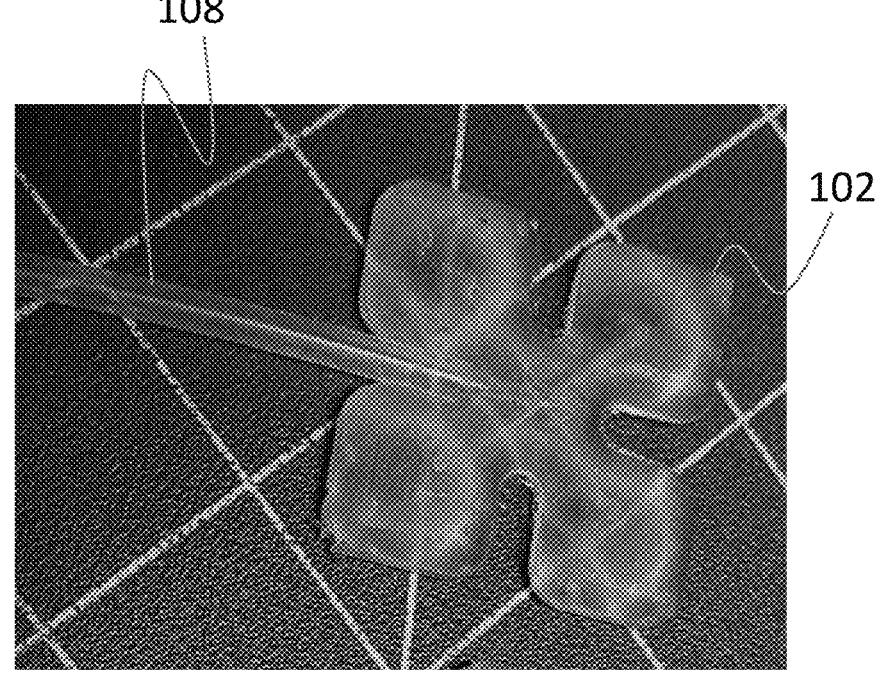
FIG. 68 shows an embodiment of a device comprising more than two suction anchors.

FIG. 68 shows an embodiment of a device comprising more than two suction anchors. In the specific embodiment shown, four suction anchors 102 are located symmetrically around a central axis. Each suction anchor 102 is in fluid connection with a single elongate member 108. One or more valves may be present in one or more device regions as disclosed elsewhere in this specification. Each suction anchor 102 shown is approximately diamond shaped and encloses a rounded suction well. Several such embodiments are possible wherein two or more anchors are located symmetrically or non-symmetrically around a central axis.

Figure 69:
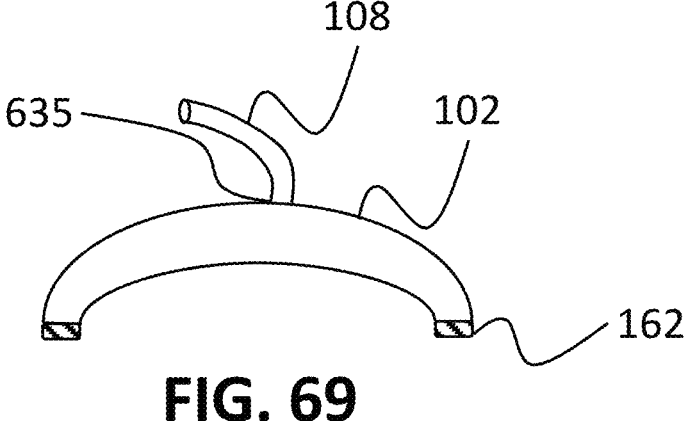
FIG. 69 shows an embodiment of a suction anchor showing various design features such as an interface layer and a pivot joint.

FIG. 69 shows an embodiment of a suction anchor showing various design features such as an interface layer and a pivot joint. Suction anchor 102 comprises an interface layer 162 that contacts the tissue surface. Interface layer may perform one or more of the following functions: improve patient comfort and/or increase stability of the attachment of suction anchor 102 to the tissue. Examples of materials that may be used to design interface layer 162 include, but are not limited to: Mechanical projections or fingers, open cell foam, closed cell foam, elastic material, a textured region, etc. Suction anchor 102 further comprises a pivot joint 635 between suction anchor 102 and connector 108. Pivot joint 635 is designed to allow connector 108 to be oriented at various orientations relative to suction anchor 102. In one embodiment, pivot joint 635 is a flexible region of connector 108 that is more flexible than a region of connector 108 away from suction anchor 102. In another embodiment, pivot joint 635 is a flexible element that connects connector 108 to suction anchor 102. In the embodiment shown, connector 108 is connected to the top of suction anchor 102. In alternative embodiments, connector 108 is connected to a region on the side of suction anchor 102. Suction anchor 102 is designed such that the mechanical properties of its wall is not uniform at all locations. In one embodiment, a region of suction anchor 102 closer to tissue is more flexible and/or thinner than the region of suction anchor 102 farther away from the tissue. Thus, during use, the region of suction anchor 102 closer to tissue bends or distorts more than the region of suction anchor 102 farther away from the tissue. This controlled bending or distortion allows suction anchor 102 to conform to the tissue surface creating a better attachment between suction anchor 102 and the tissue. In the embodiment shown, the region of suction anchor 102 closer to interface layer 162 is more flexible and/or thinner than the region of suction anchor 102 closer to connector 108. In one embodiment, the wall thickness and/or flexibility of suction anchor 102 varies at at least two locations of suction anchor 102. In one embodiment, the shape of suction anchor 102 is designed for creating a better attachment between suction anchor 102 and the tissue. As discussed later, one or more features of the embodiment of FIG. 69 may be present on one or more suction anchors 102 disclosed elsewhere in this specification.

Figure 70:
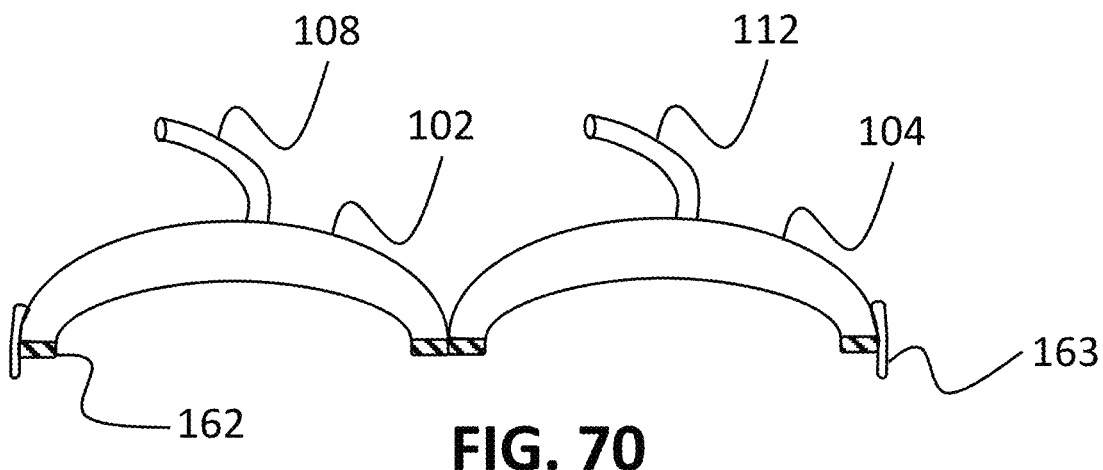
FIG. 70 shows an embodiment of a device comprising two suction anchors that comprise side stops.

FIG. 70 shows an embodiment of a device comprising two suction anchors that comprise side stops. The design of first suction anchor 102 and second suction anchor 104 is similar to that of suction anchor 102 of FIG. 69. First suction anchor

102 and second suction anchor 104 are directly attached to each other as shown. One or both of first suction anchor 102 and second suction anchor 104 comprise one or more side stops 163 as shown. One or more side stops 163 may perform one or more functions including, but not limited to: improving retention of a vacuum and preventing a suction anchor from sliding over a tissue surface.

Specific features of the devices and methods disclosed herein may be used for preventing or reducing side effects such as: excessive salivation, stripping of epidermal cells, tension injuries, tissue tears, pressure ulcers, granulation tissue, necrosis, pain or discomfort, allergic contact dermatitis, irritant contact dermatitis, etc. Examples of such features include, but are not limited to: low forces on the anatomy, flexible materials, surfaces comprising hypoallergic materials, soft surfaces in contact with tissue, rounded or other atraumatic edges in contact with tissue, larger anchors or other device components to distribute forces across a wider tissue area, etc. In one such example, the maximum force on an elongate member disclosed herein (and hence the maximum force or pressure exerted by an anchor) may be limited. The force/pressure exerted on tissue may be limited such that the pressure never exceeds or approaches perfusion pressure. Forces or pressures may be limited using one or more device features such as elastic regions, spring regions, regions that break or displace if an excessive force is applied, etc.

Various methods that can be used to diagnose/identify patients suitable for this invention and/or determine the treatment parameter(s) for any of the procedures disclosed herein include, but are not limited to: imaging, pressure transducer recording, acoustic analysis, endoscopic evaluation, measuring one or more anatomical cutoff parameter(s) of the patient, and measuring one or more symptom severity score(s) of the patient. Examples of anatomical cutoff parameters include, but are not limited to: BMI or other obesity parameters, oral anatomy score, gaps between one or more tissue regions, amount of a tissue, etc. Such methods may also be used for procedure planning (e.g., determining the type and locations of one or more anchors, size/length of one or more elongate members, tension/pull force on one or more components of device 100, forces on tongue or other tissue regions, pressures exerted on one or more tissue regions, displacement of one or more tissue regions, etc.). Examples of devices that can be used for such methods include, but are not limited to: suction tools used during awake or drug induced states, flexible or rigid elongate devices with a suction anchor at tip to pull the tongue forward, temporary implants, suction tools placed under endoscopy with the patients asked to relax their tongue, etc. Endoscopy may be used for visualizing the action of one or more methods.

In such embodiments, a sleep condition may be simulated in a patient to simulate one or more effects of the sleep state. Examples of such effects include, but are not limited to: head position and/or orientation, lack of muscle tone in the tongue, lack of muscle tone in or more structures of the airway anatomy, etc. Drug Induced Sleep Endoscopy (DISE) is an example of an endoscopic evaluation that may be used for identifying the anatomical region responsible for obstructing the upper airway and/or procedure planning. In one such embodiment, DISE (or other suitable method(s)) is used to determine the effect of any of the temporary implants described herein. Based on the information obtained during the placement of the temporary implant, further procedures can be planned. For example, more invasive or permanent procedures can be planned and performed. In some instances, as used herein, temporary implants may include surface or suction implants; and long-term or invasive implants include anchored implants, for example with tissue penetrating elements or that pass through at least a portion of the tongue tissue. However, as compared to currently available remedies, all embodiments described herein can be viewed as temporary and/or reversible since they do not substantially alter a patient's anatomy. The placement of the temporary implant can be used to determine one or more parameters of the further procedure(s). Examples of such parameters include, but are not limited to: type/location/size of one or more anchors, type/length/location of one or more elongate members, forces exerted on one or more tissue regions, pressures exerted on one or more tissue regions, displacement of one or more tissue regions, etc.

One or more portions of device 100 may comprise means for providing one or more stimuli to the tongue or other portions of the anatomy. Examples of such stimuli include, but are not limited to: thermal stimulus, vibrations or other mechanical stimulus, electrical stimulation (e.g., neurostimulation), etc. Such stimuli may be used for functions including, but not limited to: creating contraction of one or more portions of the tongue, displacing tongue portions away from posterior pharynx, increasing the tone or one or more tongue regions, rousing the patient, changing the state of consciousness or sleep of the patient, etc.

Any of the devices herein or portions of the devices herein including, but not limited to magnetic element, may be encapsulated by one or more biocompatible layers that increase the biocompatibility of one or more portions of the implant.

In any of the embodiments herein, one or more portions of the tongue and other tissue may be temporarily stabilized to enable the introduction and/or the placement of one or more portions of device 100. Examples of devices that may be used for such stabilization include, but are not limited to: clamps, suction-based tools, e.g., suction cups, elongate penetrating elements, and a part of device 100.

In one method embodiment, a temporary device 100 is implanted during the immediate post-operative phase. Thereafter, a sufficient time is allowed for the post-operative swelling to reduce. Thereafter, using the implant tract of temporary device 100, a long-term device 100 is implanted in the anatomy. Thereafter, long-term device 100 may be adjusted using any of the methods disclosed herein to adjust a clinical effect on the patient.

The steps of one method embodiment of the present invention are as follows: the user (e.g., physician, surgeon, nurse, or other operator) checks the patient for suitability of the procedure. Thereafter, the user administers anesthesia or analgesia to the patient. The user checks the tongue for location of large blood vessels. Devices 100 and other elements of the present invention, e.g., penetrating element 120, are preferably placed in regions of the tongue that lacks major blood vessels. The site(s) of the penetration and/or one or more portions of device 100 may be marked. Thereafter, the user mechanically secures the tongue, e.g., using tools like graspers, forceps, etc. and orients one or more portions of the tongue in a desired orientation. Thereafter, the tongue is punctured to insert one or more portions of the invention such as devices 100, penetrating element 120, etc. The tongue puncture may be initiated from one of dorsal, ventral, and lateral surfaces of the tongue and may extend to one of dorsal, ventral, and lateral surfaces of the tongue. The puncture may or may not extend through the full thickness of the tongue. The puncture may be performed with needles, cannulas, stylets, penetrating elements 120 or portions of devices 100. After placing devices 100, the patient may be administered one or more medications such as steroids or anti-inflammatory drugs to reduce the immediate post-procedure swelling. One or more portions of devices 100 may be coated or otherwise comprise one or more medications (including, but not limited to: steroids or anti-inflammatory drugs) to reduce the immediate post-procedure swelling. Devices 100 disclosed herein may be adjusted one or more times after the initial implantation. Examples of adjustment include, but are not limited to: changing the type, number, or location of one or more anchors; changing the type, location, length of one or more elongate members; changing one or more forces on the tongue; changing the degree of rotation of one or more portion of the tongue around rotation axis 110; and/or changing the degree of restriction to motion of one or more portions of the tongue. The length of one or more elongate members (for example, the length of an elongate member between two anchors) may be reduced after the initial procedure (for example, after two to 180 days post-procedure) to adjust device 100 for reduction in post-procedure swelling. In one embodiment, the reduction in length is between about 2 mm to about 35 mm.

One or more anchors disclosed herein may be placed through a piercing in the mid-line of the tongue. The location of an anchor may be about 2 cm; about 1.5 cm; about 2.5 cm; about 1 cm to about 2 cm; about 1.5 cm to about 2.5 cm; about 1 cm to about 3 cm; etc. or more posterior to the tip of the tongue. The location of circumvallate papillae or other anatomical regions may be used as a marker to determine the placement of any incision, penetration path, or anchor disclosed herein. In one such embodiment, one or more anchors are placed anterior to the circumvallate papillae. One or more anchors disclosed herein may be placed in the anterior third of the tongue. One or more anchors disclosed herein may be placed in regions to avoid gag reflex or swelling that may occlude air flow and cause the patient to choke.

A dorsal anchor herein may be placed further posterior to the tongue than an inferior anchor as explained previously. A dorsal anchor may be positioned using the location of the lingual frenulum as an anatomical marker.

Embodiments of the invention include combinations of multiple dorsal anchors with one or more ventral anchors. Embodiments of the invention include combinations of multiple ventral anchors with one or more dorsal anchors.

Methods and devices disclosed herein may also be used in clinical situations to remove and/or reduce and/or prevent obstruction of the airway. Examples of such situations include, but are not limited to: emergency medicine, trauma medicine, protecting the airway in patients with altered consciousness, surgeries performed under anesthesia, etc. In one such example, method and devices disclosed herein may be used in patients post-operatively (e.g., after extubation, after general anesthesia, etc.). This may allow patients to lie more comfortably on their back in the post-operative period.

One or more components of any device 100 disclosed herein may be coated with or otherwise covered with one or more pharmaceutical substances. Examples of such substances include, but are not limited to: local anesthetics; dyes and other visual markers; anti-inflammatory substances; substances with a specific taste, etc. In one embodiment, the patient covers one or more components of a device 100 (e.g., suction anchor 122, an elongate member, etc.) with a local anesthetic for increased comfort.

Any of the device embodiments herein may comprise a secondary connector between components in addition to a primary connector. The secondary connector may be used to prevent components from physically separating if the primary connector breaks. For example, the embodiment shown in FIG. 4 may comprise a secondary connector (i.e., an additional connector) that connects first anchor 102 and second anchor 104. Thus, first anchor 102 and second anchor 104 are connected by the secondary connector and also by first elongate member 108. In another such example, the embodiment shown in FIG. 25 may comprise a secondary connector that connects suction anchor 122 and external anchor 118. Thus, suction anchor 122 and external anchor 118 are connected by the secondary connector and also by first elongate member 108. Such embodiments reduce the risk of broken components falling back into the patient's airway and causing acute airway obstruction. The patient may be instructed to discard the device if one or more components and/or connectors appear to be broken. The secondary connector may be physically separate from the primary connector. The secondary connector may be integrated with or connected to the primary connector. For example, the secondary connector may be a metal wire or mesh that is integrated with or otherwise connected to an elongate member. In any of the embodiments herein, the secondary connector may be made of a material with a different strength than a primary connector.

One or more of the anchors and devices disclosed herein may be manufactured so that the anchor or device is customized to the patient's anatomy. In one embodiment, the length of a connector is adjusted to fit the patient's anatomy and/or clinical condition. In another embodiment, a dental anchor (examples of which are shown in FIGS. 5, 6, 9, 10, 25A, etc.) is manufactured using processes such as molding, casting, forming, heat setting, etc. such that the resulting dental anchor is customized to fit the patient's dental anatomy. In one embodiment, one or more connectors or other device regions are attached to the dental anchor while it is being manufactured. This may be done using techniques including, but not limited to: embedding, fusing, and bonding materials. In an alternative embodiment, one or more connectors or other device regions are attached to the dental anchor after the dental anchor is manufactured.

Although a majority of disclosure relates to the field of obstructive breathing disorders, devices, systems and methods disclosed herein may be used for one or more of: lifting, twisting, compressing, retracting, supporting or otherwise repositioning other bodily tissues. Examples of such tissues include, but are not limited to: mucosa, muscles, fascia, bones, glands, skin, etc. The devices disclosed herein may be introduced and/or used under endoscopic guidance (e.g., using cystoscopic, hysteroscopic, laparoscopic, thoracoscopic, or other endoscopic guidance). The devices disclosed herein may be introduced through natural or artificially created openings or instruments into a target bodily region. The bodily region may be one or more portions of the gastro-intestinal tract, female reproductive system, the vasculature, other parts of the ENT system, urinary system, etc. The methods disclosed herein may be performed under direct observation or under guidance of medical instrumentation, examples of which include, but are not limited to: endoscopes, radiological systems (e.g., X-ray systems, MRI scanner, CT scanner, PET scanner, etc.), ultrasound imaging systems, etc.

Although several embodiments of the invention are disclosed herein, various modifications (e.g., additions, deletions), combinations, etc. may be made to examples and embodiments herein without departing from the intended spirit and scope of the invention. Any component, anchor, connector, sensor, surgical tool, etc. of one device embodiment may be incorporated into or used for another device embodiment, unless to do so would render the resulting device embodiment unsuitable for this invention. For example, several device combinations are possible wherein the anchor of one embodiment disclosed herein is added to or used with a connector or elongate member of another embodiment disclosed herein unless doing so would render the resulting embodiment unsuitable for its intended use. In one such example, a device or method feature of one of: a suction-based device or a piercing-based device may be used on the other of: a suction-based device or a piercing-based device unless doing so would render the resulting embodiment unsuitable for its intended use. In one specific example, an external anchor (e.g., a dental anchor) of one of: a suction-based device or a piercing-based device embodiment may be used as an external anchor on the other of: a suction-based device or a piercing-based device embodiment unless doing so would render the resulting embodiment unsuitable for its intended use. Any suitable method disclosed herein may be used to attach or implant any of the devices disclosed herein. If method steps are disclosed in a particular order, the order of steps may be changed unless doing so would render the method embodiment unsuitable for its intended use. A method step described herein may be added to or used to replace a step of another method embodiment described herein. Various reasonable modifications, additions and deletions of this invention's examples or embodiments are to be considered equivalents of the described examples or embodiments.

As used in the description and claims, the singular form "a", "an" and "the" include both singular and plural references unless the context clearly dictates otherwise. For example, the term "anchor" may include, and is contemplated to include, a plurality of anchors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating obstructive breathing disorders in a patient, the method comprising:
   implanting a first implant in a tongue body of a tongue to form an implant tract within the tongue;
   removing the first implant from the implant tract of the tongue body of the tongue;
   determining one or more parameters of a procedure; and
   performing the procedure using the one or more parameters, wherein the procedure comprises:
       implanting, in the implant tract of the tongue body of the tongue, an implantable member having a tongue anchor;
       reversibly coupling a flexible elongate member to the implantable member; and
       applying a force to the flexible elongate member to generate tension on a portion of the tongue body,
       wherein at least a portion of the force is directed along an anterior direction, and
       wherein the force causes at least one of the following actions: an anterior displacement of a posterior portion of the tongue during sleep or reducing posterior displacement of a portion of the tongue during sleep.

2. The method of claim 1, wherein the first implant is used to determine the one or more parameters.

3. The method of claim 2, further comprising determining an effect of the first implant.

4. The method of claim 3, further comprising using drug induced sleep endoscopy to determine the effect of the first implant.

5. The method of claim 2, further comprising administering one or more of: a therapy that generates a positive airway pressure and a therapy that affects a portion of the airway.

6. The method of claim 2, further comprising allowing an initial healing period between a placement of the first implant and the implantation of the implantable member.

7. The method of claim 2, wherein the implantable member is connected to a tongue anchor that is physically separated by a distance from a tissue boundary of the tongue body.

8. The method of claim 1, wherein the one or more parameters comprise one or more of: a type of the implantable member, a size of the implantable member, a number of components of the implantable member, a location of placement of the implantable member, a degree of restriction of the tongue, a displacement of the tongue, a direction of the force to be applied to the tongue, or a magnitude of the force to be applied to the tongue.

9. The method of claim 1, wherein the procedure further comprises disposing the flexible elongate member superiorly to a dorsal surface of the tongue.

10. The method of claim 1, wherein the one or more parameters comprise one or more of: a patient tolerability to an implant, resolution of symptoms, a dimension of an implant, a type of implant, an anatomical location of an implant, or a number of implants.

11. A method of treating obstructive breathing disorders in a patient, the method comprising:

implanting a temporary implant in a tongue body of a tongue during a first procedure;

removing the temporary implant from the tongue body of the tongue after post-operative swelling is reduced;

performing the first procedure to determine one or more parameters of a second procedure; and performing the second procedure using the one or more parameters determined from the first procedure, wherein the second procedure comprises:

implanting, in a region of the tongue body of the tongue, an implantable member having a tongue anchor;

reversibly coupling a flexible elongate member to the implantable member; and applying a force to the flexible elongate member to generate tension on a portion of the tongue body, wherein at least a portion of the force is directed along an anterior direction, and wherein the force causes at least one of the following actions: an anterior displacement of a posterior portion of the tongue during sleep or reducing posterior displacement of a portion of the tongue during sleep.

12. The method of claim 11, wherein the one or more parameters comprise one or more of: a type of the implantable member, a size of the implantable member, a number of components of the implantable member, a location of placement of the implantable member, a degree of restriction of the tongue, a displacement of the tongue, a direction of the force to be applied to the tongue, or a magnitude of the force to be applied to the tongue.

13. The method of claim 12, comprising administering one or more of: a therapy that generates a positive airway pressure and a therapy that affects a portion of the airway.

14. The method of claim 13, wherein the second procedure further comprises disposing the flexible elongate member superiorly to a dorsal surface of the tongue.

15. The method of claim 11, wherein the temporary implant comprises a suction anchor or tool.

16. The method of claim 11, further comprising removing the temporary implant prior to the implantation of the implantable member.

17. The method of claim 11, wherein the second procedure includes implanting a long-term implant placed for more than one week.

18. The method of claim 11, wherein the implantable member is connected to a tongue anchor that is physically separated by a distance from a tissue boundary of the tongue body.

19. The method of claim 11, wherein the first procedure comprises applying suction with a suction tool.

20. The method of claim 11, wherein the first procedure comprises utilizing a mechanical tool to displace one or more tissues regions of the tongue.

* * * * *